(12) United States Patent
Ajami

(10) Patent No.: US 6,610,270 B1
(45) Date of Patent: *Aug. 26, 2003

(54) IN VIVO DETERMINATION OF METABOLIC FUNCTION FOR USE IN THERAPY MANAGEMENT

(75) Inventor: Alfred M. Ajami, Brookline, MA (US)

(73) Assignee: Xanthus Life Sciences, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/719,956

(22) PCT Filed: Jun. 29, 1999

(86) PCT No.: PCT/US99/14725

§ 371 (c)(1), (2), (4) Date: Dec. 18, 2000

(87) PCT Pub. No.: WO00/00636

PCT Pub. Date: Jan. 6, 2000

Related U.S. Application Data

(63) Continuation-in-part of application No. 09/107,965, filed on Jun. 30, 1998, now Pat. No. 6,284,219.

(51) Int. Cl.$^7$ ............................................. A61K 49/00
(52) U.S. Cl. ...................... 424/9.2; 424/1.81; 424/1.11; 435/4
(58) Field of Search .............................. 424/1.11, 1.53, 424/1.65, 1.81, 9.2, 9.1; 435/4, 183, 188, 814; 250/472.1; 600/9

(56) References Cited

U.S. PATENT DOCUMENTS

| | | | |
|---|---|---|---|
| 5,449,688 A | 9/1995 | Wahl et al. | |
| 6,284,219 B1 * | 9/2001 | Ajami | ...................... 424/1.11 |

FOREIGN PATENT DOCUMENTS

| | | | |
|---|---|---|---|
| DE | 26 26 533 A | 12/1977 | ............ G21H/5/02 |
| EP | 0 825 260 A | 2/1998 | ........... C12N/15/55 |
| EP | 0 826 377 A | 3/1998 | .......... A61K/49/00 |
| WO | WO 93 05780 A | 4/1993 | .......... A61K/31/45 |

OTHER PUBLICATIONS

Rogers et al., "In vivo synthesis and utilization of arginine in the rat", Amer. J. Physiol, vol 223, No 1 pp. 236–240.

Harmeyer et al., "The metabolic conversion of arginine in the rumen wall and its importance in ruminant nitrogen metabolism", Isotope Stud. Nitrogen Chain, Proc. Symp., Vienna, Vol. Meeting Date 1967, pp. 265–274.

Arythunyan et al., "Effects of thyroid hormones on liver arginase activity in rats'" Biol Zh. Arm, vol. 37, No. 5, pp. 416–419.

Tramell et al., "Arginine and urea metabolism in the South American land snail, Stropocheilus oblongus", Comp. Biochem. Physiol, vol. 42, No. 3 p. 445.

Birkner et al., "The influence of hyperthermia on ornithine carbamolytransferase and arginase activity in liver or rats", Ann. Acad. Med. Silesiensis, vol. 24, pp. 13–17.

Nettleton et al., "Reutilization of guanido–labeled arginine in rat liver proteins and the influence of diet", J. Nutr, vol. 104, No. 7, pp. 916–921.

Levillain et al., "Production of urea from arginine in pars recta and collecting duct of the rat kidney", Renal Physiol. Biochem. vol. 12, No. 5–6, pp. 302–312.

Klein et al., "Increased arginase activity during lymphocyte mitogenesis", Biochem. Biophys. Res. Commun, vol. 81, No. 1, pp. 199–204.

Nishibe, H., "Ultramicromethod for the determination of human arginase in the presence of urea", Clin. Chim. Acta, Sep. 20, 1976, vol. 71, No. 3, pp. 413–8.

Ruegg et al., "A rapid and sensitive assay for arginase", Analytical Biochemistry, vol. 102, No. 1, pp. 206–212.

Snejdarkova et al., "Model arginine dynamics in the Japanese quail coturnix–coturnix–japonica –1, time dependent arginine concentration changes in selected compartments", Nutrition Reports International, vol. 28, No. 4, pp. 753–760.

Pratzel et al., "Biochemistry of free amino acids in the stratum corneum of human epidermis", Arch. Dermatol, vol. 259, No. 2 pp. 151–156.

Carl et al., "Manganese and epilepsy brain glutamine synthetase and liver arginase activities in genetically epilepsy prone and chronically seizured rats", Epilepisa, US, Raven Press Ltd., NY, vol. 34, No. 3 pp. 441–446.

* cited by examiner

*Primary Examiner*—Dameron L. Jones

(57) ABSTRACT

It is an object of the present invention to provide in vivo analytical methods that allow for diagnosis and management of therapy for diseases involving discrete biochemical pathways. In the method of the invention, a labelled tracer probe, a specifically designed substrate of a "gateway" enzyme, an enzyme marking a regulatory point in a discrete biochemical pathway, is administered to a subject; a labelled product of the action of the enzyme is measured; and the appearance and concentration of the product are related to the disease condition of interest. Determination of the rate of substrate-product conversion of the gateway enzyme allows for the analysis to be made. The method involves administering a defined amount of a labelled "metaprobe" substrate of the gateway enzyme to a subject, at a site that provides access to a desired pool of the gateway enzyme in the subject, and measuring the amount of the chosen labelled product. The presence and amount of the chosen labelled product in, e.g., the breath, definitely indicates that the labelled metaprobe has been metabolized by the specific enzyme in the specific biochemical pathway under consideration, and from the calculated rate of substrate-product conversion by the gateway enzyme, the desired diagnostic determination may be made. Likewise, if a specific therapeutic treatment for a disease is underway with a patient, this method allows for a minimally invasive assessment of the effectiveness of the treatment, with minimal discomfort to the patient.

12 Claims, 25 Drawing Sheets

The γ-glutamyl cycle.
(From Meister, Science 180 : 33-39, 1973)

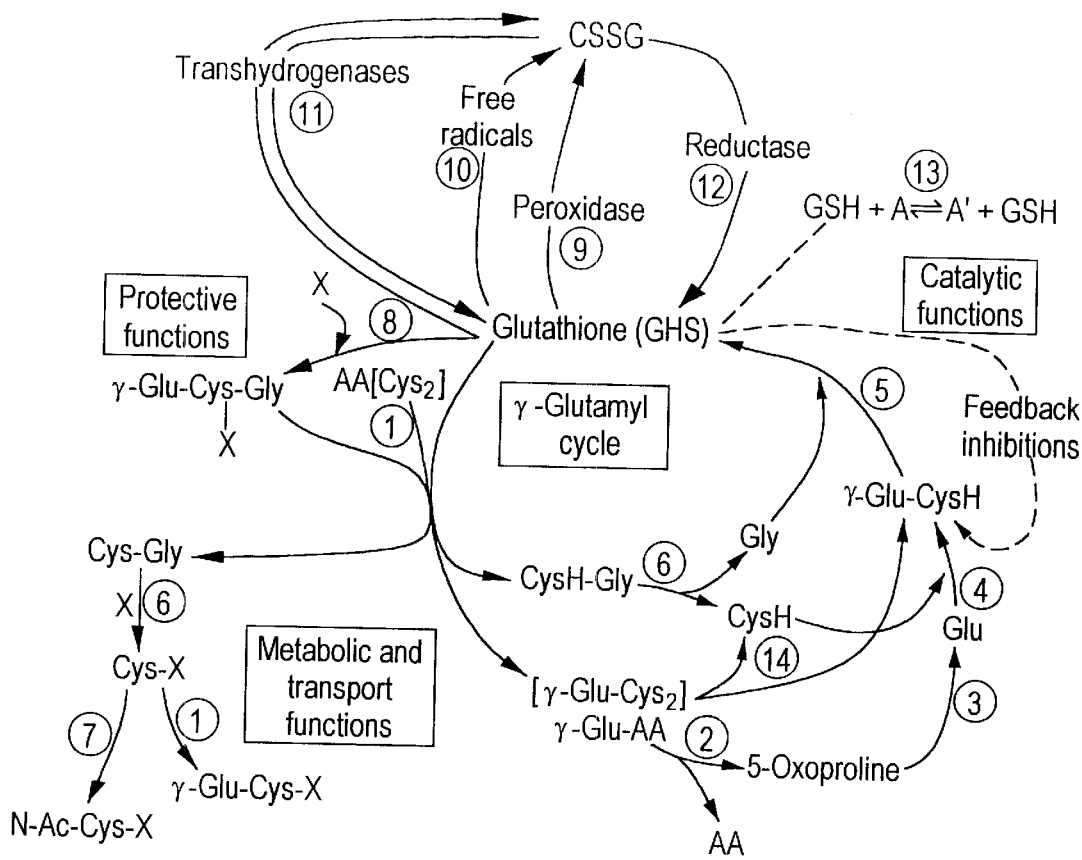

Overview of the metabolism and function of glutathione. (1) γ-Glutamyltranspeptidase; (2) γ-glutamylcyclotransferase; (3) 5-oxoprolinase; (4) γ-glutamilcysteine synthetase; (5) glutathione synthetase; (6) dipeptidase; (7) L-cysteine- S-conjugate N-acetyltransferase; (8) glutathione S-transferases; (9) glutathione peroxidase; (10) presumably nonenzymatic; (11) glutathione transhydrogenases, e.g., enzymes that catalyze thiol-protein reactions; (12) glutathione disulfide reductase; (13) reactions in which glutathione is required, but not consumed, such as those catalized by formaldehyde dehydrogenase, glyoxylase, maleylacetoacetate isomerase, DDT-dehydrochlorinase, and prostaglandin endoperoxidase isomerases; (14) transport and reduction of γ-glutamylcystine (AA = amino acids; X = compounds that form conjugates with glutathione). (Taken from Holmgren, A., Branden, C-I., Jornvall, H., and Sjoberg, B-M.; Eds.; "Thioredoxen and Glutaredoxin Systems: Structure and Function" Raven Press; New York, 1986, p. 340.)

FIGURE 1b
PRIOR ART

The interrelationships between arginine, urea cycle intermediates, polyamines, creatine, nitric oxide (NO) and proline. Slight modification of Fig. 19-2 in Valle and Simell (1995). The hyperornithenemies. In The Metabolic Basis of Inherited Disease, Vol. 1 (C. R. Scriver, A. L. Beaudet, W. S. Sly and D. Valle Eds.), pp. 1147-1186. New York: McGraw-Hill.

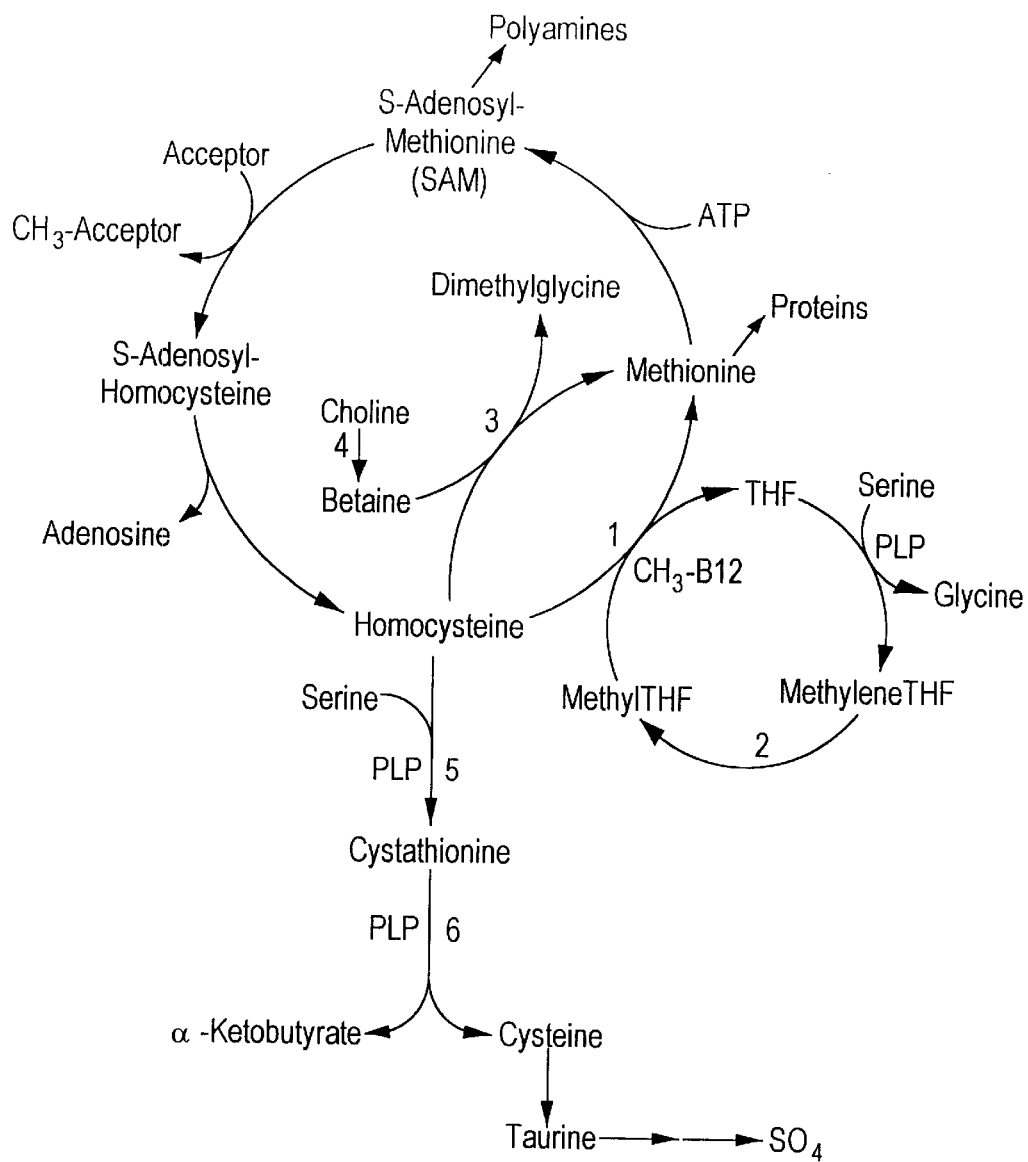

Homocyst(e)ine metabolism in humans and animals. Enzymes: 1, $N$-5-methyltetrahydrofolate:homocysteine methyltransferase; 2, methylenetetrahydrofolate reductase; 3, betaine:homocysteine methyltransferase; 4, choline dehydrogenase; 5 cystathionine β-synthase; 6,δ -cystathionase. THF, tetrahydrofolate; PLP, pyridoxal 5'-phosphate; ATP, adenosine 5'-triphosphate; B12, vitamin B . (adapted from J. Selhub and J.W. Miller. Am J Clin Nutr 1992;55;131-8)

FIGURE 3
PRIOR ART

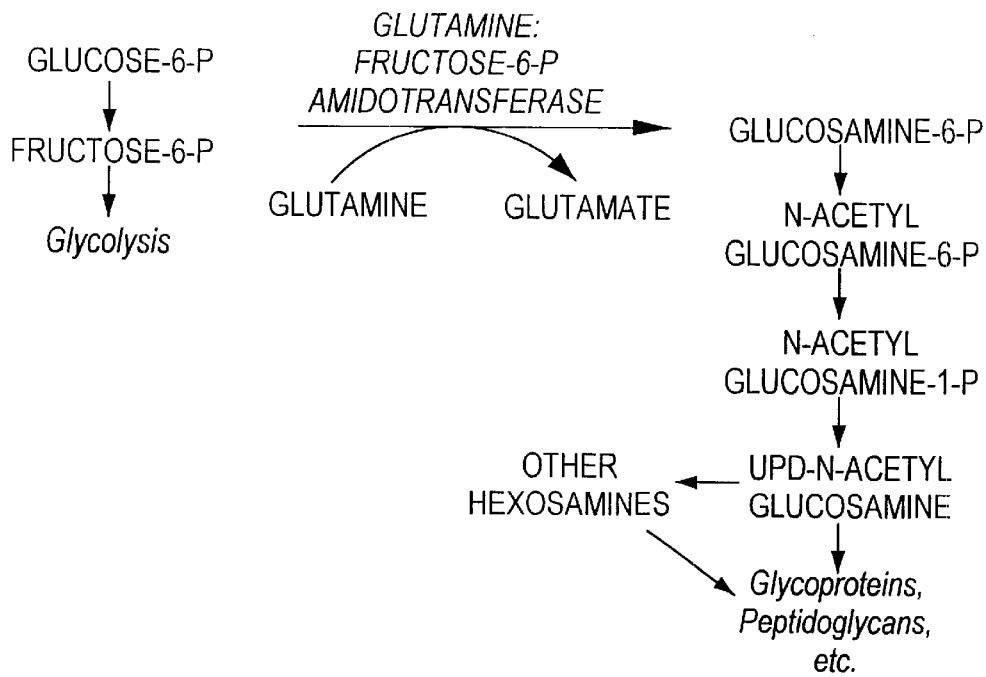
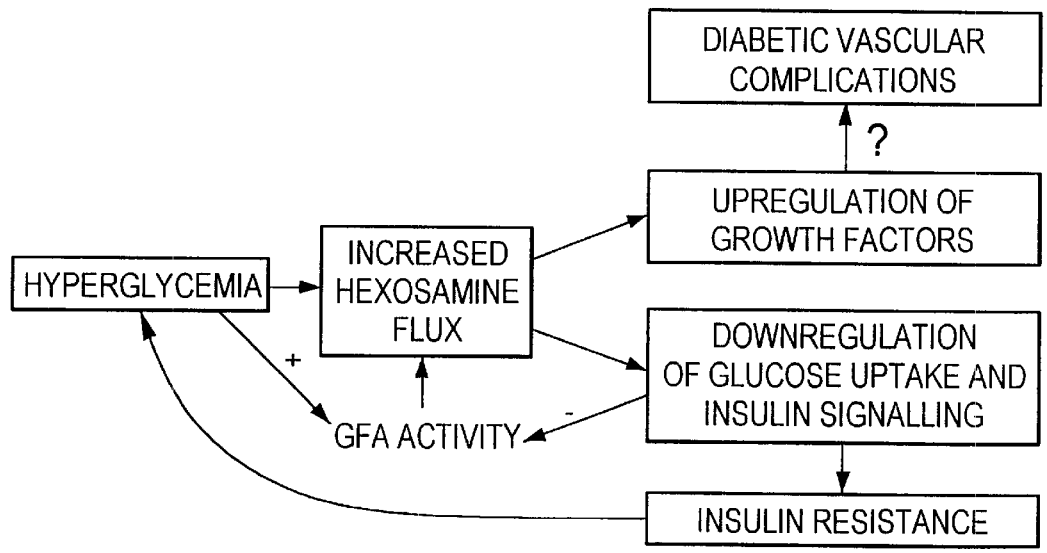
(From McClain et at., Hexosamines and Insulin Resistance; DIABETES, Vol 45, August 1996.)
FIGURE 4
PRIOR ART

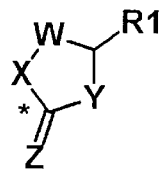

R1 = carboxyl, carboxylamide, and ketone functional groups described in Table IV, with characteristic reversible subfunctionalities, including as preferred:

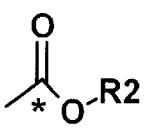 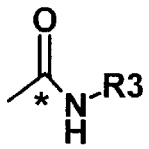 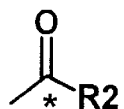

X = N, O, S

Y = N, O, S

W = CH2, CH-alkyl, CH-aryl, CH2CH2, CH2-CH-alkyl, CH2-CH-aryl

R2 = H, methyl, ethyl, propyl, butyl, pentyl, hexyl, isopropyl, isobutyl, sec-butyl tert-butyl, isopentyl, isohexyl, phenyl, phenylmethyl, etc.; or R3 = H, methyl, ethyl, propyl, butyl, pentyl, hexyl, isopropyl, isobutyl, sec-butyl tert-butyl, isopentyl, isohexyl, phenyl, phenylmethyl, etc.; or

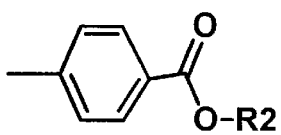

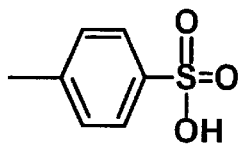

* = Preferred position of isotopic release tag in tracer core

FIGURE 5

Oxiprolinase Metaprobes

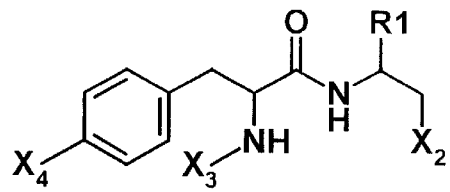

R1 = carboxyl, carboxylamide, and ketone functional groups described in Table IV, with characteristic reversible subfunctionalities, including as preferred:

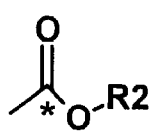 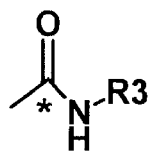 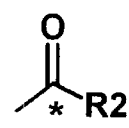

X2, R2 = H, methyl, ethyl, propyl, butyl, pentyl, hexyl, isopropyl, isobutyl, sec-butyl tert-butyl, isopentyl, isohexyl, phenyl, phenylmethyl, etc.

X3 = acetyl, benzoyl, benzyloxycarbonyl, t-butoxycarbonyl, hippuryl, methoxyacetyl, methoxycarbonyl, pivaloyl, etc.

R3 = H, methyl, ethyl, propyl, butyl, pentyl, hexyl, isopropyl, isobutyl, sec-butyl tert-butyl, isopentyl, isohexyl, phenyl, phenylmethyl, etc.; or

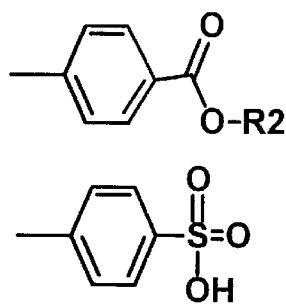

X4 = H, OH, $NH_2$, $OCH_3$

\* = Preferred position of isotopic release tag in tracer core

Figure 7

Chymotrypsin Metaprobes

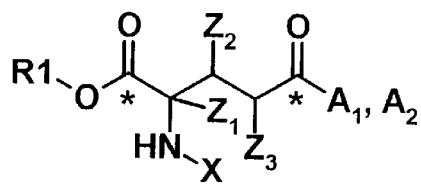

R1 = carboxyl functional groups described in Table IV, with characteristic reversi subfunctionalities, including as preferred esters, methyl, ethyl, propyl, butyl, pent hexyl, isopropyl, isobutyl, sec-butyl, tert-butyl, isopentyl, isohexyl, phenyl, phenylmethyl etc.

A1 = 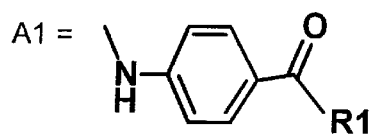

A2 = 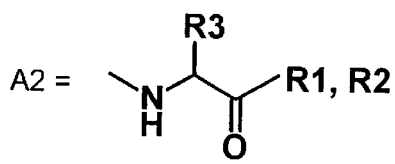

R2 = 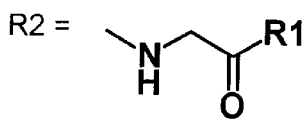

R3 = CH2-SH, CH2-S-CH3, methyl, ethyl, propyl, butyl, pentyl, hexyl, isoprop isobutyl, sec-butyl, tert-butyl, isopentyl, isohexyl, phenyl, phenylmethyl, X = acetyl, benzoyl, benzyloxycarbonyl, t-butoxycarbonyl, hippuryl, methoxyacetyl, methoxycarbonyl, pivaloyl, etc.

* = Preferred position of isotopic release tag in tracer core

Figure 8
Glutamyl Transpeptidase Metaprobes

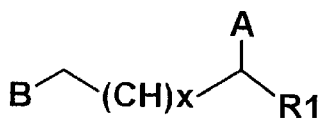

R1 = carboxyl, carboxylamide, and ketone functional groups described in Table IV, with characteristic reversible subfunctionalities, including as preferred:

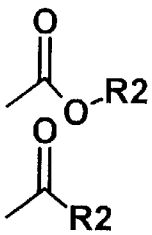

R2 = H, methyl, ethyl, propyl, butyl, pentyl, hexyl, isopropyl, isobutyl, sec-butyl tert-butyl, isopentyl, isohexyl, phenyl, phenylmehyl, etc.; or

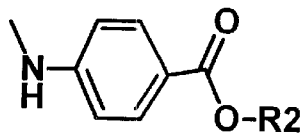

A = 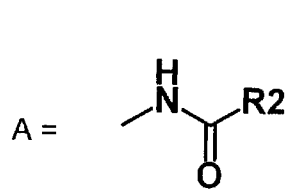

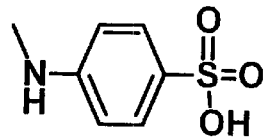

B = 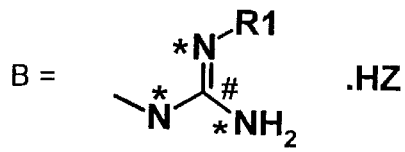

X = 1 or 2

Z = halide, mesylate, tosylate

, * = Preferred position of isotopic release tag in tracer core

FIGURE 10

Nitric Oxide Synthase Metaprobes

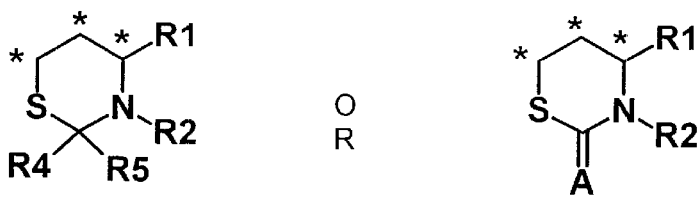

R1 = carboxyl, carboxylamide, and ketone functional groups described in Table IV, with characteristic reversible subfunctionalities, including as preferred:

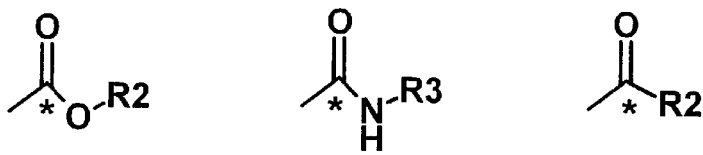

R2 = H, methyl, ethyl, propyl, butyl, pentyl, hexyl, isopropyl, isobutyl, sec-butyl tert-butyl, isopentyl, isohexyl, phenyl, phenylmethyl, etc.; or R3 = H, methyl, ethyl, propyl, butyl, pentyl, hexyl, isopropyl, isobutyl, sec-butyl tert-butyl, isopentyl, isohexyl, phenyl, phenylmethyl, etc.; or

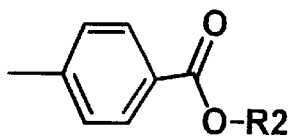

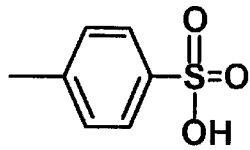

R4 = -OH, -SH, —C≡N, -NHR2, -N(R2)$_2$; or R4

R5 = H, methyl, ethyl, propyl, butyl, pentyl, hexyl, isopropyl, isobutyl, sec-butyl tert-butyl, isopentyl, isohexyl, etc.

A = NH, O, S

* = Preferred position of isotopic release tag in tracer core

Figure 11a

Cystathionine Synthase Metaprobes (Part 1)

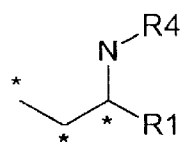

R1 = carboxyl, carboxylamide, and ketone functional groups described in Table IV, with characteristic reversible subfunctionalities, including as preferred:

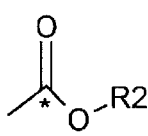 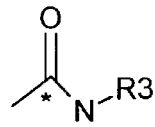 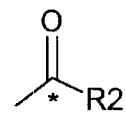

R2 = H, methyl, ethyl, propyl, butyl, pentyl, hexyl, isopropyl, isobutyl, sec-butyl tert-butyl, isopentyl, isohexyl, phenyl, phenylmethyl, etc.; or R3 = H, methyl, ethyl, propyl, butyl, pentyl, hexyl, isopropyl, isobutyl, sec-butyl tert-butyl, isopentyl, isohexyl, phenyl, phenylmethyl, etc.; or

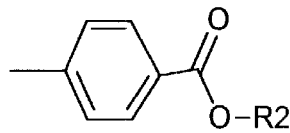

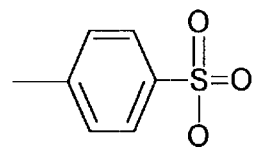

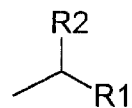

R4 = H, formyl, acetyl, benzoyl, benzyloxycarbonyl, t-butoxycarbonyl, hippuryl, methoxyacetyl, methoxycarbonyl, pivaloyl, etc.

\* = Preferred position of isotopic release tag in tracer core

Figure 11b

Cystathionine Synthase Metaprobes (Part 2)

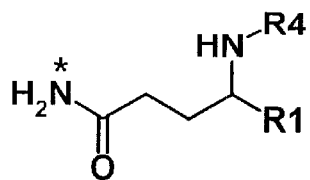

R1 = carboxyl, carboxylamide, and ketone functional groups described in Table IV, with characteristic reversible subfunctionalities, including as preferred:

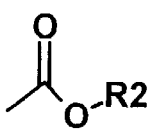 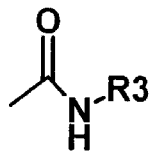 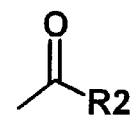

R2 = H, methyl, ethyl, propyl, butyl, pentyl, hexyl, isopropyl, isobutyl, sec-butyl tert-butyl, isopentyl, isohexyl, phenyl, phenylmethyl, etc.; or R3 = H, methyl, ethyl, propyl, butyl, pentyl, hexyl, isopropyl, isobutyl, sec-butyl tert-butyl, isopentyl, isohexyl, phenyl, phenylmethyl, etc.; or

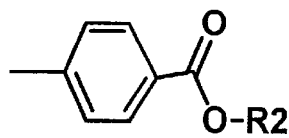

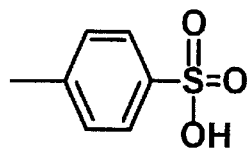

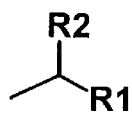

R4 = H, formyl, acetyl, benzoyl, benzyloxycarbonyl, t-butoxycarbonyl, hippuryl, methoxyacetyl, methoxycarbonyl, pivaloyl, etc.

\* = Preferred position of isotopic release tag in tracer core

Figure 12a

Glutamine Fructose-6-phosphate
Amidotransferase Metaprobes (Part 1)

R1 = H, formyl, acetyl, benzoyl, benzyloxycarbonyl, t-butoxycarbonyl, hippuryl, methoxyacetyl, methoxycarbonyl, pivaloyl, etc.

* = Preferred position of isotopic release tag in tracer core

Glutamine Fructose-6-phosphate
Amidotransferase Metaprobes (Part 2)

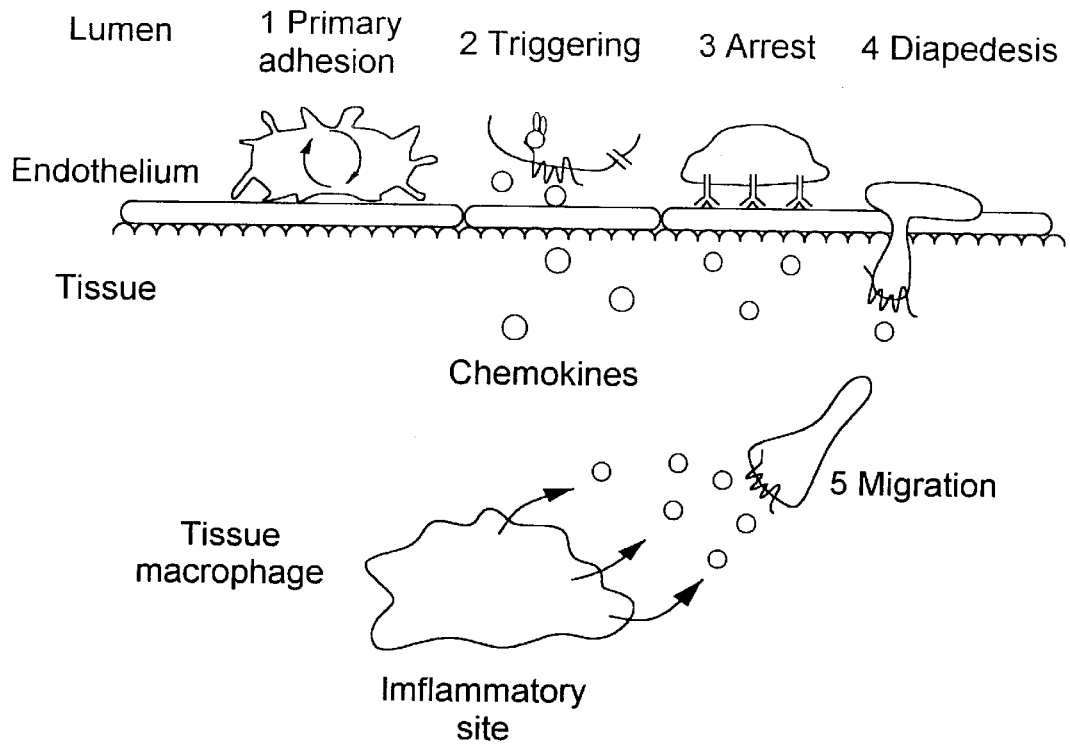

Tissue injury, bacterial or viral antigen presentation activates leucocytes and lmphocytes via membrane receptors, several of which are functionally connected to the activation of cellular peptidases on the cell surface and contained membrane vescicles. Activation or expression of these peptidases mediate the noncomitant structural transformations necessary for cell adhesion (protein hydrolysis) and chemokine secretion. Further biochemical action at the inflammatory site, involving cell lysis, phagocytosis, autocrine, and paracrine stimulation are effected cellular proteases in response to changes in metal ion titers, pH, and phosphorylation. The differentation antigens CD10, CD13, CD26, CD143 (angiotensin converting enzyme), BP1/6C3, and MAX1/MAX11 are also ecto-enzymes on cell surface of lymphoid cells (Goding and Howard)

FIGURE 13
PRIOR ART

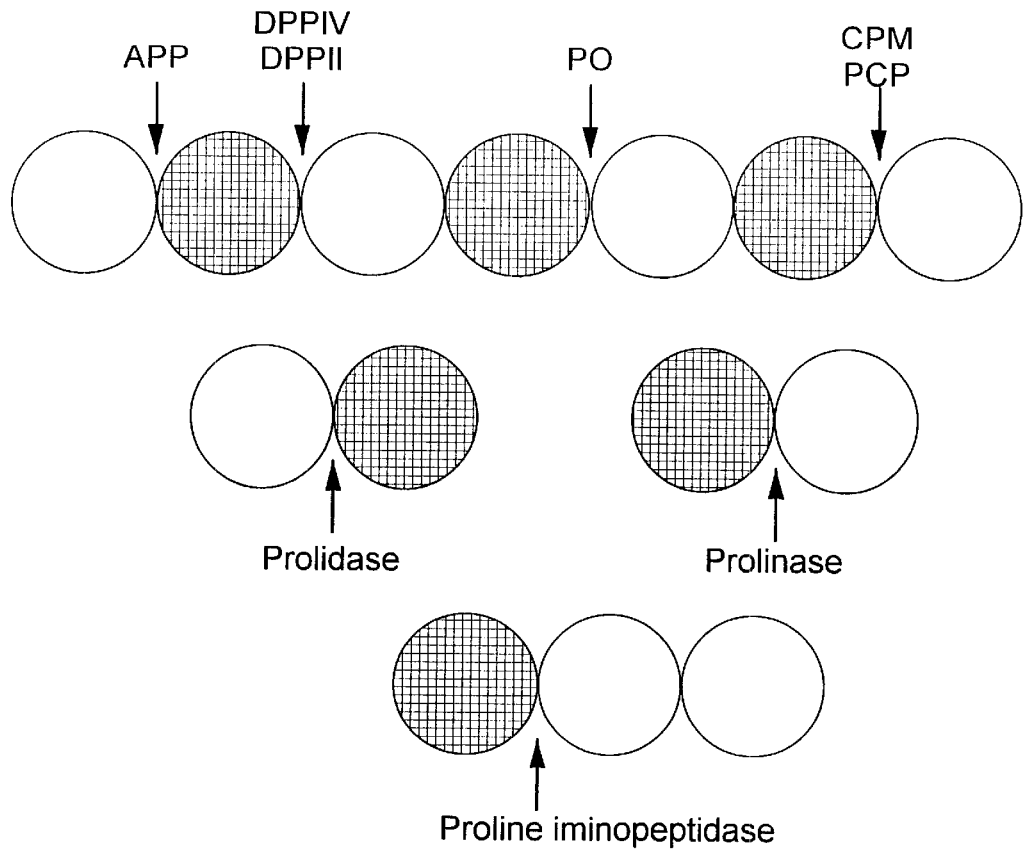

FIGURE 14
PRIOR ART

Versatility of proline specific gateway enzymes. This figure (Cunningham and O'Conner) illustrates that for practically all regulatory situations involving the proline motif (filled circles), there has evolved an enzyme capable of specifically recognizing the position of the proline relative to its neighbors, cleaving either before or after the proline residue in dipeptides, polypeptides and proteins. APP, AminopeptidaseP; DPPIV, dipeptidyl peptidase IV (CD26);DPPII, dipeptidyl peptidase II; PO, prolyl oligopeptidase; CPM, carboxypeptidase M; PCP, prolyl carboxypeptidase (lysosomal).

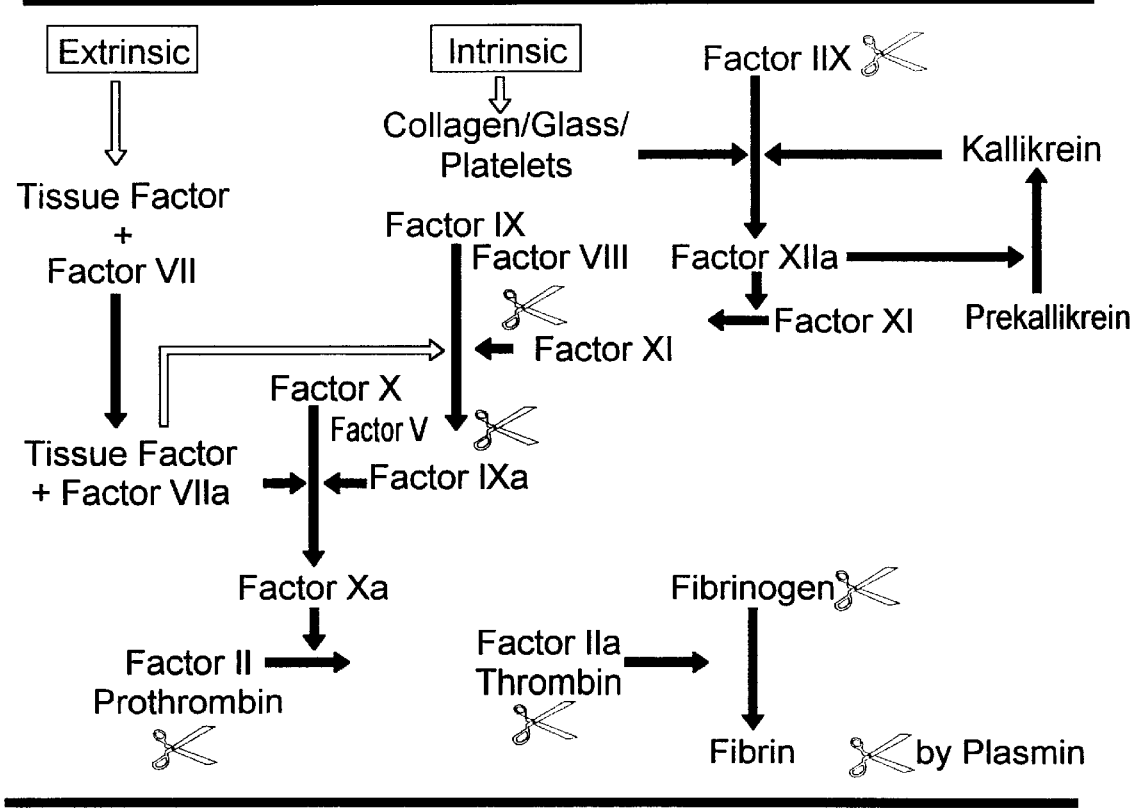

Figure 15
PRIOR ART

The coagulation system, with the intrinsic and extrinsic activation pathways. Under inflammitory conditions, such as sepsis, the disseminated intravascular cascade is modulated by the actions of peptidases, marked as scissors, which otherwise would not participate significantly as regulators under normal conditions for this process. The upregulation of these peptidases during immune system disregulation alters the processing rates of key pro-thrombotic and thrombolytic enzymes including thrombin and plasmin (Levi et al.)

A) PRIOR ART
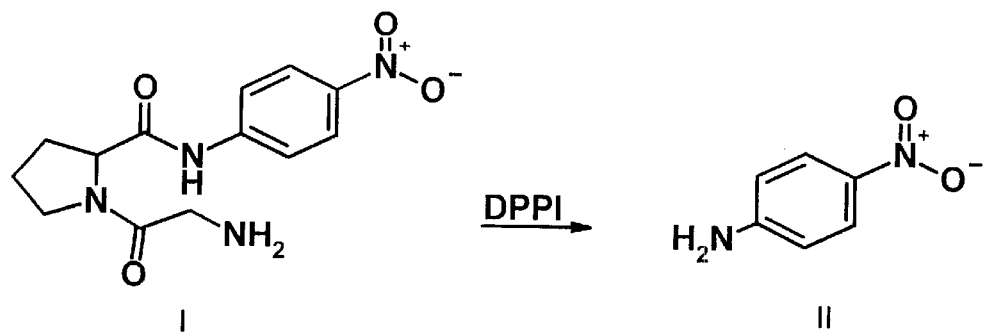
B) METHOD OF THE INVENTION
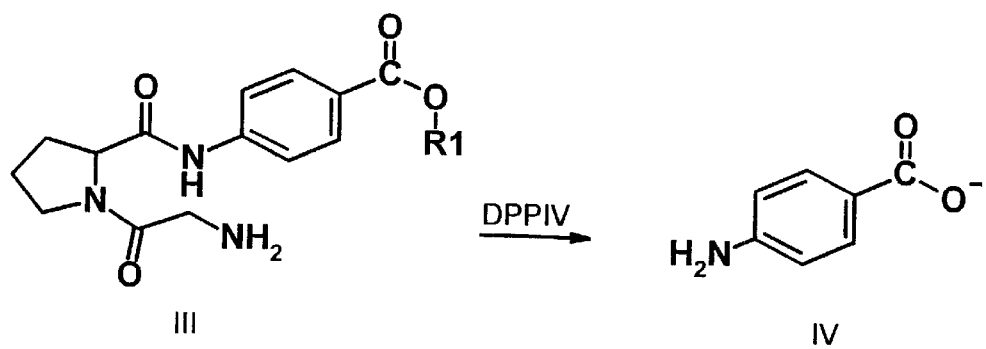
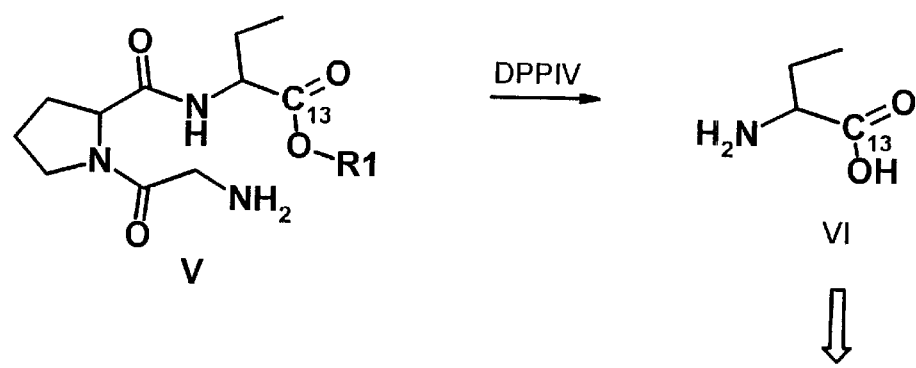
R1 = FUNCTIONAL GROUPS FROM TABLE IV
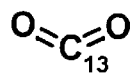
Figure 16
Dipeptidyl Peptidase IV (DPPIV) Metaprobes

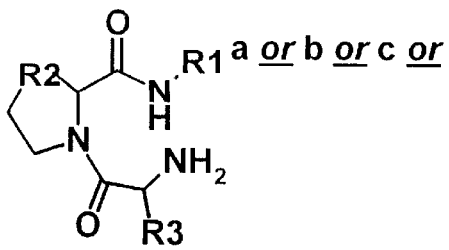

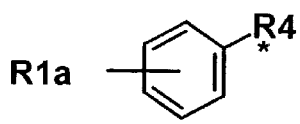

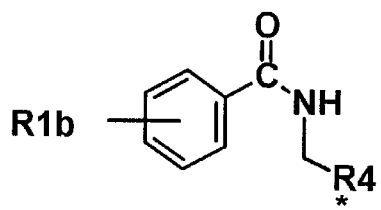

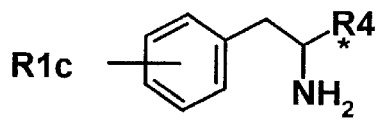

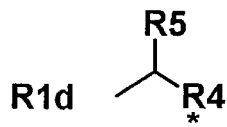

R2 = CH$_{2n}$ (n = 0,1,2); O, N, S

R3, R5 = H, methyl, ethyl, propyl, butyl, pentyl, hexyl, isopropyl, isobutyl, sec-buty tert-butyl, isopentyl, isohexyl, phenyl, phenylmethyl R4 = carboxyl and carboxyl amide functional groups described in Table IV, with characteristic reversible subfunctionalities

* = Preferred position of isotopic release tag in tracer core

Figure 17

Dipeptidyl Peptidase IV (DPPIV) Metaprobes

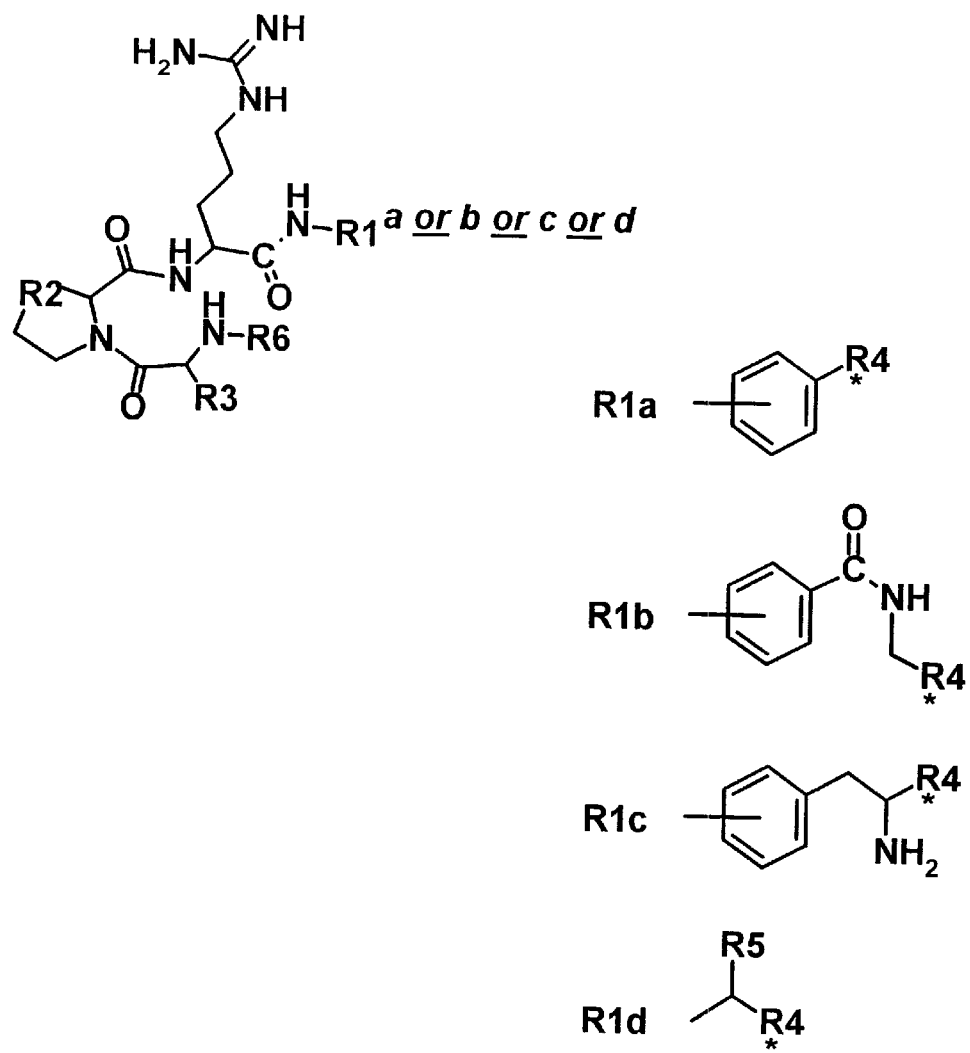

R2 = $CH_{2n}$ n=0,1,2; O, N, S

R3 = benzyl (D or L), isopropyl (L), or unsubstituted

R4 = carboxyl and carboxylamide functional groups described in Table IV, with characteristic reversible subfunctionalities R5 = H, methyl, ethyl, propyl, butyl, pentyl, hexyl, isopropyl, isobutyl, sec-butyl tert-butyl, isopentyl, isohexyl, phenyl, phenylmethyl R6 = acetyl, benzoyl, benzyloxycarbonyl, t-butoxycarbonyl, methoxyacetyl, methoxycarbonyl, pivaloyl

* = Preferred position of isotopic release tag in tracer core

Figure 18
Thrombin Metaprobes

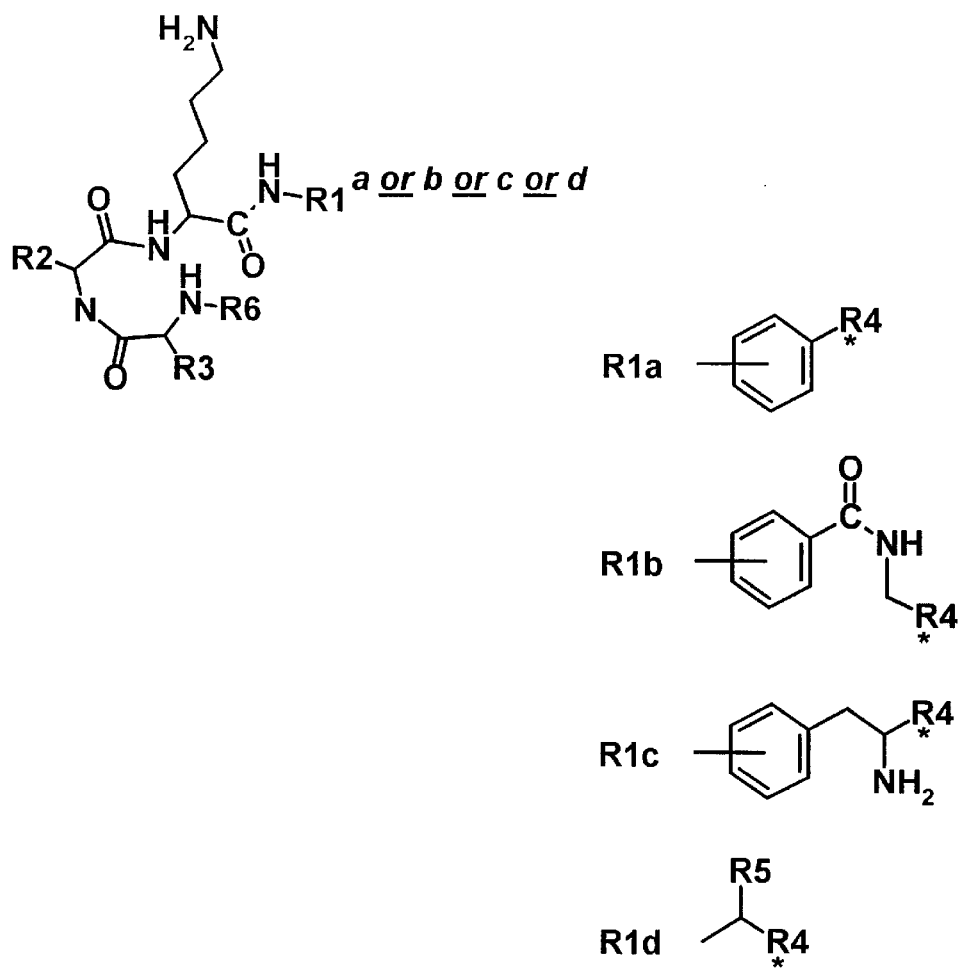

R2 = isopropyl (L), isobutyl (L), sec-butyl (L)

R3 = isopropyl (L), isobutyl (L), sec-butyl (L)

R4 = carboxyl and carboxylamide functional groups described in Table IV, with characteristic reversible subfunctionalities R5 = H, methyl, ethyl, propyl, butyl, pentyl, hexyl, isopropyl, isobutyl, sec-butyl tert-butyl, isopentyl, isohexyl, phenyl, phenylmethyl R6 = acetyl, benzoyl, benzyloxycarbonyl, t-butoxycarbonyl, methoxyacetyl, methoxycarbonyl, pivaloyl

* = Preferred position of isotopic release tag in tracer core

Figure 19
Plasmin Metaprobes

R2 = CH$_{2n}$ n=0,1,2; O, N, S

R3 = glycyl, alanyl, 2-aminobutyryl, valyl, norvalyl, leucyl, norleucyl, isoleucyl, phenylalanyl, methionyl, or other hydrophobic amino acids

* = Preferred position of isotopic release tag in tracer core

Aminopeptidase P Metaprobes

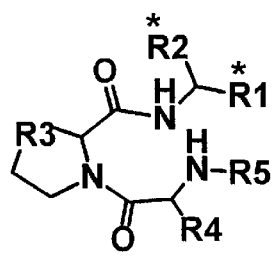

R1 = Carboxyl and carboxylamide functional groups described in Table IV, with characteristic reversible subfunctionalities R2 = H, ethyl, methyl, propyl, butyl, pentyl, hexyl, isopropyl, isobutyl, sec-butyl tert-butyl, isopentyl, isohexyl, phenyl, phenylmethyl R3 = $CH_{2n}$ n=0,1,2; O, N, S R4 = H, ethyl, methyl, ethyl, propyl, butyl, pentyl, hexyl, isopropyl, isobutyl, sec-butyl tert-butyl, isopentyl, isohexyl, phenyl, phenylmethyl R5 = H, formyl, acetyl, benzoyl, benzyloxycarbonyl, t-butoxycarbonyl, hippuryl, isopropoxycarbonyl, methoxyacetyl, methoxycarbonyl, pivaloyl

* = Preferred position of isotopic release tag in tracer core

Figure 21

Prolyl Oligopeptidase Metaprobes

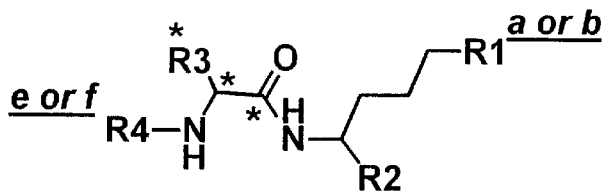

R1a = -CH₂NH₂

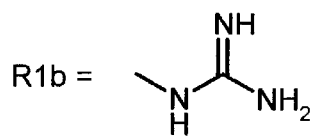

R2 = carboxyl and carboxylamide functional groups described in Table IV, with characteristic reversible subfunctionalities R3 = H, ethyl, methyl, propyl, butyl, pentyl, hexyl, isopropyl, isobutyl, sec-butyl tert-butyl, isopentyl, isohexyl, phenyl, phenylmethyl R4e = H, formyl, acetyl, benzoyl, benzyloxycarbonyl, t-butoxycarbonyl, hippuryl, isopropoxycarbonyl, methoxyacetyl, methoxycarbonyl, pivaloyl

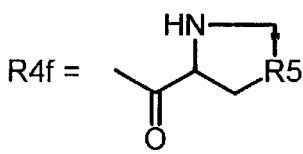

R5 = CH₂ₙ n=0,1,2; O, N, S

* = Preferred position of isotopic release tag in tracer core

Figure 22

Prolyl Oligopeptidase Metaprobes

IN VIVO DETERMINATION OF METABOLIC FUNCTION FOR USE IN THERAPY MANAGEMENT

This application is a 371 of PCT/US99/14725, filed Jun. 29, 1999. This application is a continuation-in-part of U.S. Pat. No. 6,284,219 B1 issued Sep. 4, 2001 (application Ser. No. 09/107,965, filed Jun. 30, 1998), the whole of which is hereby incorporated by reference herein.

STATEMENT REGARDING FEDERALLY SPONSORED RESEARCH OR DEVELOPMENT

Not Applicable

BACKGROUND OF THE INVENTION

The economic and social burden to society of managing a number of costly human medical problems, including digestive disorders, cancer, critical care, infectious diseases, atherosclerosis and neurodegenerative disorders, is severe. Historically, clinicians have tried different ways to assess the status of a patient and monitor the effectiveness of therapy. For example, it has been recognized since antiquity that the monitoring of breath is desirable, as it contains clues to many diseases and metabolic processes in the body.

Breath tests are useful, specifically, as non-invasive procedures for the detection of isotopically labelled tracer substrates, particularly the stable carbon isotope $^{13}C$. Breath test tracer substrates may be given orally, no blood need be drawn and samples may be collected easily.

Historically, tracers have been used in diverse scientific settings to follow the metabolic fate of tracer-labelled molecules in dynamic systems, e.g., to determine rates of synthesis, transformation or degradation of molecules in vivo, in intact organisms or perfused organs, or, with tissue homogenates or subcellular fractions.

The most commonly used tracers are radioactive, e.g., $^{3}H$, $^{14}C$ or $^{32}P$-labelled molecules. These can be "traced" by measuring the intensity and location of the radiation emanating from the tracers as a function of time. Non-radioactive nuclides, or stable isotopes such as $^{13}C$ can also be used advantageously as tracers, especially in metabolic studies. Stable isotope tracers can be "traced" by examining the properties of their molecular mass as it becomes diluted over time by the natural abundance masses also contained within the biological matrix under study in the tracer experiment.

The most frequent approach for using tracers is to incorporate a desired nuclide atom into a target molecule whose transformation is to be studied as a function of time, and then to follow the metabolic fate of the molecule as it undergoes one or more biological interconversions. Another approach, used more in determining properties of enzyme systems, focuses on determining the rate at which the nuclide disappears from the tracer labelled molecule and then reappears after incorporation into biological variants of the initial molecule, e.g., metabolites.

The analysis of nuclide labeling patterns and the quantitation of tracer rates of appearance and disappearance are often time consuming and technically complex operations. For example, while enzymology can be extensively manipulated so as to minimize the confounding effects of biochemical recycling and of metabolic integration on the calculation of pertinent kinetic parameters, far fewer possibilities exist for similar manipulations in vivo.

Another drawback in the historic application of labelled tracer probes is that easy, non-invasive determinations such as breath tests are often not possible, and, as such, invasive methods like biopsy may need to be used. Although breath tests have been shown to be useful in conjunction with determinations of hepatic function and enzyme induction, gastric emptying, maldigestion/malabsorption, and intermediary metabolism, one notable disadvantage or limitation of the breath test for disease diagnosis is that while the labelled end product can be measured, e.g., $^{13}CO_2$, this does not provide information on various pools and fluxes the labelled substrate and its metabolites pass through, in order to give an indication of the presence or absence of a disease condition.

It would, therefore, be beneficial to the art of utilizing tracers in therapy management to systematize and streamline their design and application, especially for the purpose of determining the status of processes critical to the maintenance of normal function in the context of health and disease in vivo, without the drawbacks mentioned above.

SUMMARY OF THE INVENTION

It is an object of the present invention to provide in vivo analytical methods that allow for diagnosis and management of therapy for diseases involving discrete biochemical pathways. In the method of the invention, a labelled tracer probe, a specifically designed substrate of a "gateway" enzyme, an enzyme marking a regulatory point in a discrete biochemical pathway, is administered to a subject; a labelled product of the action of the enzyme is measured; and the appearance and concentration of the product are related to the disease condition of interest. Determination of the rate of substrate-product conversion of the gateway enzyme allows for the analysis to be made. The method involves administering a defined amount of a labelled "metaprobe" substrate of the gateway enzyme to a subject, at a site that provides access to a desired pool of the gateway enzyme in the subject, and measuring the amount of the chosen labelled product. The presence and amount of the chosen labelled product in, e.g., the breath, definitively indicates that the labelled metaprobe has been metabolized by the specific enzyme in the specific biochemical pathway under consideration, and from the calculated rate of substrate-product conversion by the gateway enzyme, the desired diagnostic determination may be made. Likewise, if a specific therapeutic treatment for a disease is underway with a patient, this method allows for a minimally invasive assessment of the effectiveness of the treatment, with minimal discomfort to the patient.

The usefulness of the method of the invention depends on careful determination of the appropriate metaprobe substrate of the selected gateway enzyme. One aspect of such a determination can consist of structurally modifying an enzyme's natural substrate into a surrogate substrate whose metabolism can be measured in vivo in spite of confounding biochemical and physiological circumstances. Another aspect of metaprobe selection is a determination of the most appropriate location of the labelled portion so that the chosen product to be measured is labelled appropriately. Additionally, a further desirable characteristic of a metaprobe is that its enzymatic conversion product be (1) accessible by non-invasive or minimally invasive means, to allow isolation from the biological system containing it, and then be (2) amenable to rapid quantitative analysis for its isotopic content. In other words, the ideal metaprobe should permit clear and rapid differentiation between precursor and product so that calculations of rate of precursor conversion into product, and other rate-dependent parameters, are unambiguous.

In another aspect, the invention relates to labelled metaprobes, and to methods for their synthesis, for use in determination of the rate of in vivo enzyme activity, e.g., of gateway enzymes, such as disclosed herein. A particularly advantageous embodiment comprises a metaprobe having a structure comprising a release tag portion, a core tracer portion, and a derivative complex portion.

BRIEF DESCRIPTION OF THE DRAWINGS

Other features and advantages of the invention will be apparent from the following detailed description of the preferred embodiments thereof and from the claims, taken in conjunction with the accompanying drawings, in which:

FIG. 1b illustrates the superset of gateway enzymes involved in regulation of glutathione homeostasis;

FIG. 3 illustrates gateway enzymes in the homocysteine/methionine cycle;

FIG. 4 illustrates gateway enzymes in the hexosamine-insulin resistance pathway;

FIG. 5 depicts an exemplary set of metaprobes for oxoprolinase;

FIG. 7 depicts an exemplary set of metaprobes for chymotrypsin;

FIG. 8 depicts an exemplary set of metaprobes for γ-glutamyl transferase (GGT);

FIG. 10 depicts an exemplary set of metaprobes for nitric oxide synthsase;

FIG. 11a depicts an exemplary set of metaprobes for cystathionine synthetase (part 1);

FIG. 11b depicts an exemplary set of metaprobes for cystathionine synthetase (part 2);

FIG. 12a depicts an exemplary set of metaprobes for glutamine fructose-6-phosphate amidotransferase (part 1);

FIG. 13 shows the cognitive phase, the covert activation phase and the overt effector phase of cell-signalling leading to pathophysiological symptom presentation in response to tissue injury or antigen presentation;

FIG. 14 shows the versatility of proline specific gateway enzymes in specifically recognizing the position of the proline relative to its neighbors, cleaving either before or after the proline residue in dipeptides, polypeptides and proteins. APP, AminopeptidaseP; DPPIV, dipeptidyl peptidase IV (CD26); DPPII, dipeptidyl peptidase II; PO, prolyl oligopeptidase; CPM, carboxypeptidase M; PCP, prolyl carboxypeptidase (lysosomal) (Cunningham and O'Connor);

FIG. 15 shows the coagulation system, with intrinsic and extrinsic activation pathways;

FIG. 16 shows the use of dipeptidyl peptidase IV (DPPIV) metaprobes in the method of the invention;

FIG. 17 shows the structure of dipeptidyl peptidase IV (DPPIV) metaprobes useful in the method of the invention;

FIG. 18 shows the structure of thrombin metaprobes useful in the method of the invention;

FIG. 19 shows the structure of plasmin metaprobes useful in the method of the invention;

FIG. 21 shows the structure of prolyl oligopeptidases metaprobes useful in the method of the invention; and FIG. 22 shows the structure of carboxypeptidase M metaprobes useful in the method of the invention.

DETAILED DESCRIPTION OF THE INVENTION

Figure 1A:
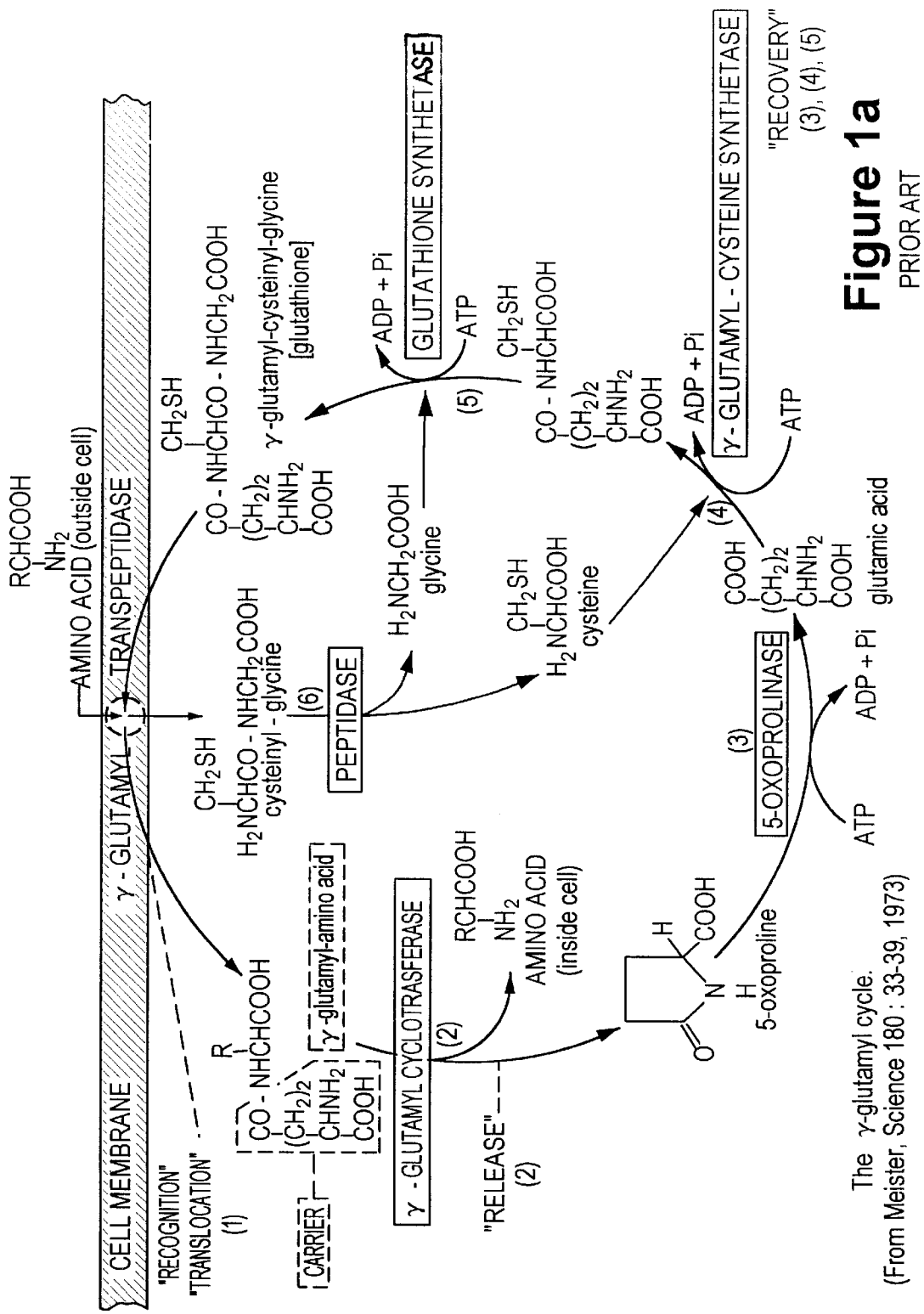
FIG. 1a illustrates gateway enzymes in the γ-glutamyl cycle of the glutathione cytoprotecting system.

The present invention relates to in vivo analytical methods for determining the rate of substrate-product conversion for gateway enzymes important to therapy management, using specially selected, labelled metaprobes, as disclosed herein. The presence or absence of labelled waste product, e.g., $^{13}CO_2$ detected in the breath, following the administration of a chosen metaprobe, can be used to definitively ascertain the presence or absence of a particular condition. The approach disclosed herein addresses the need to obtain rapid, specific and precise information about the precursor-product interconversion rates of "gateway" enzymes, either on a whole-body or organ by organ basis, in mammals and especially in human subjects.

In the living organism, gateway enzymes are components of a dynamic process comprising the biochemical economy of the host. Substrates are converted into products which, in turn, undergo additional conversions by neighboring enzymes within the same tissue structure and/or are translocated to other spatially distinct organ compartments where they are further metabolized over time. Whereas enzyme function is by its very nature isolated and episodic, the circumstance in vivo is precisely the opposite, namely, codependent and continuous. In vivo, enzymes are regenerated and their concentration subject to fluctuation. Nor are their precursor-product concentrations predictable, owing to endogenous substrate cycling, or controllable by exogenous addition or removal.

"Gateway enzymes", as used herein, refer to enzymes representing regulatory points that are 1) homeostatic (they preserve a biochemical status quo), or 2) allostatic (they permit adaptation and survival under conditions of rapid biochemical change and stress.) In terms of genetic regulation, the former tend to be constitutive enzymes, while the latter are more likely to be inducible. In either case, gateway enzymes provide functional site(s) at which the throughput of substrates and/or their metabolites can be quantitatively monitored for establishing normative values under homeostatic conditions and extreme tolerances under allostatic conditions.

For purposes of the present disclosure, gateway enzymes may be classified into one or more of the following categories:

Class I: An entry into a discrete biochemical pathway that is the starting point for a cascade of biochemical events;

Class II: A "bottleneck" or "constriction" within a discrete biochemical pathway which regulates the unidirectional and irreversible conversion of precursor substrate into product; or Class III: A "floodgate" within a biochemical pathway which is inducible in response to traumatic or catastrophic pathophysiological events.

Class I gateway enzymes generally function as mediators of absorption and transport, and are taken from the general families of membrane-bound enzymes in the walls of the digestive tract, of secretory and excretory organs, of circulatory vessels, and of cells and organelles associated with energy production or xenobiotic detoxification.

Class II gateway enzymes may be identified as the causative agents in "in-born" errors of metabolism or endocrine dysregulation. These diseases are mediated by extreme cases of bottlenecks caused by genetic deficits in the gateway enzyme's ability to function properly, with the overt result that its substrate accumulates in toxic proportions. These bottlenecks are defined functionally, for example, in terms of great disparities in the Michaelis-Menten constants ($K_m$) between the gateway enzyme and its nearest neighbors. Most pathophysiological conditions are known to emulate one or more of these metabolic aberrations. It follows that most of the gateway enzymes responsible for genetic metabolic abnormalities or endocrine dysregulation are the same ones that can be probed for aberrant function under disease conditions.

Class III gateway enzymes include those whose metabolic products become manifested during acute conditions of oxidant stress; or chemokine and lymphokine mediated acute phase responses to trauma, sepsis, or viral load; or insult by cytostatic drugs or immunosuppressive agents.

Non-limiting examples of gateway enzymes, grouped by the classes defined above, are set forth below in Tables 1, 2 and 3, including a description of their normal physiological role, and their diagnostic significance in the assessment of pathophysiological conditions. It should be noted that more than one classification may apply to any given gateway enzyme. For example, an enzyme that serves as a pathway "entry" (i.e., Class I) under normal or homeostatic conditions may be found to respond to inductive stimuli under allostatic or pathophysiological conditions, thereby becoming a "floodgate" (Class III); and vice versa.

TABLE 1

Class I Gateway Enzymes

Aminopeptidase A

Cleaves N-terminal glutamyl and aspartyl residues from regulatory peptides that act on pre-B or stromal cells, thereby activating the progression along the B-cell maturation pathway of the hematopoetic system. This enzyme also participates in the angiotensin regulatory cycle, by converting angiotensin II into Angiotensin III, the initiating step in angiotensin degradation and initiates the processing on interleukin 7 and interleukin 7 receptor. It is known to be a cell surface glycoprotein and the immunoreactive differentiation antigen BP-1/6C3. This enzyme is also known as glutamyl aminopeptidase (EAP, GAP, EC 3.4.11.7) as is also abundantly expressed on the brush border of intestinal enterocytes, where it facilittates entry of glutamic and aspartic acid into the splachnic circulation.

Aminopeptidase N

Cleaves N-terminal alanine , phenylalanine, tyrosine and leucine from regulatory peptides, in the binding of viruses and in tumor invasion. It is upregulated during mitogenic stimulation of peripheral T-cells and participates in the initiation of cell signalling between myeloid progenitors, monocytes, granulocytes and myeloid cells. It is a membrane bound protein, synonymous with the CD13 differentiating antigen, which also initiates the degradation of two prominent inflammatory mediators, enkephalins and the chemotactic cytokine IL-8. This enzyme is also known as membrane alanyl aminopeptidase, EC 3.4.11.2.

Aminopeptidase P

Cleaves N-terminal aminoacids, especially, arginine from peptides with proline in the penultimate or ante-penultimate position, provided that it is a hydrophobic or basic residue. It is both a cytosolic and an ecto-enzyme that initiates the processing of reactives peptides, such as bradykinin, C-reactive protein, kentcin, morphiceptin, oxytocin, and substance-P. In the enterocyte, and at the brush border membrane of the gut, it is the principal hydrolytic enzyme to initiate hydrolysis of proline rich peptides by nicking off these otherwise unhydrolizable (by TABLE 1-continued Class I Gateway Enzymes digestive serine enzymes) residues adjacent to a penultimate proline and thereby exposing the resulting peptide to further degradation by N-terminal specific proline peptidases. This enzyme is also known as X-Pro-aminopeptidase, EC 3.4.11.9, and is a zinc metalloprotease.

Arginase

Principal modulator of urea production and the turnover of ureotelic pools. This enzyme regulates the fate of arginine and the substrate availability for the synthesis of creatine and polyamines. It provides the entry point into the urea cycle and related nitrogen excretory pathways. Under pathophysiological conditions, arginase is the gateway enzyme in the catabolic cascade controlling nitrogen loss during trauma and sepsis (Class III) . Arginase is also the gateway for urea production, and subsequent consumption, by intraluminal pathogenic bacteria during infection of the upper GI tract and lungs, a process that can become uncontrollable except by therapeutic intervention.

Chymotrypsin

Initiates hydrolysis of aromatic amino acid peptides in proteins; specific pancreatic enzyme so serves as an indicator of normal pancreatic function.

Cystathionine synthase

Initiates the first step in the transfer of sulfur from methionine into cysteine and is the principal non-folate dependent mechanism for clearance of homocysteine, which is known to be a causative agent in cardiovascular disease. When homocysteine remethylation becomes saturated or inhibited under pathophysiological conditions, the cystathionine synthase then functions as the bottleneck (Class II) in this detoxifying pathway. It also becomes a bottleneck in the conversion of serine to cysteine, the latter an indispensible amino acid for immune system function.

Dipeptidyl Peptidase II

A broadly distributed lysosomal peptidase, it is intimately, and primarily, associated with bone and surrounding connective tissues, including osteocytes, osteoblasts, chondrocytes, chondroblasts, fibroblasts and macraphages. Osteoclasts in the resting zone of the bone growth plate are a particularly rich source of this enzyme, which serves as the primary processing site for proline rich peptide and peptide fragments requisite for bone cell differentiation and growth. The enzyme is classified as EC 3.4.14.2.

y-Glutamyl transpeptidase

Membrane-bound transporter of glutamyl residues; mediates entry of glutathione into cells of the digestive tract. Activity becomes abnormal in cancer and immunosuppression (Class III) and becomes limiting under conditions of septic insult (Class II).

Glutathione-S-transferase

Initiates metabolism of xenobiotics by conjugation. Activity becomes abnormal in response to xenobiotic load, especially by cytostatic drugs (Class III) or becomes limiting under immunosuppression (Class II); serves as an indicator of antioxidant status.

Palmitoyl transferase

Membrane bound translocator of fatty acids, initiates metabolism of serine and carnitine esters in the production cascade of complex membrane lipids. Becomes a limiting gateway (Class II) in diabetes and kidney disease.

Phospholipase-A2

Initiates first steps in the cascade of phospholipid metabolism. Becomes limiting in pancreatic and neurological disorders that are consequent to changes in neuronal cell membrane repair (Class II); uncontrolled activity of the extracellular forms (Class III) becomes an allostatic factor in inflammatory disease.

Prolyl carboxypeptidase

Cleaves C-terminal aromatic and aliphatic amino acids from peptides with proline as the preceding residue. It is found in leucocytes. macrophages and synovial fluid where it mediates the degradation and resorbtion of collagen. This latter function is accelerated as part of the inflammatory response, in which the enzyme serves a homeostatic role by reprocessing collagen fragments. It is also known as lysosomal Pro-X carboxypeptidase, EC 3.4.16.2.

TABLE 1-continued

Class I Gateway Enzymes

Prolyl oligopeptidase

Originally designated as a post-proline cleaving enzyme or proline specific endopeptidase, this enzyme is an intracellular peptidase which specifically hydrolyzes peptide bonds at the carboxyl side of proline, and more slowly, of alanine residues. Prolyl oligopeptidase is the only enzyme which cleaves prolyl residues within a peptide sequence and therefore is the primary effector in the initiation of soluble collagen fragment metabolism, from dietary origin or after the initial action of matrix collagenases. It also initiates the normal catabolic sequence in the turnover of proline-rich neuropeptides, including bradykinin and neurotensin, and in the processing of amyloid proteins, whose disregulation is believed to lead to Alzheimer's disease. The enzyme is also known as proline endopeptidase, EC 3.4.21.26.

Trypsin (Pancreatic)

Initiates activation of all zymogens prior to digestion. Becomes limiting (Class II) in pancreatic disease.

TABLE 2

Class IT Gateway Enzymes

Alanine-glyoxylate aminotransferase

Regulates glyoxylate clearance in the liver. Limiting when liver peroxisomal enzymes become overloaded by oxidant stress.

Elastase

Regulates the metabolism of elastin but also initiates metabolism of lipophilic (aliphatic amino acid rich) peptides during digestion (Class I) Becomes limiting in pancreatic disease and in neurological conditions attributable to impaired clearance of elastin in tissues and cells, such as neutrophils, in cystic fibrosis.

Glutamine-fructose-6-phosphate aminotransferase

Rate limiting enzyme in hexosamine synthesis; enzyme system capacity forecasts insulin resistance.

α-Ketoacid decarboxylase (mitochondrial)

Regulates disposal of toxic products of amino acid transaminations and participates in homeostatic mechanism for liver and kidney function. Activity varies widely under pathophysiological conditions triggered by diabetes and alcoholism and, therefore, becomes an indicator of severity and risk.

Liver N-acetyl transferase (Nat1)

Limiting pathway for monomorphic substrate clearance by acetylation. Becomes suppressed under conditions of multiple drug toxicity, especially when HIV positive individual become symptomatic.

Microsomal oxidase (P450 dependent)

Regulates disposal of xenobiotics by hydroxylation. Activity is inducible in response to toxic load (Class III) but also can be suppressed by multiple drug interactions and hepatotoxic agents.

Oxoprolinase

Principal constitutive enzyme of the y-glutamyl cycle and regulates the recycling of glutamyl residues via clearance of oxoproline. Activity becomes limiting in trauma and sepsis or during conditions of rapid glutathione synthesis. Serves as a marker for glutathione and, therefore, for cell cytoprotection capacity.

Plasmin

The principal thrombolytic enzyme in the coagulation cascade, plasmin is a trypsin like enzyme whose major physiological substrates are fibrinogen and fibrin, where it catalyzes the cleavage of lysyl and arginyl residues at their carboxyl terminus. It is in this capacity that it serves as a regulatory bottleneck under normal physiologic conditions. Plasmin also functions in the conversion of latent cell associated transforming growth factor beta to its active form and thereby becomes a mediator of the inflammatory response. In addition plasmin plays a major regulatory role in pro-enzyme conversions, globulin catabolism and alternate complement pathways in the contact phase of coagulation. Its EC classification is 3.4.21.7

TABLE 2-continued

Class IT Gateway Enzymes

Prolidase

A cytosolic exopeptidase, the enzyme is closely related to aminopeptidase P in that it also removes N-terminal amino acids from substrates with proline in the penultimate position, yet it is manifestly dipeptide specific. The primary biological, and homeostatic function of prolidase, is the metabolism of collagen derived peptides, with the subsequent recycling of proline. Prolidase deficiency results in an inability to recycle proline from dipeptides of either cellular or dietary origin and leads to abnormalities of the skin and other collagenous tissues, of particular importance in fetal maturation and brain development. The enzyme is also known as X-Pro dipeptidase, EC 3.4.13.9.

Prolinase

Serves the same function as prolidase, but with the inverse order of proline specificity in so far as it cleaves N-terminal proline, also exclusively from dipeptides. Its primary function is to mediate catabolism and recycling of collagen after its primary digestion by lysosomal enzymes. It is particularly prevalent in kidney and in fibroblasts. The enzyme is known as Pro-X dipeptidase, EC 3.4.13.8.

Pyroglutamyl peptidase

This is the only known omega peptidase which specifically removes the pyroglutamyl (pGlu) N-terminus from regulatory peptides and proteins, as a signaling mechanism for the action of other peptidases which cannot recognize the pGlu residue. It exists as both a membrane bound metalloenzyme and a serum enzyme, whose primary homeostatic function is to activate thyrotropin releasing hormone and other hypothalamic hypophysiotropic neuropeptides, such as neurotensin and bombesin, by removing their pGlu N-terminal cap. In concert with oxoprolinase, pyroglutamyl peptidase is involved in the regulation of the cellular pool of free pyroglutamic acid (oxoproline), a component substrate of the glutathione cycle. The enzyme is also known as pyroglutamyl aminopeptidas, EC 3.4.19.3.

Thrombin

The last enzyme in the coagulation cascade, thrombin is the only mammalian protease capable of clotting fibrinogen, and therefore is the primary target for regulation by a complex sequence of zymogen activation and inhibition steps. In addition to its activity on the soluble components of the coagulation cascade, thrombin also induces physiologic responses from a variety of cells. It causes platelets to aggregate, provides mitogenic stimuli to a hemopoietic cells, and modulates neurite growth through a G-protein coupled receptor that thrombin activates by a unique mechanism. Its EC classification is 3.4.21.5.

Sulfite oxidase

Limiting enzyme for the clearance of sulfur oxides that are by-products of oxidant stress in liver heart and kidney. Indicator of homeostatic capacity under normal conditions and allostatic capacity when pathophysiological conditions are suspected.

TABLE 3

Class III Gateway Enzymes

Angiotensin converting enzyme

Uncontrolled production leads to hypertension and cardiovascular disease. Activity is an indicator for efficacy of therapeutic intervention.

Carboxypeptidase M

This lymphoid ecto-enzyme is also the MAX.1/2 macrophage differentiation antigen, with a prevalence in lung tissue. Its function in the mediation of cellular immunity under normal conditions involves peptide hormone processing but also contributes to the pathology of inflammation by altering the specificity of kinins and their receptor agonists, mainly in the kidney. Anaphylatoxin, epiderminal growth factor, nerve growth factor, amphiregulin, and macrophage stimulating hormone are also regulated by C- terminal clipping of arginine or lysine. Its EC classification is 3.4.17.12

TABLE 3-continued

Class III Gateway Enzymes

Dipeptidyl Peptidase IV

A serine protease that releases dipeptides from the N-terminus when the penultimate residue is proline or alanine. DPPIV is involved in the processing of neuropeptides, lymphokines and chemokines. On the T-cell surface it has proven to be identical with the CD26 differentiation antigen, and its expression is increased with that of other activation markers and in response to pro-inflammatory cytokines. The soluble CD26 molecule in plasma is a potent T-cell co-stimulator which plays a defining role in lymphocyte activation and differentiation into of naive T-cells into the CD4+/Th-1 subset that actively secretes interleukin-2 and initiates the interferon response to cellular antigens. Its enzyme classification is EC 3.4.14.5.

Human HIV protease

Mediates proliferation of HIV viral load. Becomes resistant to protease inhibitors and, therefore, can be used to gauge the efficacy and extent of therapeutic intervention.

Neutral endopeptidase

Originally identified as the common acute lymphoblastic leukemia antigen, this cell surface ectopeptidase is identical to the CD10 differentiation antigen. On neutrophils it plays a role in the activation of chemotaxis via the hydrolytic activation of cell signaling peptides, such as substance-P, enkephalins, tachychinins, and atrial natriuretic peptide and its expression is up-regulated in step with the progression of the systemic inflammatory response in relation to acute injury, such as in adult respiratory distress syndrome or end-stage renal failure. The enzyme is also known as neprilysin, EC 3.4.24.11

Nitric oxide synthase

Principal modulator of free radical and NO mediated cell signaling. Triggers acute chemokine and lymphokine responses; becomes uncontrollable during trauma and sepsis, then triggers fatal multiple organ system failure; implicated in acute disorders such as preeclampsia and chronic disorders such as vascular disease.

Peroxysomal peroxidase

Principal modulator of oxygen free radical biochemistry and a principal effector of the lipid peroxydation cascade. Indicator for high risk of cardiovascular and diabetic disorders and of severity of inflammation.

Operationally, the major obstacle to the implementation of diagnostic tracer studies on gateway enzyme function is the analytical burden of quantitating the precursor product relationship. The product of the enzymatic transformation must be differentiated from the precursor, before it itself undergoes subsequent and further metabolism, or is resynthesized via common reversible pathways into another copy of the precursor molecule from which it originated. As such, an important aspect of the present disclosure relates to the "direct" determination of metabolites of the labelled substrate.

"Direct" determination is possible if the product to be detected, i.e., the product bearing the traced label, is carefully chosen. For example, the detected product metabolite must be released at the time of action of the gateway enzyme or immediately metabolized from the released products. The product must be immediately detectable externally to the patient or else the product must be stable and temporarily captured, e.g., absorbed by a body tissue where it is not further metabolized or sequestered as a stable conjugate intended for excretion, and remain capable of later detection. The preferred forms of tracer-bearing metabolic products for the purpose of direct detection are small water soluble molecules such as ammonia, bicarbonate, urea, nitrate, as well all the larger molecules that are rapidly converted into them bu. either biochemical processes in vivo or by microchemical manipulation ex vivo. Thus, the class of preferred metabolites also includes acetate, butyrate, formate, propionate, and related small chain aliphatic, 2-amino, guanidino, 2- or 3-hydroxy-, 2- or 3-keto-acids, methanol, ethanol and urea.

Therefore, a further aspect of the invention relates to labelled metaprobes which allow for such "direct" determination, permitting clear and rapid differentiation between precursor and product so that calculations of rate and other rate-dependent parameters, of precursor conversion into product are based on irreversible and unidirectional enzymatic transformation. The labelled metabolites/ enzymatic conversion products are accessible by non-invasive or minimally invasive means, such as breath tests, and are amenable to rapid quantitative analysis for their isotopic content.

The term "metaprobe" as used herein is meant to refer to a compound that can act as a substrate for a gateway enzyme or enzymes and that, when administered to a patient in vivo, is acted upon by that enzyme so as to produce at least one labelled "end product" that is not processed further by the subject's normally available biochemical systems. Typically, this means 1) that the labelled end product is a usual waste byproduct of the subject organism, which proceeds directly to excretion or, alternatively, finds its way to a location of the organism where it may reside until excretion, e.g., in fatty tissue or gall bladder; in sweat, tear or salivary gland; in kidney or colon; or 2) that immediately after the metaprobe is acted upon by the gateway enzyme, the labelled portion of the product is immediately converted into a (labelled) waste byproduct and is directly excreted, or, alternatively stored for a time as described above. Once the product is excreted, a "direct" determination of the gateway enzyme activity may be carried out by measuring the isotopic concentration in the waste stream, e.g., $^{13}CO_2$ in the breath, bicarbonate ions in plasma or $^{15}N$-urea in urine, so as to generate an impulse response curve.

The specific structure of the metaprobe will of course be dependent on, inter alia, an understanding of the particular gateway enzyme structure and substrate chemistry, the desired labeling isotope, and the biochemical pathway(s) of interest. An ideal metaprobe will consist of three components, although any two may be combined into a single, but bifunctional molecular entity: 1) a release tag; 2) a core tracer component or moiety; and 3) a derivative complex component or moiety. The "release tag" as a component of the metaprobe is the unique identifier. The "core tracer" constituent of the metaprobe is that portion of the molecule that is acted upon to trace the biochemical process under investigation. The derivative complex is the chemical "packaging" or structural "cloaking" that permits the core tracer to withstand its journey through incidental biochemical pathways on route to its point of delivery, the desired gateway enzyme.

The release tag component of a metaprobe may include the following: 1) A functional group labelled with a stable (non-radioactive) nuclide of, preferably, carbon, hydrogen, nitrogen, oxygen, or sulfur; however, any other radioactive or stable nuclide whose abundance in living organisms is approximately 5% or less by weight of elemental composition may be used. 2) A functional group selected from the group consisting of $C_1$ to $C_3$ moieties of molecular weight less than 100 Daltons that are $^{13}C$ or other isotopic carbon-labelled derivatives of carboxylic acid, aldehyde, nitrile, aldimine, formamido, acetamido, propionamido, methoxy, ethoxy, propoxy, formyloxy, acetoxy, propionoxy, acetamidino, and formamidino, guanido, guanidino, and ureido functional groups that a) when oxidized enzymatically, result in labelled isotopic carbon-containing carbon monoxide, carbon dioxide, formic acid, acetic acid, acetone, acetaldehyde, propionaldehyde, propionic acid, cyanide, formamide, acetamide, or urea; or b) when chemically oxidized, thermolytically or thermochemolytically treated, result in labelled carbon monoxide, carbon dioxide, methane, ethane, propane, acetone, acetaldehyde, propionaldehyde, cyanide radicals, hydrogen cyanide, cyanate radicals, hydrogen cyanate, formic acid, acetic acid, propionic acid, formamide, or cyanamide. 3) A functional group selected from the group consisting of $C_1$ to $C_3$ moieties of molecular weight less than 100 Daltons that are $^{15}N$ or other isotopic nitrogen-labelled derivatives of nitrile, aldimine, formamido, acetamido, acetamidino, and formamidino, guanido, guanidino, and ureido functional groups that a) when oxidized enzymatically, result in isotopic nitrogen-containing nitrogen gas, nitric oxide, nitrite anion, nitrate anion, ammonia, cyanide, formamide, acetamide, or urea; or b) when chemically oxidized, thermolytically or thermochemolytically treated, result in labelled nitrogen gas, nitric oxide, nitrous oxide, cyanide radicals, hydrogen cyanide, cyanate radicals, hydrogen cyanate, formamide, formamidine, or cyanamide. 4) A functional group selected from the group consisting of $C_1$ to $C_3$ moieties of molecular weight less than 100 Daltons that are $^{18}O$ or other isotopic oxygen-labelled derivatives of carboxylic acid, aldehyde, formamido, acetamido, methoxy, ethoxy, formyloxy, acetoxy, formamidino, guanido, and ureido functional groups that a) when oxidized enzymatically, result in isotopic-labelled oxygen-containing carbon monoxide, carbon dioxide, formic acid, acetic acid, propionic acid, acetone, acetaldehyde, propionaldehyde, formamide, acetamide, or urea; or b) when chemically oxidized, thermolytically or thermochemolytically treated, result in labelled carbon monoxide, carbon dioxide, cyanate radicals, hydrogen cyanate, formic acid, acetic acid, propionic acid, or formamide. 5) A functional group selected from the group consisting of $C_1$ to $C_3$ moieties of molecular weight less than 100 Daltons that are $^{34}S$ or other isotopic sulfur-labelled sulfur analogs of the carbonyl, hydroxy or other oxygen functionality-containing functional groups listed above.

The core tracer may be defined as a functionalized $C_2$ or greater alkyl or aralkyl hydrocarbon moieties having one or more modifiable groups, at least one of which comprises the release tag as a discrete substituent at either a terminus of the moiety (as opposed to embedded within the backbone of the chain or ring) or at both ends, the preferred embodiments consisting of 2-amino-aliphatic acids. In the case of core tracers whose pendant release tags are intended for removal by non-enzymatic means, the preferred embodiments consist of a) molecules that are not natural biosynthetic products of mammals or b) molecules that are not metabolized by mammals or c) those 2-amino-aliphatic acids that are not found in mammalian proteins, although they may be biosynthesized and metabolized. The preferred modifiable groups are shown in Table 4, below.

TABLE IV

REVERSIBLE GROUPS

| Modifiable group | $R^a$ | Reversible group | $Z^a$ |
|---|---|---|---|
| RC=O | H, Ak, Ar | RC(OZ)$_2$ | Ak |
|  | H | HC(O$_2$CZ)$_2$ | Ak, Ar |
|  | H, Ak, Ar | C=C—OZ | Ak |
|  | H, Ak, Ar | C=C—NZ$^1$Z$^2$ | Ak |
|  | H | CHCl(O$_2$CZ) | Ak, Ar |
|  | H, Ak, Ar | C=NZ | Ak, Ar, OMe |
|  | H, Ak, Ar | (thiazolidine ring structure) | H, CO$_2$Ak |
| CO$_2$H | H, Ak, Ar | C=C—O$_2$CZ | Ak, Ar |
|  | — | CO$_2$Z | Ak, Ar |
|  | — | C=O(SZ) | Ak, Ar |
|  | — | C=O(NZ$^1$Z$^2$) | H, Ak, Ar, OH, NH$_2$ |
|  | — | CO$_2$CHZ$^1$O$_2$CZ$^2$ | Z$^1$ = H, Ph; Z$^2$ = Ak, Ar |
|  | — | CO$_2$CHZCl | H, Ar |
|  | — | C(OZ)$_3$ | Ak |
|  | — | CO$_2$CO$_2$Z | Ak, Ar |
|  | — | CO$_2$CH$_2$Z | SMe, SOMe, SO$_2$Me |
| CONHR | H | CONHCH$_2$NZ$^1$Z$^2$ | Ak, Ar |
|  | H | CONHCH$_2$OH | — |
| OH | — | O$_2$CZ | Ak, Ar, . . . |
|  | — | (—O)$_3$CZ | Ak, Ar, . . . |
|  | — | OZ | Ak, Ar |
|  | — | —O—C=C | — |
|  | — | (—O—)$_2$CZ$^1$Z$^2$ | H, Ak, Ar |
|  | — | O$_2$CNZ$^1$Z$^2$ | H, Ak, Ar |
|  | — | O$_2$COZ | H, Ak, Ar |
|  | — | O$_2$CO$_2$CZ | H, Ak, Ar |
|  | — | OSiZ$_1$ | Ak |
|  | — | (—O)$_2$CO | — |
|  | — | (—O)$_3$PO | — |
|  | — | (—O)$_2$SO$_2$ | — |
| NHR | H, Ak, Ar | NR(C=O)Z | Ak, Ar |
|  | H, Ak, Ar | NRCO$_2$Z | Ak, Ar |
|  | H, Ak, Ar | NRC=C | — |
|  | H, Ak, Ar | NR(C=O)NHZ | Ak, Ar |
|  | Ar | NArCH$_2$N(succinimide) | — |
| —NH | — | —N—CH$_2$O$_2$CH | Ak, Ar |
| SH | — | S(C=O)Z | Ak, Ar |

$^a$Ak, Alkyl; Ar, aryl.

The derivative complex may be characterized as one or more reversible derivative groups, also taken from the list in Table 4, which may be attached to the tracer core either at the site of the release tag, or elsewhere along the carbon skeleton of the core. The purpose of the derivative complex is to impart the necessary steric, affinity and other physicochemical properties to permit the entire metaprobe to function as a substrate for the intended gateway enzyme. The derivative complex also serves to modulate the solubility, lipophilicity, partition coefficient, and diffusional properties of the metaprobe so as to facilitate transport and delivery to the site of metabolism. The derivative complex desirably includes a) those groups that are resistant to uncatalyzed aqueous solvolysis under physiological conditions but b) are rapidly hydrolyzed by non-specific esterases and peptidases found in biological fluids and c) that impart to the metaprobe a partition coefficient, such as the octanol/water Log$_p$ value, in the range of +1 to +4 and falling within ±25% of the corresponding values for any of the natural substrates known to be metabolized by the gateway enzyme.

A final preferred embodiment of the metaprobe design are those combinations of release tag, core tracer and derivative complex that taken as a whole permit the metaprobe to be metabolized by its gateway enzyme in measurable amounts within 2 hours of its introduction into the host organism under study. More detailed teachings as to metaprobe design criteria can be summarized in terms of several rubrics that, if followed, will yield metaprobes of demonstrable utility. The design of any metaprobe must be biologically sound and concordant with the biochemical and physico-chemical relationships of the biological system that they are targeted towards. In practical, terms, as to biological properties, the tracer core and carrier complex moieties of a metaprobe must be sufficiently soluble in biological fluids so as to be transported either by passive diffusion or by facilitated biophysical processes. Their molecular structures, therefore, should not include functional groups that can be predicted to facilitate crystallization, flocculation or polymerization in the lumen of the digestive tract or within the circulatory, respiratory or genitourinary systems.

The entire metaprobe, and each of its component parts should display no detectable activity when assayed as a biological reponse modifier, hormone, toxicant or xenobiotic, or acute toxicity in standard toxicological safety assays, either in vivo or in surrogate systems, should fall above doses in excess of 2000 mg/kg. Nor should metaprobes incorporate any components contributing to detectable pyrogenicity or endotoxin reactivity. Therefore, metaprobes should be constructed with chemical likages and functionalities that render the molecule amenable to sterilization when in solution, eiher by heat (autoclaving), irradiation or ultrafiltration. Furthermore, metaprobes should be both compatible with and non-reactive toward common food additives, excipients and inert ingredients that are generally found in over-the-counter pharmaceuticals, cosmetics and other formulated personal care products that are designed for ingestion or topical application.

In terms of their extended chemical properties, the molecular relationships between and among release tag, core tracer and carrier complex must be harmonized so that the properties of one do not interfere with the proper function of the others. For example, in the selection process for enzymatically hydrolyzeable release tags, such as carbonyl, formyl, acetyl, propionyl, or for heteroalkyl release tags amenable to oxidative removal, such as O-, N-, S-methylated or ethylated species, the metaprobe designer must chose all other substituents within the core tracer, including those required to form the derivative complex, in such a way as to minimize the steric and electronic effects which might inhibit the rapid removal of the release tag.

The selection of substituents and the configuration of linkages between component parts of a metaprobe, whose analysis is dependent on release tag removal by non-enzymatic means (e.g., thermolysis, pyrolysis, photoactivation, catalytic cleavage, destructive oxidation or chemical sequestration) should be tailored so that the fractional rate of release tag removal and its isotopic enrichment are not compromised. In other words, in the course of optimizing metaprobe design, it is necessary to model the structural properties of the core tracer-release tag-carrier complex combined motif so that the introduction of substituents onto any given part of a metaprobe do not militate, by means of steric or electronic interactions, against the affinity of the metaprobe towards the gateway enzyme domain that it is intended to probe. Further, the design of the metaprobe's constituent parts should not impair the reactivity of the release tag towards enzymatic or physico-chemical removal.

Both these classes of metaprobe design optimization requirements can be addressed by skilled practitioners of organic chemical discovery through the use of QSAR and related forms of a priori molecular property analysis. Procedures for doing so are readily available within the corpus of traditional methods for chemical discovery (Topliss, 1983) or in the contemporary context of combinatorial chemistry design and chemical informatics. Chemical property prediction software is readily available commercially, as exemplified by I-LAB and QSPR (Acdlabs, Inc.) and the PALLAS modules (Compudrug, Inc.). These software packages may be used as standalone applications for metaprobe design and can also be augmented by incorporating published rubrics for functional group and "prodrug" lability (Charton, 1985; Hansch, 1972). These expert systems can afford the requisite and indispensible design information about any proposed metaprobe with respect to its putative acidity/basicity, partition coefficient, distribution coefficient, metabolic inactivation, chemical lability, toxicity, stereochemistry and reactivity. By comparing and contrasting these types of physical characteristics with those of known gateway enzyme substrates, the construction of analogous metaprobes can be modulated so as to optimize their biological function and affinity to the target gateway enzyme.

An alternate approach in guiding the metaprobe design process would be to test its properties back to back with those of known substrates for the gateway enzyme. bioassays can be developed so as to determine the relative metabolic rates of tracer labelled substrates. Many of these have been published in the *Methods in Ezymology* (New York, Academic Press) and related monographic series, especially as microdose assays for evaluating the kinetics of hydrolytic or oxidative processes (Bircher and Preisig, 1981; Davidson et sl., 1981; Griffith, 1985; Vann et al., 1977). Thus, any metaprobe can be assessed for the efficiency of its design prior to further application in vivo. Taken as a whole, these aforementioned methodological steps have been those invoked in arriving at the preferred subset of metaprobes described in subsequent illustrative examples.

From the general discussion of metaprobe design, it can be seen that all candidate molecules share in common certain structural properties that render them useful as diagnostic probes for the underlying enzymatic pathways whose function they are designed to probe. In qualitative terms, metaprobes are substrates for their respective gateways. Thus, in addition to the chemical properties for the combination of release tag, core tracer and derivative complex, the metaprobes described in this invention may share as a common characteristic the fact that they are analogs of known therapeutic agents, when these latter themselves are known inhibitors of the gateway enzymes that are the target of their therapeutic mode of action.

When applicable, a preferred embodiment of the metaprobe concept consists of isotopically labelled analogs of therapeutic drugs that retain the isosteric and electronic properties of that drug but do not show any potency as biological effectors because the non-scissile bonds of the therapeutic congener have been replaced with hydrolyzable ones. Therapeutic agents that inhibit gateway enzymes are designed specifically for their resistance to enzymatic conversion. In contrast, their analogous metaprobes, when acting as substrates in the context of this invention, must consist of molecular configurations that permit them to become rapidly metabolized. Consequently, in this invention, a preponderance of favored metaprobes are assembled from constituent parts taken from the amino acid family of molecules, and especially those amino acids that are not incorporated into the protein synthesis pool. Molecules of this kind are generally regarded as safe, do not have drug potency, and can be readily assembled via peptide bonds, or other amide and ester linkages, into molecules whose design adheres both to the physiochemical and structural properties specified by the definition of suitable metaprobes in accordance with this invention.

The examples that follow illustrate how the basic structure of a representative selection of metaprobes ultimately defines the structure of the analyte that is to be quantitated in order to judge the extent and efficacy of the gateway enzyme acting upon it. They are intended to identify the basic structure and acceptable structural variations of metaprobes according to their mode of action at the gateway enzyme. These metaprobes are intended for use by one or more of the routes of administration, as described in the following section. It should be also understood that the fate of the component tracer core and of the release tag in each of these metaprobes may be traced and quantitated by one or more of the general methods that are customarily employed for the measurement of isotopic labels in various biological matrices, most notably by mass spectral methods applied directly to the release tag or to the tracer core. A variety of analytical techniques can be brought to bear on the detection of the isotopic content, and therefore, the rate of change in isotopic content as a function of biological residence time.

The following examples are presented to illustrate the advantages of the present invention and to assist one of ordinary skill in making and using the same. These examples are not intended in any way otherwise to limit the scope of the disclosure.

EXAMPLE I

The Method of the Invention in Generic Form

Operationally, the application of the metaprobes in this invention follows the same basic sequence of steps. The metaprobe is first tested in one or more healthy individuals in order to determine a metabolic index value for the gateway enzyme system under consideration. This is accomplished by dispensing a known dose of the metaprobe by an appropriate route of administration, which in separate instances may be either oral, intravenous, intra-arterial, intraluminal (rectal, vaginal, nasal, tracheal, otic), intrathecal, intramuscular, subcutaneous or transdermal. The preferred route of administration for analysis of gateway enzyme kinetics is oral, but for purposes of evaluating gateway enzyme metabolism beyond the splanchnic bed, it would be appropriate to dispense the metaprobe into those body compartments that are most proximate to the organ systems whose biochemical funtions are being probed.

Next, the appearance of release tag at one or more time intervals after metaprobe administration is monitored, the investigator having first taken a "blank" or background sample at the time of dosing. The preferred sampling site for analysis of gateway enzyme kinetics is in breath, which constitutes the least invasive approach, but it also may be appropriate to determine the amount of release tag in other accessible sites, such as plasma, urine, feces, luminal lavage fluids, tears, saliva, bile, sweat, or tissue samples obtained by needle aspiration or surgical biopsy. The selection of sampling site is made on the basis of how proximate it is to the tissues and organs whose gateway enzymes are under scrutiny and the extent to which organ localization is an important determinant in formulating a clinical judgement about the overall function of gateway enzymes under normal, in contrast to pathophysiological, conditions. Consideration should also be given in the selection of a sampling site to the extent that the sampling site reflects an adequate rate of appearance of release tag which, for practical purposes concerning patient comfort, should be maximal within two hours of metaprobe administration.

Finally, a metabolic index that reflects gateway enzyme activity in terms of either metaprobe rate of disappearance, release tag rate of appearance, or other kinetic measures of substrate flow through the gateway enzyme at the organ sites where metaprobe metabolism is preponderant, is calculated. Laboratory and computational procedures for carrying out such calculations have been extensively described in the academic and patent literature (Barshop et al., 1991; Bier, 1997; Browne, 1997; Cobelli et al., 1987, 1992; El-Khoury et al., 1996; Klein and Klein, 1979; Patterson, 1997; Wiechert and DeGraaf, 1996; Wolfe, 1992; and U.S. Pat. Nos. 4,676,974; 5,100,779; 5,233,997; 5,338,686; 5,386,832; 5,413,917; 5,432,058; 5,466,434; 5,628,328; 5,756,067). The standard techniques for interpreting the kinetics of tracer metabolism may also be augmented by the kinds of computational short cuts well known to pharmacokineticists, who have developed numerous methods to characterize the temporal properties of interindividual drug metabolism. In the context of metaprobe utilization, the preferred techniques are those non-compartmental and minimal compartmental (up to 4 compartments) generic models that permit deconvolution of the tracer mass balance relationships and fractional flux rates during the various phases of metaprobe absorption, core tracer distribution, and release tag irreversible disposal, regardless of route of administration (Barrett et al., 1998; Bourne, 1995; Heinzel et al., 1993; Katz, 1989; Lassen and Pern, 1979; Wagner 1976; Wagner, 1993).

The metaprobe is tested on a patient who is being evaluated for a condition in which the gateway enzyme under consideration is an indicator for pathophysiological dysregulation, using the same protocol developed on a normative cohort of healthy individuals. A suitable metabolic index based on the temporal properties of the metaprobe disposal is then computed by the same pharmacokinetic manipulations as applied to results from normal controls.

Comparison is then made between the metabolic index value obtained for the patient and the normative values for the control population. Any significant variation thereof, i.e., the metaprobe test score, is taken as a measure of disease severity and can then be tracked longitudinally as an indicator both of disease progression or remission in response to therapeutic intervention. The magnitude of the metaprobe test score may also be utilized as a management tool in the selection of gradations in therapy, or alternate therapies altogether, that are considered optional in proportion to the degree of divergence between the patient's test score and normal values or in step with the variation among individual patient test scores taken without reference to any other benchmarks. The magnitude of the metaprobe test score also can be interpreted as a measure of risk, in cases where overt symptoms of disease are not presented, and, therefore, can serve a guideline for initiation of appropriate preventive measures. In this latter implementation, the metaprobe test score serves as a prognostic or patient stratification index, pointing to the relative immediacy or future eligibility for treatment.

Further disease and therapy management information about the patient can also be obtained by administering the metaprobe test sequentially at the start of a multi-part treatment regimen. Under this operating condition, the first test score serves as the basal control value prior to initiation of the desired first intervention and any subsequent test score, taken at periodic intervals, can be used to assess whether or not the patient has returned to basal values prior to repetition of the intervention with greater frequency or intensity. In this instance, the patient serves as his/her own control. Similarly, the metaprobe test can be used as part of a stimulatory or suppression protocol aimed at determining the functional capacity or functional reserve of a target gateway enzyme. In such a protocol, the patient is tested under basal conditions and then submitted to a calculated stress or insult, either mechanical (e.g., exercise) or pharmacological in nature, intended to challenge those homeostatic mechanisms in which the gateway enzyme under evaluation is a primary effector. A second metaprobe test is performed upon completion of the challenge period, and the difference between the post and pre test scores are computed. The magnitude of any difference can be used as a metric norm for adaptive capacity and, therefore, can serve as a quantifying index among classes of patients presenting with varying degrees of disease severity or between patients and those individuals who are deemed to be healthy, normal controls.

EXAMPLE II

Enzymatic Pathways Containing Gateway Enzymes and Their Associated Disease States Gateway enzymes are essential components of three fundamental enzyme-enabled pathways that relate to the glutathione cycle and mechanisms of cytoprotection (FIGS. 1a and 1b); the arginine/nitric oxide signaling pathway (FIG. 2); the homocysteine/methionine cycle (FIG. 3); and the hexosamine/insulin resistance pathway (FIG. 4). Assessment of the glutathione cycle measures the body's ability to "bounce-back" from trauma or other insult and probably has the broadest clinical application. The measurement of cytoprotective capacity and resistance to oxidative stress, as reflected in the glutathione cycle, is immediately applicable in cancer treatment to assess a given patient's ability to withstand a dose of chemotherapy. Cancer cachexia, or wasting, also can be managed with more effective nutritional intervention, since the glutathione cycle is responsive to available nutritional supplements. Patients with AIDS, hepatitis, and long term neurodegenerative disorders, such as Parkinson's and Alzheimer's disease, might also benefit.

In combination with monitoring the glutathione cycle, assessment of the arginine/nitric oxide (NO) signaling pathway may be useful in managing ICU patients with burns, trauma, heart failure, septic shock and ARDS. Monitoring of the arginine/NO pathway may furthermore be useful to predict and manage patients with potential irreversible, runaway processes and chronic problems such as congestive heart failure, emphysema, and cachexia.

Homocysteine and related methionine derivatives are recognized markers for risk of atherosclerosis. Specifically, elevated plasma homocysteine concentrations are associated with increased risk for premature occlusive vascular diseases. Since plasma homocysteine can be managed with nutritional therapies, the method of the invention can be used to identify at risk patients, track therapy management, and lower the incidence of heart disease.

Hyperglycemia and its concomitant "glucose toxicity" effect at the cellular level has been convincingly demonstrated as the cause of most, if not all, of the chronic complications of diabetes, especially cardiovascular morbidity and mortality. The abnormal concentration of glucose in cells, once glucose homeostasis has been disrupted under pathophysiological conditions, has been linked to an increase in hexosamine flux and, therefore, to a dysregulation of the glutamine-fructose-6-phosphate aminotransferase gateway enzyme system, which then overproduces glucosamine. Excess glucosamine then causes insulin resistance, via one or more cell signaling pathways that are tuned to increased glucosamine-mediated protein glycation, and accelerates a vicious cycle that worsens the diabetic state and makes therapeutic glycemic regulation more difficult. Thus, monitoring the activity of glucosamine production by the application of a metaprobe by the method of this invention can be used to first assess the potential severity of glucose toxicity prior to the onset of its symptoms and then to track the course of its amelioration by intervention with insulin, anti-diabetic drugs or other therapeutic modalities aimed at restoring normal euglycemia.

In terms of the gateway enzymes, identified for illustrative purposes in this Example II, the diseases associated with them and enumerated at the outset of this Example can all be monitored by their biochemical signatures as embodied in metaprobe test scores. All such text scores can be elaborated in accordance with the generic protocol just described in Example I, which should be taken as the modus operandi in all subsequent illustrations of this invention.

EXAMPLE III

Use of the Method of the Invention with Oxoprolinase

Oxoprolinase is a ATP dependent enzyme in the γ-glutamyl cycle (FIG. 1a) with the lowest Km in the sequence (Jackson et al., 1996; Meister et al., 1985; Meister, 1989). As such, it represents a bottleneck whose activity can therefore be viewed as an indicator of overall flux through the cycle that ultimately produces glutathione, the principal antioxidant and effector of cell cytoprotection against oxidant stress. Under basal conditions of homeostasis in healthy young mammals, especially humans, the production capacity of the glutamyl cycle is held in check by a feedback mechanism preventing glutathione overproduction unless it is needed to address an insult caused exogenously by trauma, bacterial or viral insult, or endogenously by cytokine/chemokyne cell signaling cascades that are triggered by pathophysiological conditions in organs of the splanchnic bed or of the cardiovascular system.

Thus, under normal conditions, precursors from the glutamyl transpeptidase and the glutamyl cyclotransferase are shunted into oxoprolinase as its natural substrate oxoproline. In fact, when glutathione synthesis is inhibited chemically or blocked genetically in inborn errors of metabolism, oxoproline will accumulate in toxic concentrations because the oxoprolinase kinetic bottleneck cannot metabolize the overload. Conversely, during periods of high glutathione demand, in order to meet the needs for increased cell cytoprotection and xenobiotic detoxification, the substrate flow is shunted towards the production of glutamylcysteine, leaving little material for conversion by the cyclotransferase into oxoproline and its subsequent hydrolysis to glutamate by the oxoprolinase bottleneck.

Ideal metaprobes for the oxoprolinase gateway, and, therefore, indicators of the overall throughput of substrate through the γ-glutamyl cycle, include tracer labelled variants of oxoproline and its structural analogs, whose physico-chemical properties are compatible motifs, in accordance with the rules for metaprobe design, with the oxoprolinase active site domain. These include, as shown in FIG. 5, analogs and homologs of oxoproline, serving as the core tracer, with a common release tag, a carbonyl group labelled preferably with $^{13}C$, that effects ring closure between the α-amino acid substituent and the thiol terminus in order to complete the carrier complex. Further structural modifications of the carrier complex, aimed at affecting lipophilicity and rate of transport from different sites of metaprobe administration, are effected by substitution of the free carboxylic acid with hydrolyzable groups, including but not limited to those shown in Table 4. But all must contain the 2-oxo-thiazolidine functionality in order to be hydrolyzed at rates within the same order of magnitude as the natural substrate, oxoproline. Accordingly, the structures shown in FIG. 5 are compliant with the requirements for competitive activity as substrates for oxoprolinase and conform to the design considerations previously enumerated in the biochemical literature about this enzyme (Meister, 1989). The utility of one such metaprobe was verfied in the following trial on human subjects.

L-2-oxo[$^{13}C$]thiazolidine-4-carboxylic acid (OTC) is a 5-oxoproline analog which when acted upon by 5-oxoprolinase, is converted to cysteine (CYS), the rate limiting amino acid for glutathione (GSH) synthesis, with the release of $CO_2$. Studies have shown that OTC administration can replete cellular GSH stores when the GSH pool has been depleted due to detoxification of drug metabolites (Giorgi et al., 1992; Kalayjian et al., 1994; Levy et al., 1998; Vita et al., 1998). In this example, it was first determined that orally administered $^{13}C$-labelled OTC could be used to detect changes in the body's GSH stores. OTC satisfies the criteria of a metaprobe to be used in the method of the invention as follows: it is a substrate of oxoprolinase and a demonstrated competitive inhibitor of oxoprolinase hydrolysis by enzymatic assay (Meister et al., 1985), while its pharmacokinetics of in vivo disposition are known to follow the same temporal properties of comparable doses of oxoproline; its physical properties, solubility, acidity and lipophilicity are indistinguishable from those of oxoproline; the hydrolysis of OTC instantly liberates $^{13}CO_2$, an ideal release tag which is rapidly transported into the peripheral circulation and exhaled into breath, and the remainder of the molecule is no longer recyclable as a substrate, that is, its hydrolysis represents a one way metabolic "street"; both the tracer core and the release tag, namely, cysteine and carbon dioxide, are natural biochemicals generally regarded as safe; and the toxicological properties of the OTC metaprobe are both demonstrably unremarkable (White et al., 1992) and less toxic than those of oxoproline itself, a natural material and constituent of the body.

Seven healthy volunteers (ages 22–39) each participated in two studies. After three days on a weight maintaining diet, each participant was given a drink containing $^{13}C$-labelled OTC (1.5 mg/kg), following which blood and expired breath were sampled frequently. In the first test, each participant received the OTC alone. In the second study at least one week later, each participant ingested 2 gm acetaminophen one hour prior to the OTC drink. Expired breath samples were analyzed for the $^{13}C$ enrichment (APE) of $CO_2$, and expressed as isotopic enrichment in atom per cent excess (APE×1000) versus time, in the usual manner and in accordance with the general protocol described in Example I. A second panel of probands (ages 53–73) were tested in a similar manner.

Figure 6:
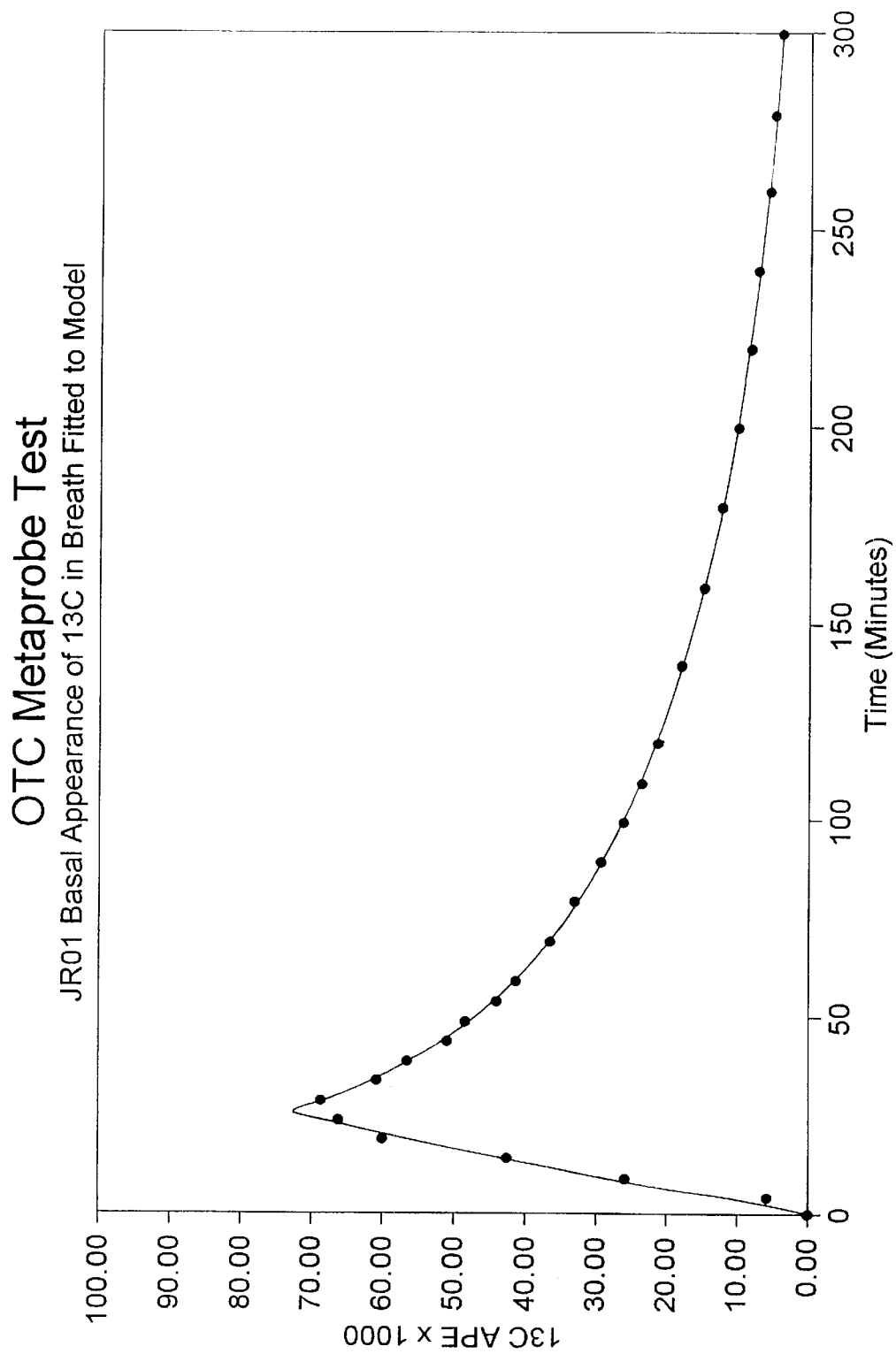
FIG. 6 depicts the kinetics of appearance of $^{13}C$—$CO_2$ release tag in breath after oral administration on an oxoprolinase metaprobe.

A representative plot showing the appearance of $^{13}C$-release tag in breath is shown in FIG. 6. From the pattern of label enrichment, at least two types of kinetic processes are apparent, one is absorption, since the metaprobe was dispensed orally, and the other disposition. Pharmacokinetic analysis of the entire "exhalation" curve, using an automated modeling program, showed that the metabolic process of OTC hydrolysis in vivo is best described, on the basis of goodness of fit criteria, as a two compartment model with lagged, zero order absorption into the peripheral plasma compartment, equilibration with a systemic metabolic compartment at the tissue level, and elimination from the peripheral compartment ultimately via the pulmonary circulation and into breath.

Deconvolution of this model by equation transformation and coefficient matching (Wagner, 1993) afforded separate kinetic measurements for the post absorptive metabolism of OTC in the metabolic compartment, and this was expressed as a fractional catabolic rate (Lassen and Perl, 1979). Lastly, the per cent of metaprobe dose recovered in breath was computed from the cumulative integral of the $^{13}CO_2$ enrichment versus time plot multiplied by the $CO_2$ production rate for each proband, which in these experiments were measured by indirect calorimetry (but can also be estimated from formulas that have been proven to correlate an individual's height, weight, age and gender with $CO_2$ production). The metabolic index for OTC utilization by oxoprolinase was then computed by the simple expedient of multiplying the dose of metaprobe by the per cent recovery and then by the fractional catabolic rate.

Under basal conditions when the "emergency" demand for glutathione is low, one would expect a relative surplus of incidental substrates within the γ-glutamyl cycle. Conversely, under conditions of high glutathione demand and concomitant continual synthesis, such as in response to a hepatotoxic challenge from acetaminophen ingestion, one would expect proportionately lower levels of incidental substrates, such as oxoproline, because all available precursors for the glutamyl skeleton of glutathione are being shunted into glutathione production. Thus, when an oxoprolinase metaprobe is dispensed under basal conditions, there would be sufficient natural substrate, in this case oxoproline, present at the site of metabolism to compete with it. More oxoproline relative to OTC would be expected to be metabolized per unit time, resulting in a lower relative rate of OTC conversion and a lower cumulative level of release tag appearance at the sampling site in breath. By contrast, in response to a glutathione depleting stimulus, glutathione production becomes elevated, oxoproline synthesis is suppressed for lack of glutamyl substrates, and therefore the oxoprolinase gateway enzyme can metabolize exogenously added metaprobe at a faster relative rate, resulting in the appearance of higher amounts of release tag in breath than under basal conditions.

The data from the validating trial in this Example III all corroborate the biochemical hypothesis concerning the OTC metaprobe's mode of action as an indicator of oxoprolinase activity and, therefore, its utility as a surrogate indicator for glutathione production capacity. The results, which are expressed in terms of nanomoles of OTC metabolized per kilogram body weight per minute for the basal condition (BASAL), post acetaminophen (ACE+), and the stimulatory difference between ACE+ and BASAL (STIM) are shown in Table 5.

TABLE 5

Metabolic Rate Index (nMol/kG/min) After an Oral Dose of $^{13}$C-OTC With and Without Acetaminophen

| AGE | YOUNG (22–39 yrs., n = 7) | OLD (53–73 yrs., n = 5) | ALL (22–73 yrs., n = 12) |
| --- | --- | --- | --- |
| BASAL | 286 +/− 111 | 335 +/− 110 | 307 +/− 108 |
| ACE+ | 547 +/− 269 | 452 +/− 161 | 515 +/− 227 |
| STIM | 261 +/− 115 | 117 +/− 40 | 208 +/− 82 |

In all subjects, the metabolic rate index of the OTC metaprobe was significantly higher (p <0.05) after the glutathione depleting insult than before. The YOUNG set showed a lower basal level and a higher level of metaprobe utilization, consistent with the view that glutathione homeostasis is altered by the aging process and, therefore, a more prolonged exposure to oxidant stress. The difference in adaptive capacity, as measured by the STIM parameter, was twice as large in the YOUNG than in the OLD and was highly significant (p<0.01). Taken as a whole, these data support the hypothesis that the OTC metaprobe effectively tracks the course of glutathione depletion, even after a mild insult, and can also be used to estimate the relative capacity of the glutathione production machinery in cohorts with different oxidant stress histories.

By extending the application of the OTC metaprobe to therapy management, it should be possible, in a similar manner, to stratify probands both according to their basal OTC metabolic index and to their production capacity in response to a controlled insult, such as that provided by acetaminophen. Patients with a high basal metabolic index and/or a low STIM score would be the least likely to benefit from antioxidant and related therapies aimed at boosting the glutathione machinery, e.g., in AIDS (Kalayjian et al., 1994) and cardiovascular disease (Vita et al., 1998) and can be predicted to be the most susceptible to harm from treatments, such as chemotherapy, whose coincident biochemical effects include chronic GSH depletion, e.g., hemorrhagic cystitis (White, et al. 1995) and bone marrow hypoplasia (Goldberg et al., 1995). By extension, the estimation of an OTC metaprobe STIM value in patients contemplating any intervention that might be expected to weaken glutathione mediated host defenses can be expected to foreshadow their relative ability to maintain glutathione homeostasis. Patients with higher BASAL scores and lower STIM scores would predictably be the ones to sustain higher morbidity and mortality.

EXAMPLE IV

Use of the Method of the Invention with Chymotrypsin.

The pancreatic enzyme chymotrypsin attacks substrates containing the aromatic acids tyrosine, tryptophan, phenylalanine, and, to a lesser extent methionine (Rinderknecht, 1986). The alkyl esters of these amino acids are also hydrolyzed, as are amides of substituted anilides. The specificity of all three chymotrypsin isoforms (A, B, C) is widely overlapping, with the exception that chymotrypsin C shows an increased ability to hydrolyze peptide, ester and amide bonds of the branched chain amino acids, leucine in particular. Accordingly, the preferred embodiment in a metaprobe designed to act as a substrate for all the chymotrypsins calls for leucine and its analogs as the tracer core. The optimal release tag in this configuration of tracer core is an isotopic label in the skeleton of the tracer core, and preferably at the carboxyl. Given the preference of chymotrypsins for aromatic amino acids, the preferred Derivative Complex consists of N-terminal peptides of the tracer core with the aromatic amino acids, in particular, tyrosine and phenylalanine in addition to a suitable carboxyl substituent on the tracer core, taken from the structural candidates listed in Table 4, but also including the carboxamides with 4-aminobenzoic acid and 4-aminophenylsulfonic acids. A schematic representation of this metaprobe is depicted in FIG. 7.

In a preferred embodiment of the method of the invention, these metaprobes are used as follows: the metaprobe is dispensed orally into the stomach of the test subject (or animal). In the absence of chymotrypsin, an event indicative of exocrine pancreatic insufficiency, the tracer core remains intact and the release tag is not subsequently available for detection, indicating pancreatic exocrine insufficiency and disease. Under normal conditions of pancreatic function, the metaprobe, which would otherwise pass through the digestive system unmetabolized, is hydrolyzed by pancreatic chymotrypsins. The liberated leucine analog (i.e., the tracer core) is absorbed and rapidly metabolized by the splanchnic bed, whereupon the release tag is liberated as $^{13}CO_2$ into the peripheral circulation and is ventilated by the lungs. Alternatively, the isotopic enrichment of the tracer core can be determined by isolating it from plasma or from other tissues and evaluating the tracer content directly by any suitable analytical technique.

The relative speed with which the metaprobe is hydrolyzed and the proportion of its dose that is cumulatively hydrolyzed overtime can be computed by pharmacokinetic, numerical evaluation of the $^{13}CO_2$ release tag or tracer core enrichment-time curve, thereby affording a proportional index of chymotrypsin enzymatic activity and gradations therein between and among subjects, with varying degrees of pancreatic secretory activity, and in a manner sufficient to differentiate between normal and abnormal pancreatic function (Goldberg and Durie, 1993).

Beyond gastroenterological applications, metaprobes specific to chymotrypsins are also functional substrates for enzymes that coincidentally share their substrate specificity but are not enzymes of pancreatic origin. Thus, in another aspect of the invention, a specific metaprobe is administered in such a way so as to direct it to a specific source or pool of the desired gateway enzyme in the subject. This aspect is pertinent when one is testing, e.g., one important class of these chymotrypsin like-enzymes, which are also gateway enzymes in Class III, the family of chymases that mediate angiotensin conversion under conditions of chronic therapeutic use of angiotensin converting enzyme inhibitors (Liao and Husain, 1995). The administration of metaprobes specific to chymotrypsin by routes of administration that bypass the pancreas and contact with pancreatic proteases, i.e., by intravenous, subcutaneous, intramuscular, intrabronchial or transdermai delivery, may be used to titrate in a similar manner the chymase capacity of the test host.

Another important class of chymotrypsin-like gateway enzymes involved as mediators of pathophysiological states in skin (Havima, et al., 1994) and along the submucosa of airways in the respiratory tract (Welle, 1997) are chymases associated with systemic mast cells. Mast cells regulate the immediate-type hypersensitivity reaction in non-allergic immune disorders as well as in normal physiological regulation of neuropeptide activity, bronchomotor tone and fibroblast mitogenesis (Holgate, 1997).

A representative chymotrysin metaprobe was synthesized by reaction of N-acetyl-L-phenylalanine with L-leucine[1-

$^{13}$C], the latter protected as the carboxylamide with p-aminobezoic acid ethyl ester. Dosages of 1.5 mg/kg dissolved in 60 ml of ENSURE+ (a liquid meal) were dispensed to a cohort of probands considered normal with regard to digestive function and to a cohort suffering from pancreatic insufficiency secondary to alcoholic liver disease. The appearance of release tag was monitored and analyzed as described in Example I, but the test criterion was taken to be cumulative recovery of tracer as a percentage of dose two hours after ingestion. Normal subjects exhibited a Recovery Score of 69+/−15 per cent (n=3), while subjects with maldigestive compromise, attributable to insufficient pancreatic trypsin secretion afforded a Recovery Score of 22+/−11 (n=3), indicating that the metaprobe score provided a statistically significant differentiation in status both in accordance with clinical presentation and consistent with the principles of metaprobe operation for the chymotrypsin gateway enzyme system.

EXAMPLE V

Use of the Method of the Invention with γ-glutamyl Transpeptidase (GGT)

Figure 2:
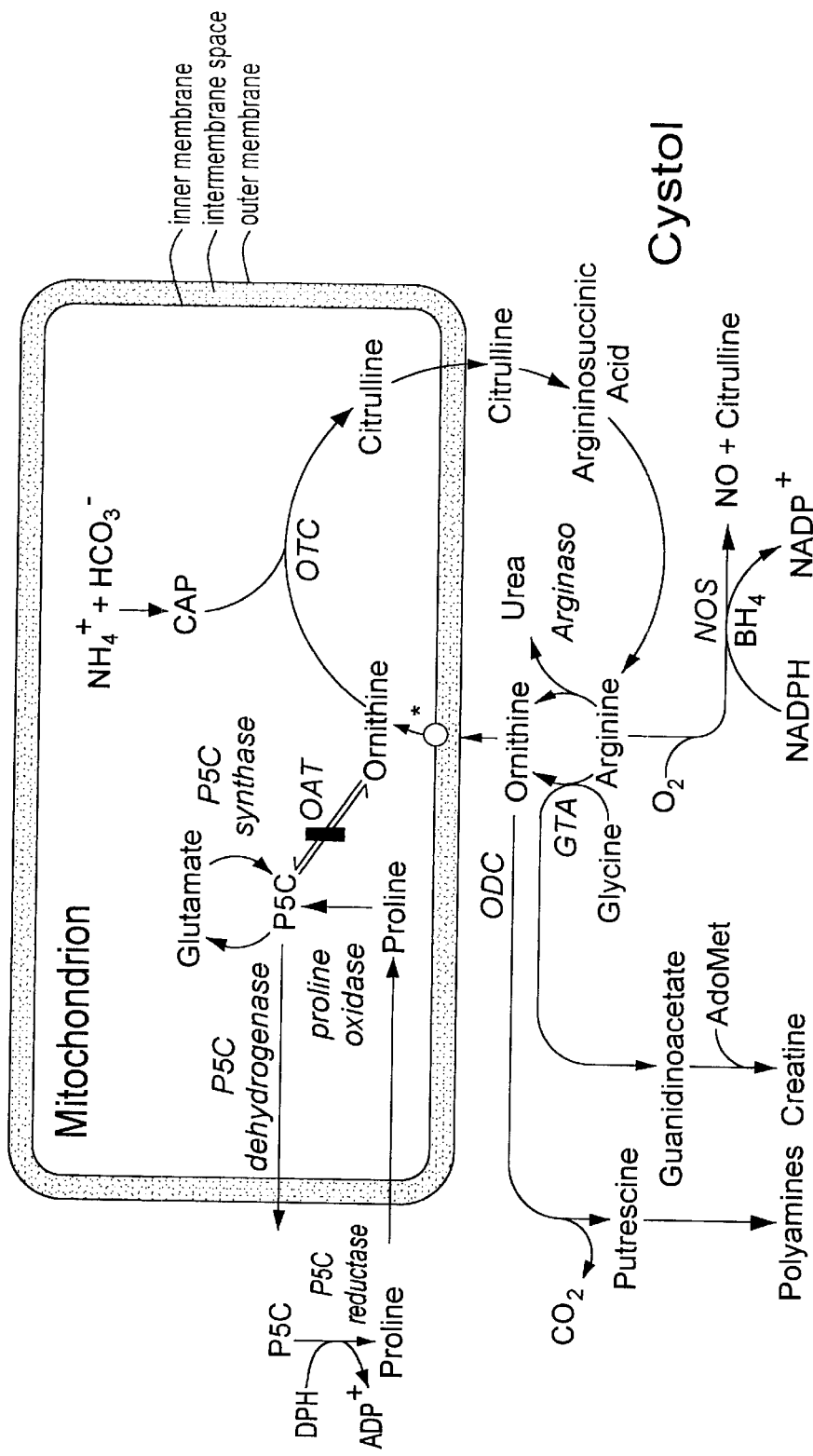
FIG. 2 illustrates gateway enzymes in the arginine/nitric oxide signaling pathway.

As shown in FIG. 1a, this membrane-bound enzyme transfers the glutamyl moiety of extracellular glutathione to acceptor substrates and therefore mediates the release of cysteine as well as the glutamyl-S-peptides into cells. It is the gateway into the γ-glutamyl cycle, the metabolic pathway that accounts for the enzymatic synthesis and degradation of glutathione. Glutathione itself is essential to the maintenance of cellular antioxidant status. It participates in providing reducing equivalents for many biosynthetic processes and is also a major substrate for the conjugative disposal of eicosanoids, carcinogens, toxins, and other mediators of inflammation and allergic responses (Allison, 1985; Tate and Mesiter, 1985).

Specifically, the properties of GGT as a gateway enzyme permit its use as a marker for proliferating tissue during pre-neoplastic transformations. GGT has been tracked in patients with breast cancer (Durham et al. 1997), melanoma (Benathan 1997), and small cell carcinoma (Ohlhauser et al. 1997). The temporal properties of its change in tissue concentration and in whole-body activity are also being exploited diagnostically as indicative of the status of cell differentiation and cell aging. For example, high enzyme activity is seen in cells of organs that participate in intense secretory or absorptive functions, such as epithelial canalicular, acinar and ductule cells, in the gut, kidney and liver. GGT titer is associated with the outcome of liver transplantation (Hasegawa, et al., 1997), the severity of liver dysfunction consequent to gastrointestinal malabsorption syndromes (Picot et al 1997), the response to oxidative stress in children with lung injury (Hull et al., 1997), the course of alcoholic liver disease (Bellini et al., 1997; Bianchi, 1997), and, more significantly the susceptibility to treatment for viral hepatitis (Colombatto et al., 1997; Laghi et al., 1997; and Pawlotsky et al., 1998). Therefore, using the method of the invention to assess GGT capacity in the whole body, or in selected organ systems accessed by different routes of metaprobe administration, will provide valuable insight into the success of therapeutic intervention in specific disease conditions, whose severity is already associated with changes in GGT activity.

In the prior art, numerous substrates for GGT have been explored by classical enzymological techniques and by radiotracer methods in vivo in which test animals are sacrificed, their organs and tissues disaggregated, and the concentration of GGT metabolism product identified by radiography and radioscintillation (Meister, 1985, 1989). These experiments afford a point of departure for determining a useful structure for a GGT metaprobe. It is known that glutathione analogs, both tripeptides and dipeptides, serve as GGT substrates, provided that their N-terminus consists of a γ-glutamyl moiety (which may be racemic or either enantiomer and structural analogs thereof) linked to cysteine or an isostere, serving as the preferred tracer core, the preferred embodiment of the latter being 2-aminobutyric acid labelled in its carboxyl group as the preferred form of release tag. This dipeptide may, in turn, be linked to glycine, a necessary component to maintain substrate binding to the GGT active site. For purposes of modulating absorption and distribution of the metaprobe, both the C-terminus and the N-terminus carboxyl may be protected by hydrolyzable substituents, as described in Table 4, in order to complete the carrier complex structure.

In addition to the tripeptide and dipeptide configurations of this metaprobe, a minimal metaprobe configuration consists of the γ-glutamyl moiety attached via an amide linkage to a suitably derivatized analog of 4-amino-benzoic acid, a molecule also known to be a general substrate for the evaluation of transglutamylation biochemistry (Szewczuk and Wellman-Bednawska, 1978). In this latter case, the glutamyl substituent itself serves as the tracer core, labelled at either the 1 or the 5 carboxyl groups, which, in turn, become the release tags.

A schematic representation for the GGT metaprobes is depicted in FIG. 8. These configurations include the known glutathione analogs, ophthalmic and norophthalmic acid, and their analogs whose methods of synthesis follows classical approaches for peptide synthesis, the exception being incorporation of a tracer labelled isotopolog as the tracer core substituting for cysteine (Douglas, 1989; Cobb et al. 1982). In all the three embodiments of this metaprobe, the tracer core is intended to bear the isotopic release tag, preferably as $^{13}$C in the carboxyl group. Although carboxyl labelled 2-amino-butyric acid is the preferred tracer core in the tri- and dipeptide configurations, carboxyl labelled glutamic acid may also serve as an alternate tracer core in all three configurations.

Both 2-amino-butyric acid and glutamic acid are preferred in this function, because their subsequent metabolism permits rapid generation of the release tag into plasma and breath. In the case of 2-aminobutyric acid, it does not enter into the protein synthesis reservoir and is rapidly transaminated to 2-ketobutyric acid which immediately enters the pathways of decarboxylative intermediary metabolism. In the case of glutamic acid, transaminative exchange is rapid and a ubiquitous intracellular reaction that affords 2-ketoglutaric acid, a key intermediate in the Krebs cycle and a principal contributor to the production of $CO_2$ as the end product of oxidative metabolism. No other tracer cores are known to be metabolized as fast as these two in mammalian systems.

The three forms of GGT probes provide diagnostic tools with a spectrum of specificities. The tripeptide form of the GGT metaprobe serves exclusively as a substrate for GGT. The dipeptide form offers a broader and additive picture of activity within the γ-glutamyl cycle because its metabolism is indicative of the combined enzymatic activity of GGT and glutamylcyclotransferase, an enzyme that can also liberate the tracer core from the dipeptide metaprobe structure but not from the tripeptide structure. Application of the monopeptide metaprobe, by extension, provides metabolic information about all transglutamylation enzymatic steps with the body including the activity of GGT and cyclotransferase. Thus, through the sequential use of each of these three metaprobes, there can be obtained a fractional measure of GGT versus total glutamyl-interconversion biochemistry. This fractional measure can then be correlated, compared or contrasted to the fractional measures so obtained under different physiological or pathophysiological conditions.

The differential use of homologous metaprobes, to characterize physiological biochemistry from the specific to the general within a family of enzymatic reactions, is itself a novel implementation of the metaprobe concept. These non-limiting illustrations of the interoperability of metaprobes, as specific substrates for fundamentally different gateway enzymes that are accessed by virtue of the mode in which the metaprobe is dispensed, constitutes yet another embodiment to this invention.

A representative GGT metaprobe was synthesized and tested in an animal model system. L-2-amino-butyric acid, protected as the carboxylamide with ethyl p-aminobenzoate, was coupled with 2-acetyl-L-glutamic-1-ethyl ester via mixed anhydride activation (Bodanszky and Bodanszky, 1994). The resulting dipeptide was purified by column chromatography and then crystallized to afford a colorless solid, mp. 264–265. Four male New Zealand rabbits were treated with 2 mg/kg of this GGT metaprobe by intravenous injecton, and respiratory gases were collected for isotopic analysis over a three hour period. Sixteen hours after the first metaprobe breath test, the animals were treated to a glutathione depletion stress consisting of a 50 mg/kg bolus of acetaminophen and 50 mg/kg of cyclophosphamide, once an hour for 3 hours. One hour therafter, a second intravenous GGT metaprobe test was carried out, followed by a three hour breath sampling period. The appearance of release tag was monitored and analyzed as described in Example I. Noncompartmental analysis of the release tag impulse-response curve, based on oxidation of the 2-aminobutyric tracer core and $^{13}CO_2$ release tag post metabolism, and calculation of the fractional catabolic rate-dependant Metabolic Rate index for metabolism in peripheral tissue afforded the following scores: 175+/−58 nMol/kg/min for the control period prior to toxicological stress and 987+/−134 for the post stress period. This result indicates that the GGT metaprobe test functions as postulated by the theory behind its design and provides a sensitive measure for the degree of insult provided by glutathione-depleting drugs used in chemotheraphy and that it can be used a gauge for quantitating the biochemical response, and therefore, tolerance, to the dose intensity of such drugs.

EXAMPLE VI

Use of the Method of the Invention with Nitric Oxide Synthase (NOS) (FIG. 3)

Nitric oxide has been shown to be the principal cell signaling effector in a multitude of pro-inflammatory conditions (Packer 1996, Part B). It regulates vascular tone and triggers many acute phase reaction cascades associated with trauma and sepsis, as well as the more subtle metabolic dysregulation associated with free radical attack and oxidant stress in endocrine (Oberley, 1989), neuromuscular disorders (Simonian and Coyle, 1996), and immune-related diseases (Cook and Cattell, 1996). Because the fate of nitric oxide is extremely complex as it becomes embedded in multiple biosynthetic pathways of radical interchange before being converted into a stable, oxidized end product, namely, nitrate (Beckman and Koppenol, 1996), conclusions drawn about the magnitude of NO production or of its therapeutic regulation in a living organism, especially humans, cannot be addressed by measurement of excreted nitrate (Castillo, et al. 1994, 1995; Beaumier et al, 1996). Similarly, a plethora of analytical techniques, both spectroscopic and immunochemical, do afford quantitative information about NO biosynthesis, but they are all inadequate for doing so in vivo (Packer, 1996, Part B). Genetic markers may also be dismissed as quantitative tools in so far as they do not address the phenotypic properties of precursor-product conversion and their temporal interrelationships in real time.

Because of these limits in available methodology for the in vivo monitoring of NO production, especially during the course of diseases affected by NO overproduction, an alternative approach was developed to estimate the upper limit of NO production. Since arginine is the natural precursor and substrate for NOS and both NO and citrulline are the two end products of that conversion, it has become possible to measure the whole body process by which NO is produced in terms of quantitatively tracking the conversion of arginine to citrulline, using tracer probes incorporated into the guanidino group of arginine. Accordingly, control studies in humans undergoing nutritional status evaluation now have validated that the conversion of L-arginine[guanidino-$^{15}N2$] to L-citrulline[ureido-$^{15}N_1$] matches the concomitant production by NOS of $^{15}NO$ (Castillo, et al., 1996; Lagerwerf et al., 1998). Unfortunately, the experimental mechanics for doing so involve a complex series of primed constant infusion studies and a complex series of secondary, control experiments that must be carried out in order to correct both the rate of arginine disappearance that is attributable to its cycling through the protein biosynthesis pool and the rate of citrulline appearance that is a result of de-novo synthesis from ornithine and not from the action of NOS.

The entire exercise of deconvoluting the fate of citrulline derived from arginine via the NOS pathway can be greatly simplified first by the use of more effective data reduction procedures based on compartmental deconvolution as described in Example III and, more importantly, through the use of improved metaprobes designed specifically in accordance with the principles espoused in this invention.

Figure 9:
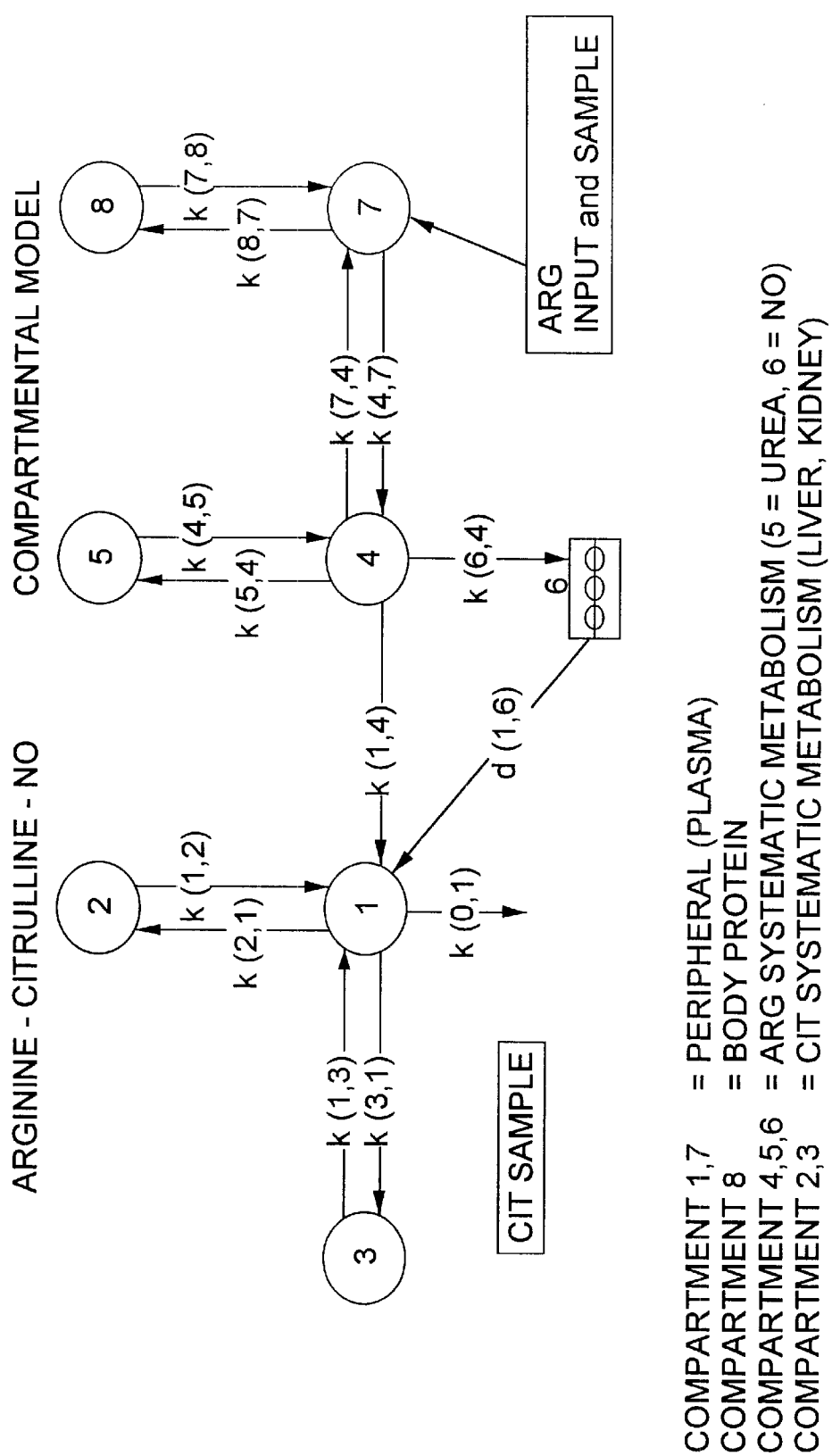
FIG. 9 illustrates a compartmental model for the relationship among arginine, citrulline and nitric oxide.

When L-arginine[guanidino-$^{15}N_2$], which is in effect a minimal metaprobe comprised of ornithine as the tracer core and the guanidino substituent as the release tag, is administered intravenously, either by bolus or by short-term infusion, the temporal properties of citrulline and arginine appearance are accurately described by the compartmental model depicted in FIG. 9. Although not recognized in the prior art, it follows from this model that a useful index of NO production (NOPI1) is defined as: NOPI1=CFSR×AREC, where CFSR is the citrulline fractional synthesis rate per kg body weight per hour via NOS from the compartmental model, corrected for the delay in rate of appearance, i.e., k(6,4)×d(1,6), and AREC is the amount in micromoles of arginine metaprobe recovered as citrulline after a period corresponding to 10 times the arginine metaprobe's plasma half life.

A further refinenement, designed to correct for interindividual differences in arginine flux, consists in normalizing NOP1 as a percent of arginine flux so that: NOPI2= 100*NOPI1/QA, where QA is the arginine plasma replacement rate computed by non-compartmental analysis of arginine residual enrichment versus time curve, the latter having been extrapolated also to 10 times the arginine metaprobe's plasma half life.

The NOPI index obtained in this manner represents an advance over the data interpretation schemes in the prior art (Castillo, et al., 1996; Lagerwerf et al., 1998) and can be used to characterize the NO production status, and, by extension, the oxidant stress load of patients who otherwise cannot be easily stratified on the basis of this underlying biochemical insult. Table 6 illustrates the relationship between the NOPI2 and the status of both normal control subjects and patients examined on admission to critical care for treatment of sepsis or complications from surgical trauma.

These studies constitute part of a continuing series intended to extend the protocols initiated by Castillo et al. (1996) and depend on intravenous metaprobe administration and mass spectral analysis of the resulting analytes extracted from plasma. They show both a statistically significant (p<0.01) difference in NO production status between normal controls or uneventful admissions to critical care and more complicated treatment cases that required a greater extent of hospitalization and exhibited greater morbidity and mortality. The timely use of the NOPI2 index as described in this invention in the future will permit the scheduling of more aggressive treatment for candidate patients who are suffering a predictable risk of complications from an elevated, and potentially unchecked, level of NO production at the outset of their hospitalization.

TABLE 6

Nitric Oxide Production Index (NOPI2) and Clinical Status/Outcome

| GROUP | NOPI2 on Admission | OUTCOME |
| --- | --- | --- |
| Normal Control | 0.2 +/− 0.15 (n = 4) | Healthy (not admitted) |
| 2 day average | 0.3 +/− 0.14 (n = 4) | Rapid recovery, no sepsis in ICU |
| 4 day average in | 2.99 +/− 1.24 (n = 4) | Recovery, sepsis treated ICU successfully |
| 7 day average in | 6.64 +/− 1.92 (n = 3) | Death from complications ICU of sepsis and trauma |

Notwithstanding the usefulness of the methodology just described, there remains considerable analytical complexity required to obtain the kind of results illustrated in Table 6. Such a potential drawback militates in favor of implementing a similar protocol with metaprobes that are intrinsically more amenable to rapid analysis and that adhere to simpler models for data deconvolution. Thus, preferred embodiments of the NOS metaprobe concept with greater potential clinical utility consist of arginine analogs which are known NOS substrates but do not participate in any subsequent biosynthetic processes, either prior to their conversion into ureido species, or thereafter through the various recycling processes that both citrulline and arginine are subjected to in vivo. These improved metaprobes, illustrated in FIG. 10, include the lower and the higher homologs of arginine, e.g., homoarginine, and a spectrum of therapeutic guanidino drugs, e.g., 5-guanidinovaleric acid, that are known to be substrates of NOS. In these structures, the tracer core can be taken from among homologs or analogs of ornithine and other suitably substituted alkyl amines that can maintain an affinity with the NOS active site domain (Hecker et al., 1991;Yokoi et al., 1994; Crane et al., 1997; Deshmukh et al., 1997). A release tag is then attached by guanidinylation of their corresponding free amino groups with a suitable reagent that affords either a $^{15}N_2$ or a $^{13}C$ or a $^{13}C$-$^{15}N_2$ guanidine or hydroxyguanidine. Subsequent functionalization of any remaining carboxyl groups yield the completed carrier complexes as depicted in FIG. 10.

Metaprobes of this design can then serve as more efficient in vivo substrates since their conversion by NOS from guanidines to the corresponding ureido species can now be traced more directly in so far as these metabolites are more biologically stable and non-recycling end products than their congeneric citrulline analogs. Further, unlike in the case of the arginine derived metaprobes, computation of the corresponding NOPI1 values for the metabolism of the structures shown in FIG. 10 will not require recalculation of the NOPI2 value. Normalization to the flux of metaprobe is no longer a necessity because in the absence of metabolic recycling there is no need to compensate for interindividual variations in the disposal of the parent metaprobe itself. Thus, the improved metaprobes offer a "one shot" kinetic profile in their conversion by NOS, and, therefore, can expedite both the computation and the specificity of the NO production measurement in those same clinical contexts as were examined in Table 6. Moreover, any expedited protocols for determining NO status would then permit application of these tools in an outpatient setting, both to follow the course of disease and the efficacy of antioxidant therapy, thereby expanding the scope of utility to include patient populations in whom NO oxidant stress is a contributor to increased morbidity caused by atherosclerosis, respiratory distress, cystic fibrosis, cataracts, macular degeneration, neurological disease (Parkinson's, Alzheimer's amyotrophic lateral sclerosis, non-alcoholic liver disease, diabetes, connective tissue damage (Sies, 1997) and pancreatitis (Tsai et al., 1998).

EXAMPLE VII

Use of the Method of the Invention with Cystathionine Synthase (CS) and α-ketoacid Decarboxylase (KAD)

In the last ten years, the biological chemistry of thiols in vasculature and in vascular-related disease has attracted overwhelming attention in the field of cardiology in so far as the alterations induced by oxygen free radicals are not only the causative agents of direct myocardial damage but also principal contributors to the development of arterial occlusive disease (Stamler and Slivka, 1996). One of the more significant interactions of free radicals (Sies, 1997; Ferrari et al., 1998) is with homocysteine, an intermediate in the methionine-cysteine remethylation pathway shown in FIG. 3. It is now, therefore, axiomatic that inability to clear homocysteine from the body, either through the vitamin $B_{12}$ and folic acid requiring pathways of methionine resynthesis or via metabolism through the cystathionine synthase gateway enzyme system, is a preponderant risk indicator for subsequent morbidity and mortality. For example, high plasma levels of homocysteine predict mortality in patients with angiographically confirmed coronary artery disease (Nygard et al., 1997), are a common finding in psychogeriatric populations suffering from dementia of vascular cause (Nilsson, 1996), and accompany the premature atherosclerosis of non-insulin dependent diabetics (Fonseca et al., 1998), especially among obese and elderly patients. Changes in the host's capacity for homocysteine synthesis and breakdown also correlate with the effect of aging on connective tissues, lipid synthesis, auto-immune diseases and carcinogenesis (McCully, 1994).

Current approaches for assessing homocysteine clearance are fall into two classes: a) genotypic assays aimed at predicted the individual's genetic propensity for homocysteinemia by identifying gene mutations or deletions, such as those governing the folate dependent thermolabile isoforms and b) static assays of plasma levels either by conventional chromatography or by isotope dilution mass spectrometry (Allen et al., 1990, U.S. Pat. No. 4,940,658; Allen et al., 1994, U.S. Pat. No. 5,374,560; Allen et al., 1995, U.S. Pat. No. 5,438,017). In this latter case, the result is a static plasma value and not a measure of production capacity, and presents with wide variations depending on the dietary history of the host. The more effective assay procedures are organized around a stimulatory event such as a methionine load, the theory of operation being that this extraordinary input of methionine (100 mg/kg) orally will "swamp" the various enzymes in the methionine-homocysteine-serine pathways and that those individual who cannot clear homocysteine fast enough relative to controls will then present with abnormally high plasma concentrations. The novel approach taken in this invention draws on the metaprobe concept, in an analogous manner to the schemes presented in Example I. Instead of merely examining static plasma levels, the use of a metaprobe permits direct assessment of the capacity to clear homocysteine, both before and after methionine load.

The principle of the test is to quantify the metabolic throughput of homocysteine metaprobe through the cystathionine synthsase (CS) gateway, also known as the transulfurization pathway. This enzyme converts homocysteine and serine into cystathionine. Its $K_m$ is the lowest in the cycle, consistent with the definition of "gateway" enzymes, and, therefore, serves as the metabolic entry to the irreversible disposition of homocysteine, since, once past the gateway, homocysteine can no longer participate in the remethylation cycle. Cystathionine is rapidly converted by cystathionase to cysteine and 2-aminobutyric acid (ABU), the latter bearing the carbon derived from the homocysteine skeleton. ABU, in turn, is rapidly transaminated to α-ketobutyric acid and then rapidly oxidized by the KAD gateway enzyme system into $CO_2$, which can be measured in breath. The $K_m$ values of both cystathionase and of the subsequent enzymes responsible for ABU degradations are two orders of magnitude higher than the values of cystathionine synthetase and, therefore, cannot be saturated by products of transulfuration.

In this invention, the rate of substrate metabolism through the CS gateway is accomplished in two ways. In Method 1, the metabolism of homocysteine itself is monitored directly with homocysteine metaprobes. In Method 2, the metabolism of homocysteine's principal non-recycling metabolite, namely ABU, is monitored by means of a KAD metaprobe that is structurally related to the products of the CS gateway enzyme.

In Method 1, homocysteine itself can be used as a tracer core, with labeling in any carbon group at the 1,2,3, and 4 position of the molecule, the preferred release tag being $^{13}CO_2$ incorporated into the carboxyl terminus. Because homocysteine and, especially, its thiolactone are both toxic and unpredictably reactive materials, these cannot be dispensed safely without derivatization into a suitable derivative complex, whose hydrolysis subsequent to dose administration will then serve as a form of controlled release of homocysteine to its site of metabolism. FIG. 11a depicts the metaprobes of greatest utility for direct measurement of homocysteine metabolism, which comprise a family of cyclic intermediates. Class A are oxoprolinase substrates, consistent with the structures illustrated in Example III, and generally synthesized by N,S cyclization with phosgene, ethyl chloroformate or a similar bifunctional carbonylating reagent. Class B are functionalized thiazolines formed by cyclodehydration of the free sulfhydryl and the free amine with a suitable aldehyde or ketone. The embodiments of Class B are known to hydrolyze spontaneously in plasma, thereby serving as a controlled release mechanism for the trecer core and release tag.

For Method 2, the prefered embodiments are KAD metaprobes constructed from aminobutyric acid and its derivatives labeled with carbon at any (or all sites), as shown in FIG. 11b. Metaprobes in this class find their preferred use as breath test substrates, when applied in accordance with the general procedures outlined in Example I. Two pilot studies were performed to illustrate their utility. In study 1, a BASAL measurement, CS activity was determined using the metaprobe L-2-oxo-tetrahydro-1,3-thiazine-4-carboxylic acid ethyl ester. The metaprobe was synthesized by phosgene cyclyzation of L-homocysteine[1-$^{13}$C] ethyl ester and isolated as a crystalline material, which afforded a sterile and pyrogen free solution after formulation and 0.22 micron ultrafiltration under aseptic conditions. An intravenous bolus of 2 mg/kg into was dispensed into male New Zealand rabbits according to standard procedures for conducting breath tests on small animals (Mohan et al., 1991). Breath collected in 10 ml evacuated containers at 5, 10, 15, 20, 25, 30, 45, 60, 75, 90, 105 and 120 minutes was analyzed by isotope ratio mass spectrometry and the resulting impulse response curve analyzed compartmental modeling (Wagner, 1993; Barrett, 1998). The temporal properties of the metaprobe metabolism were well suited to analysis as a two compartment open model with elimination from the central compartment after a delay period. A metabolic index was constructed, as in Example III, namely, the derived fractional catabolic rate in the peripheral (tissue) compartment multiplied by the dose of tracer metaprobe adjusted for the percent of isotope release tag recovered, using for this latter computation the area under the tracer-in-breath exhalation profile extrapolated to a time equal to 10 half-lives based on the $^{13}CO_2$ excretion rate constant. The next day, animals were preloaded by five small enteral feedings totaling 100 mg/kg of methionine dissolved in carrot juice and ingested over 0.5 hours. Two hours after consumption of the methionine challenge load, the metaprobe breath test was repeated. Table 7 shows the results of this MET+ test in comparison to the previously obtain BASAL values. LI, the load tolerance index, is defined as BASAL values minus the subsequent MET+ test score.

TABLE 7

CS Gateway Enzyme Gateway Breath Test in Rabbits Treated With Homocysteine Metaprobe

| GROUP | Metabolic Response Index (MRI) in MicroMol/kg/hr. |
|---|---|
| BASAL | 85 +/- 14 (n = 4) |
| MET+ | 28 +/- 16 (n = 4) |
| LI | 57 +/- 24 (n = 4) |

These findings are consistent with the underlying physiology of normal homocysteine clearance. Under basal conditions, the metaprobe is not diluted as much by the endogenous homocysteine. Hence, upon passage through the CS gateway, the metaprobe is metabolized in higher proportion than the endogenous substrate. Upon methionine load, more homocysteine is generated but not cleared quickly by either the easily saturated CS pathway or the transmethylative routes, thereby causing a transient homocysteinemia which dilutes the exogenous metaprobe to a significant greater extent. The dilution is reflected in the subsequent lower appearance of tracer release tag in breath characterized by the lower MRI test score. It follows that the LI value then represents a measure of the detoxifying capacity for homocysteine. Using this approach, a dynamic normative database can be generated as the basis for prognosis and management of disorders of homocysteine metabolism. Thus, individuals presenting with BASAL values lower than the norm and those unable to respond to methionine loads with a sufficiently high LI value to be considered "normal" can be indentified as belonging to a higher risk population, even at a time when they are asymptomatic for the overt, deleterious health effects implicit in the dysregulation of homocysteine clearance.

It should be noted further that an even simpler screening tool for homocysteine clearance regulation after a methionine challenge can be constructed using the KAD metaprobes shown in FIG. 11b. One of the preferred embodiments is a metaprobe constructed as the N-acetyl-ABU, with the release tag in the carboxyl group. This non-proteinogenic aminoacid is a safe natural product. Its oral ingestion leads to rapid absorption and rapid first pass metabolism by mitochondrial ketoacid decarboxylases in the liver, as described previously in Example V, and it is more than 70% cleared from the system in two hours. In a pilot trial, 2 mg/kg of this metaprobe were ingested by an adult male in the fasting state. The metaprobe was dissolved in 50 ml of orange juice. Breath samples were taken at periodic intervals over 2 hours. After an additional hour's rest period, the same subject ingested 100 mg/kg of methione in 50 ml of orange juice flavored with Angostura bitters, to mask the aftertaste of methionine. Again breath samples were monitored over two hours. Analysis by isotope ratio mass spectrometry of the enrichment in breath showed a biexponential rate of release tag appearance in breath, after an absorption phase whose kinetic order could not be characterized. The impulse-response curve was processed by compartmental deconvolution (Wagner, 1993) to afford mean residence times for metabolism in the central compartment (MRTC) and in the entire system (MRTS). MRTS-MRTC afforded a measure of metabolism in peripheral tissue (MRTP). As before, a metabolic rate index (MRI) was constructed according to the equation MRI=Dose×$^{13}$C-Recovery×1/MRTP. The experiment was repeated three times over a period of three weeks with the following results, shown in Table 8.

TABLE 8

CS Gateway Enzyme Gateway Breath Test in Man Treated With Aminobutyrate Metaprobe

| GROUP | Metabolic Response Index (MRI) in MicroMol/kg/hr. |
|---|---|
| BASAL | 145 +/− 24 (n = 3) |
| MET+ | 105 +/− 26 (n = 3) |
| LI | 40 +/− 9 (n = 3) |

Again, the findings are consistent with the KAD metaprobe's mode of action, in this case as an index of the metabolism of ABU when the CS gateway, a predecessor in the cystathionine clearance cascade, is overloaded. Taken as a combination, both these approaches to characterizing the regulation of homocysteine disposal offer a suite of sources for differential information about the metabolic effects of homocysteine pathophysiology and, therefore, can be used as prognostic and therapy management tools in interventions aimed at restoring homocysteine homeostasis to within normal values in patients whose dysregulation of this pathway is under consideration. Not only are these findings consistent with the results obtained by the standard loading protocols with either homocysteine (Guttormsen et al., 1996) or methionine (Bostom et al., 1995), but they are less invasive to perform than serological tests and have the overwhelming advantage of providing dynamic metabolic information rather than static plasma levels.

EXAMPLE VIII

Use of the Method of the Invention with Glutamine-fructose-6-phosphate Aminotransferase (GFT) and Liver N-acetyl Transferase (NAT)

In recent years, the diabetic population worldwide has increased steadily to such an extent that non-insulin dependent diabetes (NIDDM) can be viewed as a disease of epidemic proportions, especially when considered with the aggregate effect on morbidity and mortality of its collateral coronary artery disease. The importance of NIDDM as a negative cost factor in health care has prompted an accelerated search not only for antidiabetic drugs that can alleviate its impact (Ammon et al., 1996), but on the root causes. A link between free radical mediated oxidant stress and insulin dependent diabetes (IDDM) has been convincingly established in so far as NO mediated redox signaling leads to the self-destruction of insulin producing islet cells (Sies, 1996). For example, DNA strand breaks and activation of nuclear enzyme poly-ADP-ribose polymerase are prominent consequences of oxidant radical islet cell damage. In the case of NIDDM, the links between oxidant stress and dysregulation of insulin efficacy and/or increased-glucose toxicity still remain to be established except as coincident phenomena. The elderly and the obese, both of whom as classes of patients are most likely to sustain insults from oxidant stress, also present with the highest incidence of NIDDM. Moreover, approximately 15% of NIDDM cases will become insulin dependent, so that there exist commonalities in the underlying pathophysiology of both diabetic presentations.

One of the regulatory processes currently under aggressive investigation as a causative agent both in islet cell dysfunction, i.e., insulin production, and in insulin signal mediation, i.e., insulin sensitivity and resistance, is the encoding for and genomic control of glutamine-fructose-6-phosphate aminotransferase (GFAT) (Shankar et al., 1998) (see FIG. 4). As described in the introductory remarks to Example II, this enzyme is the limiting gateway for the production of glucosamine (McClain and Crook, 1996). GFAT overexpression leads to overproduction of glucosamine and the subsequent disruption in cell signalling, caused by over-glycation in the transduction mechanisms for growth factor, transporter, and receptor protein biosynthesis, and ultimately mediates the toxic effects of hyperglycemia and insulin resistance, the hallmark of both IDDM and NIDDM. GFAT is expressed in most human tissues involved in the development of late diabetic complications, such as adipose and skeletal muscle where the effects of insulin resistance are most acutely manifested (Nerlich et al., 1998). It is also strongly expressed in vascular smooth muscle cells, nerve sheath cells, and in mesangial cells, where glucosamine mediated disruption of signaling pathways can be explained as the pathomechanic link between hyperglycemia and the overt vascular, motor, and renal pathology of diabetes.

The potentially pivotal role of GFAT has triggered numerous investigations in the development of anti-diabetic agents targeted at GFAT molecular, genetic patterns of expression (McKnight et al., WO 93/21330, 1993; Ammon et al., 1996; Nishi et al., EP 0 824 149 A2, 1998). In this present invention, the focus is on a more physiological and phenotypically utilitarian approach based on direct evaluation of glucosamine production and disposal capacity, rather than on genotypic assessments. The method of the invention is also a dynamic one, dependent on measuring an individual's capacity to maintain glucosamine homeostasis and not just dependent for significance on measurements of a static nature, as exemplified by the kinds of serological tests in current use for just measuring glucosamine titers in individual tissues. The daily balance of synthesis and metabolism of glucosamine can be gauged by the simple expedient of using two metaprobes simultaneously: one for the purpose of determining the relative conversion of glutamine into glucoseamine via GFAT and another to serve as an index of the relative turnover of the glucosamine reservoir in the body, including all of the storage pools, whether of de novo biosynthetic or dietary origin, in glycoproteins and the many subsequent metabolites of glucosamine's incorporation into other metabolites after its acetylation via the NAT gateway enzyme system.

Figure 12B:
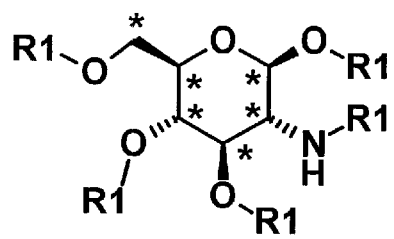
FIG. 12b depicts an exemplary set of metaprobes for glutamine fructose-6-phosphate amidotransferase (part 2)

Thus, for tracing glucosamine synthesis, the preferred metaprobes, shown in FIG. 12a, consist of glutamine and its analogs comprising the tracer core, with a 5-$^{15}$N-amide serving as the release tag and suitable derivatizing moieties at the 2-amino and carboxyl terminus, designed so as to insure a sufficient plasma half-life and subsequent delivery of intracellular glutamine. Such candidate derivatized forms of glutamine include N-acyl-conjugates with fatty acids and amino acids, carboxyl esters, carboxyl amides, and the other derivatives that are suitable carboxyl masking agents, as previously described in Table 4. The second metaprobe applied in this example to the NAT gatway consists of glucosamine itself, labeled with one or more $^{13}$C-atoms as the release tag, although deuterium and oxygen isotopes may also be employed, and functionalized into a carrier complex by N- and/or O-acylation, the preferred embodiment being N-acetyl-glucosamine itself, as shown in FIG. 12b: This class of NAT metaprobe is intended to quantify the fate of glucosamine during biochemical events taking place after the point of synthesis at the GFAT gateway.

In the course of glucosamine synthesis, a measurable proportion of the $^{15}$N-release tag from glutamine is transferred to glucosamine, and the extent of release incorporation into glucosamine becomes a measure of glutamine utilization by GFAT. The resulting $^{15}$N-glucosamine then undergoes a complex series of subsequent metabolic transformations beginning with acetylation and subsequent transacetylation via NAT, progressing through the many stages of protein glycation, and ending with excretion into urine as a distinct class of end stage metabolic conjugates. Among these, the aspartyl-N-acetyl-glucosamine pyranoside (Maury, 1981) and the bile acid (glycocholic and taurocholic) glucosaminides (Marschall et al., 1989) are the more plentiful ones that are amenable to isotopic analysis by readily available mass spectral techniques. Accordingly, the second metaprobe to be co-administered, namely an analog of pre-formed N-acetyl-glucosamine itself and a substrate for the NAT gateway enzyme, bearing a $^{13}$C or another different isotopic release tag other than the one incorporated into the GFAT metaprobe, serves as an indicator for the size and extent of the existing glucosamine pools and their turnover rates once past the gateway of its initial transaminative biosynthesis. The NAT metaprobe shares the same metabolic fate as the newly synthesized $^{15}$N-product and then is excreted in the same manner, thereby affording a means by which de novo production can be normalized to the subsequent turnover of similar, but pre-formed material. The combination of the two metaprobes, where a) the product of a first gateway is then b) the precursor for another gateway in a sequence that c) culminates with the isotopic release tags of both being analyzed in a common excreted fraction, permits the computation of one or more suitable GFAT metabolic rate indices (GFAT-MRI) that can be normalized to background NAT gateway activity. These indices may be the result of compartmental modeling, conceptually along the lines described in Example VI, or a simple numerical expedient in which the fraction of the dose recovered from the GFAT (glutamine) metaprobe, i.e., the $^{15}$N-content in the urinary conjugate fraction, is normalized to the fraction of the dose recovered from the NAT (N-acetyl-glucosamine) metaprobe, i.e., the $^{13}$C content in the same excreted fraction.

The following two experiments are illustrative of the method and provide initial evidence of its feasibility as a method of metabolic tracing for GFAT in vivo by means of two distinct metabolic rate indices (MRI1 and MRI2). In the first experiment, six male Sprague-Dawley rats, weighing on average 300 grams, were studied while awake and unstressed after an overnight fast. N-acetyl-5-$^{15}$N-glutamine at a dose of 30 mg/kg and N-acetyl-1-$^{13}$C-glucosamine at a dose of 5 mg/kg were prepared as a 10% (w/v) solution in 10% aqueous fructose corn syrup delivered by gastric intubation in four portions over a half hour period. Food and water were then given ad libitum. After receiving the metaprobes, the animals were kept in metabolic cages to facilitate collection of urine (Robinson, 1968). After 24 hours, the urine was concentrated by lyophilization, subfractionated by solid phase extraction on Sep-Pak C18 to obtain total bile acids, and then chromatographed by ion exchange to obtain the fraction of amidated bile acid glycosides. These were then hydrolyzed with N-acetyl-glucosaminidase and snail glucosidases according to literature procedures (Marschall et al., 1989).

The resulting glucosamine fractions were analyzed by combustion isotope ratio mass spectrometry in a calibrated system designed for conducting simultaneous mass balance studies on biological extracts of urine labeled with $^{15}$N and $^{13}$C (Browne et al., 1993, 1997). The percent of metaprobe dose recovered as $^{15}$N, indicating relative de novo glucosamine synthesis, was 0.036+/−0.015. The percent recovery of $^{13}$C, indicating the relative dilution space for the N-acetyl-glucosamine metabolite, was 0.15+/−0.073. The resulting normalized $^{15}$N/$^{13}$C GFAT-MRI1 is then calculated as 100×0.036/0.15=24. Accordingly, any statistically significant elevation in this index would be evidence of excessive GFAT activity and could be evaluated longitudinally over the life history of disease treatment or in response to glucostatic challenges. Variations from normative values for control subjects in IDDM and NIDDM would be followed in a similar manner.

In a second experiment, a normal, 75 kg male subject, 48 years old, with normal blood glucose and triglyceride levels after an overnight fast, was dispensed an oral dose of 600 mg of N-acetyl-5-$^{15}$N-glutamine and 100 mg dose of N-acetyl-1-$^{13}$C-glucosamine once an hour for four hours. The tracers were ingested each time with 100 ml of a 10% aqueous solution of high fructose corn syrup. Urine samples were collected at 12, 24 and 36 hours. Analysis for the aspartyl-N-acetyl-glucosamine pyranoside by combined gas chromatographic/mass spectrometric analysis (Maury, 1981) revealed an average urinary concentration of 1.8+/−0.3 mg/Liter. Fragmentographic evaluation of the derived ion spectra, in comparison to reference spectra of individually labeled reference standards, indicated that both $^{15}$N and $^{13}$C were present in the urinary fractions. As in the previous demonstration of applicability, the relative recoveries of the two tracer release tags were expressed in terms of the $^{15}N/^{13}C$ ratio multiplied by 100, in order to obtain the normalized MRI2 values, shown in Table 9. The analysis of each urine sampling interval was carried out in triplicate and the variation among replicates fell within 15%. These data indicate an equilibration of the two tracer species after 24 hrs. and that a basal GFAT MRI2 can be computed within that time frame from a convenient oral dosing protocol in vivo. Also, since aspartyl-N-acetyl-glucosamine pyranoside is rapidly synthesized and subsequently turned over by lysozomes, its rate of appearance in plasma can be determined, along with the plasma rate of appearance of N-acetylglucosamine, at shorter intervals post dosing. Thus, the MRI2 index could be computed within reach of the two-hour preferred sampling time frame for the practicable implementation of diagnostic procedures with metaprobes.

This second approach and its variations in form of dosing, e.g., oral or intravenous, and site of sampling, e.g., plasma, selected blood fractions or urine, also represents a method whereby GFAT overexpression can be traced by virtue of its metabolic, rather than its genomic, signature. Identification of that signature prior to the onset of overt diabetic symptoms and subsequent modulation of that signature's magnitude by means of antidiabetic treatments, whose efficacy is titrated in step with changes in the GFAT metabolic rate indexes, are demonstrably obtainable objectives using the methods of the invention for probing gateway enzyme pathways.

TABLE 9

GFAT metabolic response index (MRI2) in human urine

| TIME POINT (hr) | 15N % Dose | 13C % Dose | Metabol. Resp. Index |
|---|---|---|---|
| 12 | .016 | .089 | 18 |
| 24 | .035 | .189 | 19 |
| 36 | .047 | .213 | 22 |

Based on the derivation of the MRI2 in Table 9, it is easily envisioned that a comprehensive set of MRI values for GFAT overproduction can be established, for example, by gender and by 5 year life history in asymptomatic individuals. These normative values would be available to clinicians for subsequent comparison and contrast to corresponding ones taken from individuals presenting with diabetes, both before and after the onset of diabetic complications. A normative, natural history of GFAT activity through the course of adult life, or as a function of life style and putative exposure to the effects of oxidant stress, would then form a part of the decision making mechanisms in patient care as a prognostic index for future outcomes that are correlated with prematurely high GFAT MRI values.

EXAMPLE IX

Cellular Pathways Containing Gateway Enzymes and Their Associated Disease States of the Immune System The gateway enzymes described in the preceding examples II–VIII are structurally and functionally associated with discrete organ systems, such as liver, kidney, pancreas, gut, lung or tissues associated with discrete anatomical sites, such, as the vascular endothelium and smooth or striated muscle. By contrast, the immune system is an equally important homeostatic and allostatic effector that cannot be pinpointed to any particular organ structure or tissue but is generally thought of as an adjunct to the circulatory and lymphatic systems interconnecting all organs and serving as a front line for the expression of innate and adaptive immunity (Houston, 1997).

It has become clear in the last decade that proteolysis, the degradation and recycling of both structural and regulatory peptides and proteins, is a special mechanism of epigenetic control over cell function and programmed cell death (apoptosis) in all areas of immune system function as well as in inflammatory and neoplastic diseases affecting the circulatory, musculo-skeletal, and neurologic systems. Cellular proteases mediate natural (non-specific) as well as acquired (specific) immunity, and in many instances serve as gateway enzymes to these processes, as constitutive entry or end-points in a cascade of events, as regulatory bottlenecks, and, if unchecked by endogenous or pharmacological inhibition, as the agents for life-threatening, cell-signalling storms. Thus, cellular peptidases are involved in the cognitive phase (viral, bacterial and auto-immune antigen presentation and processing), in the covert activation phase (transcription factor processing; generation and regulation of chemokines, cytokines, growth factors, hormones), as well as in the overt effector phase leading to pathophysiological symptom presentation, as illustrated in part by FIG. 13 (Ansorge and Langner; Goding and Howard; Skidgel and Erdos). Referring to FIG. 13, tissue injury or bacterial or viral antigen presentation activates leucocytes and lymphocytes via membrane receptors, several of which are functionally connected to the activation of cellular peptidases on the cell surface and contained membrane vessicles. Activation or expression of these peptidases mediate the concomitant structural transformations necessary for cell adhesion (protein hydrolysis) and chemokine secretion. Further biochemical action at the inflammatory site, involving cell lysis, phagocytosis, autocrine, and paracrine stimulation are effected by cellular proteases in response to changes in metal ion titers, pH, and phosphorylation. The differentiation antigens CD10, CD13, CD26, CD143 (angiotensin converting enzyme), BP1/6C3, and MAX1/MAX11 are also ectoenzymes on cell surface of lymphoid cells (Goding and Howard).

An outstanding property of these types of cellular peptidases is their propensity for cleaving peptides and proteins at specific sites towards which they are directed by the presence of the amino acid, proline (Cunningham and O'Connor; Sedo et al.; Van Hoof, et al). This selectivity towards the proline motif, shown in FIG. 14, has permitted the study of these gateway enzymes by means of specific substrates containing proline at various positions, which are otherwise impervious to hydrolysis by less specific proteases, including other gateway enzymes which do not recognize the proline motif at their active sites. Such an evolutionary coincidence, however, takes on considerable importance in a diagnostic and therapeutic context, because the proline motif is found at, or one site removed from, the N-terminal of many cytokines and growth factors Table 10). It is also prevalent at key regulatory points within the structure of neuro- and vasoactive peptides and hormones (Table 11) and in effector peptides, shown in FIG. 15, both pro-thrombotic and thrombolytic, of the coagulation cascade (Table 12). Under inflammatory conditions, such as sepsis, the disseminated intravascular cascade is modulated by the actions of peptidases, marked as scissors, which otherwise would not participate significantly as regulators under normal conditions for this process. The upregulation of these peptidases during immune system disregulation alters the processing rates of key pro-thrombotic and thrombolytic enzymes including thrombin and plasmin (Levi et al.).

TABLE 10

Cytokines and Growth Factors Regulated by Gateway Enzymes

| Target Peptide | Proline (PRO) Sequence in Target Motif |
|---|---|
| Erythropoietin | ala-PRO-PRO |
| Granulocyte stim factor | ala-PRO-ala (macrophage colony) |
| | thr-PRO-leu (colony) |
| Granulocyte chemotactic protein | gly-PRO-val |
| Growth hormone | phe-PRO-thr |
| Insulin-like growth factor | gly-PRO-glu |
| Interferon inducible protein 10 | val-PRO-leu |
| Interleukin-1beta | ala-PRO-val |
| Interleukin-2 | ala-PRO-thr |
| Interleukin-5 | ile-PRO-thr |
| Interleukin-6 | val-PRO-PRO |
| Interleukin-10 | ser-PRO-gly |
| Interleukin-13 | gly-PRO-val |
| Lymphotoxin | leu-PRO-gly |
| Prolactin | leu-PRO-ile |
| Melanoma growth stimulating factor | ala-PRO-leu |
| Monocyte chemotactic protein | glu-PRO-asp |
| Tumor necrosis factor-beta | leu-PRO-gly |

TABLE 11

Neuro- and Vasoactive Peptides Regulated by Gateway Enzymes

| Target Peptide | Proline (PRO) Sequence in Target Motif |
|---|---|
| Angiotensin | his-PRO-phe |
| Bradykinin | arg-PRO-PRO |
| | ser-PRO-phe |
| Calcitonin | phe-PRO-gln |
| | gly-ala-PRO (NH2) |
| Casomorphin | tyr-PRO-phe |
| | phe-PRO-gly |
| Corticotropin releasing hormone | glu-PRO-PRO |
| Gastrin releasing peptide | val-PRO-leu |
| | leu-PRO-ala |
| Luteinizing hormone releasing hormone | arg-PRO-gly(NH2) |
| Neuropeptide Y | tyr-PRO-ser |
| | lys-PRO-asp |
| | asn-PRO-gly |
| | ala-PRO-ala |
| Neurotensin | lys-PRO-arg |
| | arg-PRO-tyr |
| Oxytocin | cys-PRO-leu |
| Pancreatic polypeptide | ala-PRO-leu |
| | leu-PRO-val |
| | tyr-PRO-gly |
| Peptide YY | tyr-PRO-ile |
| | lys-PRO-glu |
| | ala-PRO-gly |
| Substance P | arg-PRO-lys |
| | lys-PRO-gln |
| Thyrotropin | phe-PRO-asp |
| Thyrotropin releasing hormone | pglu-his-PRO(HN2) |
| Vasopressin | cys-PRO-arg |

TABLE 12

Coagulation Cascade Peptides Regulated by Gateway Enzymes

| Target Peptide | Proline (PRO) Sequence in Target Motif |
|---|---|
| Basic trypsin inhibitor | arg-PRO-asp |
| Factor V | PRO-leu-ser |
| | ser-PRO-arg |
| | his-PRO-leu |
| Factor VIII | gly-PRO-arg |
| | ser-PRO-arg |

TABLE 12-continued

Coagulation Cascade Peptides Regulated by Gateway Enzymes

| Target Peptide | Proline (PRO) Sequence in Target Motif |
|---|---|
| Factor XII | ile-PRO-PRO |
| Factor XIII | val-PRO-arg |
| Fibrinogen | gly-PRO-arg |
| Protein C | asp-PRO-arg |
| Prothrombin | thr-PRO-arg |
| | Asn- PRO-arg |

It follows that numerous techniques in the repertory of ex vivo clinical chemistry, immunochemistry and cytology have been developed to track the course of cellular processes involving both the effector enzyme and their endogenous substrates. These have been disclosed in numerous patents, the following being the most representative and whose teachings in general about peptide substrate design rationale and synthetic implementation, and in specific with regard to utility, are incorporated herein by reference. Prior art disclosures for the assay ex-vivo of soluble, cellular peptidases, including those specific to the proline motif, include Aurell, et. Al.; Blomback et al.; Claeson, et al.; Ekenstam et al.; Gargiulo, et al.; and Svendsen, et al. More recent work directed at the localization and titration of membrane bound cellular proteases in tissue preparations taken ex vivo in the diagnosis and management of diseases stemming from immune system derangement is given by Lucas, et al. and Jaffe, et al. The principle of operation for the protease assay in these instances of prior art all involve the release of a light absorbing or fluorescent indicator dye from the peptide substrate subsequent to the hydrolytic action of the target protease. These indicators by their very chemical nature as biological stains are hazardous xenobiotics unsuited for use in vivo.

By analogous reasoning to the teachings of these precedents with regard to molecular configurations and synthetic chemistry, this invention discloses the design of a series of metaprobes with the proline and related motifs as the core tracer. But in contradistinction to prior art, and consistent with the reasoning elucidated in the preceding Examples III–VIII of this invention, the release tag in this invention is a tracer labeled molecule that is both biologically safe and whose metabolic release in vivo can be traced in accordance with the teachings of Example I. This latter approach is a novel and unclaimed application of structurally targeted enzymological metaprobes, whose rates of hydrolysis in vivo can be utilized as a quantifying indicator of gateway enzyme activity, for example in lymphocyte and other blood cell function following trauma, wound healing, inflammation, sepsis, transplant rejection, and autoimmune disorders (Faist and Kim; Levi et al.; Shaffer and Barbul).

The gateway enzymes relevant to both homeostatic and pathophysiological processes, which shall be illustrated in subsequent examples, include the dipeptidyl N- and C-terminal peptidases, which also serve as leucocyte cell surface antigens and various stages of immune system activation; the intracellular, cytosolic or granulocytic, regulatory or apoptotic, peptidases; and the principal effectors of blood clotting or clot dissolution. The diseases associated with these processes can all be monitored by their biochemical signatures as embodied both in metaprobe test scores elaborated in accordance with the generic protocol described in Example I and in accordance with many of the same procedural variations illustrated in prior Examples III–VIII.

EXAMPLE X

Use of the Method of the Invention with Dipeptidyl Peptidase IV (DPPIV)

In the last 10 years, several innovative paradigms have emerged for following the "natural history" of the immune system's activation in response to autoimmune genetic disregulation (Estess, et al.), carcinogens, and mitogens in bacterial and viral infections (Morimoto and Schlossman). These are posited on the use of immunocytochemistry or immunohistochemistry, are being extensively validated and have garnered both factual and editorial validation. It is also generally accepted that wound healing and recovery following injury are processes overwhelmingly dependent upon lymphocyte defense mechanisms (Schafer and Barbul).

One of the most versatile indicators of lymphocyte activation is the accessory glycoprotein known as DPPIV, which is also the cell differentiation antigen CD26. It is a multi-functional molecule with unique enzymatic activity and substrate specificity unaffected by crossreactivity with other proline selective hydrolases. It selectively cleaves amino terminal dipeptides with proline (or alanine) in the penultimate position, and the expression of this hydrolytic capacity appears in step with the life history of the CD4+ helper/memory population. DPPIV is also active, but to a lesser extent, in B and NK cells. Moreover, considerable evidence has been marshaled to demonstrate that DPPIV interacts with both CD45, a regulatory protein tyrosine kinase, and serves as the binding site for adenosine deaminase (ADA), each of which function as potent signal transduction mechanisms. The latter is especially associated with the regulation of immune surveillance in oncogenesis and in HIV infection (Schmitz et al.)

The composite picture emerging from an extensive literature on DPPIV suggests that it should serve as an ideal biomarker for disease status, functional surrogate end-point for therapeutic intervention, and platform for integrative biology, because in disease its expression and, therefore, enzymatic capacity become significantly elevated over basal levels. Beyond its direct role in immune system activation, DPPIV participates in functions ancillary to immune system conditioning. These include peptide hormone activation, peptide absorption, lymphokine and chemokine processing, intestinal and renal transport of proline and collagen metabolism (by virtue of its hydrolytic activity), and epithelial, myeloid and lymphoid cell cycle regulation (Ansorge and Langner, Chapters 15–28; Barrett et al., Chapter 266; Fleischer,).

Prior art addressing methodology for the quantitation of DPPIV, and its related gateway enzymes as shown in Tables 1–3, has been posited almost exclusively on ex vivo techniques. For example, there are many definitive as well as reference methods for assaying lymphocyte function, and a brief review needs to be set forth in order to highlight the novelty of this inventions's aims and objectives. It is universally agreed that the function of B lymphocytes can be quantitated by measuring the level of specific antibody in bodily fluids, such as blood, saliva or urine. This approach stands as one of the foundations of modern clinical chemistry, but, as such, it remains an ex-vivo technique, providing a snapshot of immunological status at a given point in time. There are no dynamic assays for B cell function in vivo.

Measurement of the functions of T-lymphocytes or T-cells is also conducted ex-vivo, and with the added complications that there are many different subsets of T cells with different functions.

Immunofluorescene microscopy, immunocytochemistry, enzyme immunoassay and flow cytometry are the benchmark techniques in this context, but the major difficulty with all these ex vivo cell counting techniques remains associated with the fact that they do not measure function, cell response, or capacity.

The discovery of lymphocyte activation and recognition antigens possessing concomitant enzymatic activity, most notably DPPIV/CD26, has advanced the possibilities for development of hybrid cytological reagents, namely, enzyme substrates that then release readily measurable chromophores (fluorophores) upon hydrolysis. These reagents are now routinely available from laboratory supply houses and have become the basis for an extensive proprietary library of indicator compounds applicable towards assaying the activity of several enzymes simultaneously inside a metabolically active whole cell. In fact, these types of reagent have revitalized the field of flow cytometry. The latter has spawned numerous patents on the development of surrogate end-points for either "well-ness" or disease severity based on profiling and quantitating the enzymatic function of the various components in the immune system activation cascade (Lucas, et al., Jaffe, et al.).

Beyond advances in what remains fundamentally a form of clinical chemistry, there have been no applications to date of in vivo probes patterned after the mode of function already demonstrated.

By means of this invention it is possible to transfer and optimize a blood-product oriented clinical chemistry technology into the physiologically more relevant in vivo setting, where questions about functional capacity, reserve and "potential" can then be directly addressed and correlated to clinical presentation. While minimally invasive, this new methodology is expected to provide a metabolic (kinetic) signature for the DPPIV activity on a whole body basis, rather than solely from its more accessible plasma component. While the significance of plasma assays can be impugned on the grounds that analytes ex vivo are by definition "inactive", such a judgement cannot be leveled at an in vivo bioassay of the kind disclosed here.

With regard to economics, the approach taken in this invention is also intended to yield cost-effective and competitive solutions. The characterization of immune system parameters even by today's advanced standards is still a composite exercise, with multiple combinations of measurements involving not only the techniques described earlier but also more intensive procedures drawn from the armamentarium of molecular biology (PCR). None are what in the medical profession would be deemed "stat" procedures that can be conducted at the bedside. This goal is indeed attainable via the application of metaprobes, as described in Example I, at a delivered cost comparable to that of clinical chemistry assays, a figure that is more than competitive with the aggregate cost of serology and cytology aimed at analytes of similar complexity to the DPPIV system.

Moreover, a typical immune system work-up by conventional clinical chemistries often involves a multiplicity of seemingly disconnected measurements which must be integrated by means of an expert system into a single judgement score. A battery of tests is certainly called for in any approach towards defining systemic inflammatory responses, especially if complicated by multiple organ dysfunction. This invention, focused on the activity of the DPPIV gateway enzyme, represents an advancement over prior art because the function of DPPIV, in connection with the differentiation of T-cells (Th-1) itself is the integrator of multiple effects. Thus, the process of tracing its temporal properties in vivo then provides an effective leveraging of relevant information about changes in T-cell mediated immune system status.

With regard to probing the activation response of lymphocytes in vivo by this sequence of steps, this invention adapts the substrates already used so effectively in serology and cytology so as to preclude adverse toxicology while at the same time replacing the chromophoric "release" tag with a non-radioactive tracer.

As shown in FIG. 16, Panel A, in the classical configuration, a benchmark substrate is the Glycyl-Prolyl-4-nitro-anilide (GP4NA, I). It is cleaved by DPPIV into 4-nitroaniline (II) and the latter quantitated by absorption spectrophotometry. For purposes of fluorescent flow cytometry, also from prior art, GP4NA may be substituted by rhodanine, aminocoumarin, cresyl violet, fluorescein and related dyes.

In this invention, the GP4NA leaving group, or its congeners, are substituted with a biologically safe release tag in accordance with the design rules for metaprobes, and shown in panel B. One such release tag, embodied in structures III of FIG. 16 and referred to as gylcyl-prolyl-p-aminobenzoic[1-$^{13}$C] acid (GPPaba), Panel B, is comprised by the family of suitably protected $^{13}$C, $^{15}$N or deuterium tracer labeled forms of p-aminobenzoic acid, a biologically safe vitamin suitable for in vivo use as a release tag. The requirements for an arylamine group as the scissile amide at the P1-P1' peptide junction can also be satisfied by suitably protected p-aminohippuric acid, p-amino salicylic acid, 4-amino-tyrosine and other non-toxic, non-metabolizeable but rapidly excreted organic acids.

A second, and more practical release tag is the $^{13}$C-carbonyl moiety of the 2-aminobutyrate amino acid core tracer, shown attached to the glycyl-prolyl carrier complex in structure V, with its free carboxyl protected also in accordance with the methods already illustrated in previous examples. Thus, the application of a suitably protected glycyl-prolyl-2-aminobutyric[1-$^{13}$C] acid (GPA) as an in vivo breath test substrate for DPPIV still exploits the extremely narrow and specific substrate selectivity of this serine ecto-peptidase, namely, to accomplish the cleavage of Pro-X bond in an N-terminal Gly-Pro-X tripeptide (V). However, the functional group X at scissile P1-P1' amide junction is now replaced with a rapidly metabolized substrate, i.e. a non-radioactive carboxyl labeled amino acid (VI), that releases $^{13}CO_2$ upon subsequent oxidation. It follows, as shown in FIG. 17, that this release tag may be incorporated into any rapidly metabolized amino acid which satisfies the structural requirements for the P1' group at the S1' active site of DPPIV. These include the aliphatic and aromatic amino acids and, preferably, those which are most rapidly metabolized to $^{13}CO_2$.

For the initial proof of concept, it was proposed that X should be a non-proteinogenic amino acid, so as not to introduce a confounding variable related to whole body protein synthesis. L-2-aminobutyric[1-$^{13}$C] acid (VI) was therefore selected on the grounds that, when liberated from the tripeptide (V), it would be expected to transaminate rapidly and yield $^{13}CO2$ upon the subsequent oxidative decarboxylation of its derived 2-ketoacid. (L-2-aminobutyric acid and its derived keto acid are by-products of the conversion of methionine to cysteine via cystathionine and whose rapid disposal is a matter of biochemical record, as documented in Example 7).

Three experiments have been performed to demonstrate the potential for the proposed DPPIV metaprobes, and in particular the breath test metaprobe just described and shown as structure V in FIG. 16. The general design and implementation of these experiments also should be taken to be illustrative of the approach towards implementing metaprobes for any of the gateway enzymes disclosed in Example 9, as they encompass all the generally applicable principles for peptide design, synthesis and testing:

a) Structure Activity and Chemical Synthesis

Drug discovery is now a computerized effort and the resources for simulating enzyme-substrate interactions are readily available. A model of the active site domain for the CD26 dipeptidyl-peptidase functionality was implemented in accordance with the published formalisms of Brandt and colleagues (and citations 25–27 therein). The original MOPAC/SYBYL coding was ported to the ChemistrySW Molecular AnalysisPro and Molecular ModelingPro (ChemistrySW, Fairfield Calif.) environment for use in a Windows based workstation environment. Ligand docking and energy minimization studies confirmed the choice of the Gly-Pro-Abu (GPA) metaprobe and of the Gly-Pro-PABA (GPPaba) as an adequate substrates, whose transition state would be comparable thermodynamically to the benchmark nitrophenolate probe.

It should be noted that this approach not only can be employed to confirm the suitability of lead discovery but also as a direct aid in the design of new analogs themselves. For example, in addition to optimizing the selection of the core tracer, which in this case is Abu linked to the tracer carrier dipeptide by a scissile bond, molecular modeling can be used to determine which alternative peptidomimetic substituents might be incorporated into the peptide tracer carrier so as to obviate the presence of supernumerary scissile bonds between constituents other than those at the intended, P1-P1', site of cleavage.

It would be desirable in this and other instances of metaprobe design, to preclude the adventitious hydrolysis of the metaprobe by enzymes other than the intended target of the metaprobe. Specifically with regard to the metaprobes of this example, shown in FIG. 15 as structures III and V, it would be desirable to modify the glycyl-proline linkage, at the P2-P1 junction, in such a way as to make it impervious, or at least less susceptible, to hydrolysis by N-terminal amino peptidases, capable of removing amino acid groups from the N-terminus independently of DPPIV's activity at the C-terminus. Numerous approaches for accomplishing this latter objective are known to those practiced in the art of peptide and peptidomimetic drug development, and they are incorporated here by reference (Abell; Babine and Bender; Dolle; Hu et al.; Kazmierski; Sandler and Smith). The synthetic procedures described in Kazmierski's compilation of laboratory methods are particularly relevant in this context. In addition, substitution of the glycine moiety at the P2 site with other amino acid analogs, as well as substitution of the proline at the P1 site with its higher or lower cyclic homologs or by its heterosubstituted isosteres, also can be expected to render a more stable metaprobe towards adventitious hydrolysis, while preserving or enhancing its activity as a substrate for the target enzyme. These considerations are embodied in the structures shown in FIG. 17 as encompassing the preferred embodiments in this example.

Synthesis of the GPPaba (FIG. 16, structure III, with R1 being the free acid) was accomplished by traditional peptide coupling with dicyclohexylcarbodiimide under 4-dimethylamipyridine and triethylamine catalysis in methylene chloride (Bodanszky and Bodanszky). Commercially available Gly-Pro (Bachem), protected as the tBoc, and p-amino-benzoic[1-$^{13}$C] acid (by cyanation of the corresponding arylbromide with $^{13}$C-cyanide under copper catalysis), protected as the t-butyl ester, were used as reagents. After deprotection, the tripeptide was purified by ion exchange and crystallization from ethyl acetate, affording chromatographically homogenous material in 55% yield and conforming to the expected spectroscopic (NMR) and mass properties (MS/MS direct probe insertion and elemental composition: C 57.43%, H 5.42%, N 14.19%).

Synthesis of the GPA metaprobe (FIG. 16, structure V, with R1 being the free acid) was accomplished by traditional peptide coupling via the isobutyl chloroformate activation route (Bodanszky and Bodanszky). Commercially available Gly-Pro (Bachem), protected as the tBoc, and L-$^{13}$C-Abu (by amidocarbonylation of acetaldehyde with $^{13}$CO followed by acylase resolution), protected as the methyl ester, were used as reagents. After deprotection, the tripeptide was purified by ion exchange and crystallization from ethyl acetate, affording material in 65% yield and conforming to the expected spectroscopic (NMR) and mass properties (MS/MS direct probe insertion and elemental composition: C 51.63%, H 7.37%, N 16.19%).

b) In-vitro Enzyme Assay

Dipeptidyl peptidase reference enzyme was purchased from Sigma-Aldrich (D7052) and assayed by the standard Michaelis-Menten method described in similar studies by Barth and co-workers (Heins, et al.; Rahfeld, et al.). The apparent $K_m$ value for the GP4NA substrate (also from Sigma) was found to be 0.13 mM. A comparable figure of the same order of magnitude, 0.2 mM (average of 2 determinations at 4 concentrations) was found for the GPA tracer metaprobe. Hydrolysis of the latter was quantitated by isotope dilution GC/MS of the N-trifluoroacetyl-propyl ester, using L-2-aminobutyric[$^2$H$_5$] acid as the internal standard.

c) In-vivo Assay

The septic rat model affords a suitable biological platform for testing the hypothesis that a complex process can be characterized by tracing the upregulation of the DPPIV/CD26 lymphocyte activation response. This animal model has been validated extensively in the clinical nutrition field, with studies of protein dynamics and muscle wasting (Voisin et al.). It was also available for this pilot work as part of an on-going effort to study various aspects of sulfur amino acid metabolism, including the fate of L-$^{13}$C-Abu derived endogenously from methionine tracers. Because the septic rat is known to rapidly oxidize branch-chain amino acids, the use of a tracer protocol in which L-$^{13}$C-Abu is derived endogenously by hydrolysis would be expected to afford measurable amounts of $^{13}$CO$_2$, as the predicted end-stage metabolite suitable for quantitation.

Accordingly, ten male Sprague-Dawley rats, weighing approximately 300 gr., were injected with 3.5 mg/kg of GPA (prepared by sterile ultrafiltration in saline) and placed into metabolic cages for $^{13}$CO$_2$ collection (by alkaline trapping in seven 0.5 hour increments), in general as described by Vann et al. A blood draw of 0.4 ml was taken prior to the tracer administration to provide a baseline plasma titer for in vivo DPPIV activity. The following day, the rats were separated into a control panel and a test panel. Each of the three animals in the test panel was made septic (on Day 0) by intravenous (tail vein) adminstration of E. coli. Three control animals were sham injected with saline, and all were maintained in separate cages.

On day 2 and 6, and after a 0.4 blood draw, the administration of the "breath test" metaprobe and $^{13}$CO$_2$ collection was repeated. Equal aliquots of plasma were assayed for enzyme activity by spectrophotometry in two ways: a) using GP4NA (FIG. 16, structure I), a traditional and confirmatory approach, and b) using GPPaba (FIG. 16, structure III with R1 being the protonated free acid) by GC/MS quantitation of the p-aminobenzoic[1-$^{13}$C] acid (Paba, FIG. 16, structure IV) derived hydrolytically. The isotopic enrichment of the seven breath collections was measured by isotope ratio mass spectrometry, of the gas liberated after phosphoric acid protonation. The cumulative extent of metaprobe metabolism, as a per cent of dose taking into account the total CO$_2$ production rate of each animal (Mohan et al.) was then calculated. The results are shown in Table 12.

Also, over the 7 day experiment, the specific activity of plasma towards GP4NA in the control group averaged 29±6 nMol/min/ml while the septic titer rose to 43±7 and 49±6 on days two and six, respectively. The corresponding values of plasma activity towards GPPaba in the control group averaged 18±7 nMol/min/ml while the septic titer rose to 55±17 and 30±6 on days two and six, respectively. A "sham" breath test using 1.5 mg/kg administration of L-2-aminobutyric[1-$^{13}$C] acid in saline on day 3 of the experiment confirmed that oxidation of the release tag was similar in control and test groups, affording a cumulative oxidation of 65±8.3 and 72±9.4 per cent of dose recovery in 3 hours, respectively.

TABLE 13

DPPIV Metaprobe Metabolism in the Septic Rat Cumulative Per Cent of Dose Exhaled in 3 Hours

|  | CONTROL (n = 3) | SEPSIS (n = 7) |
| --- | --- | --- |
| Day 1 | 4.3 (± 0.8) | 5.7 (± 1.4) |
| Day 2 | 8.9 (± 1.3) | 22.5 (± 5.3) |
| Day 6 | 4.9 (± 0.8) | 9.2 (± 6.3) |

The results shown in Table 13 follow the general pattern of DPPIV elevation that has been associated with increased cellular CD26 expression in rats, for example, when the immune cascade has been triggered by allograft transplantation (Korom, et al.). It is known that the acute inflammatory response peaks at two days after insult, and then becomes chronic. The same pattern of inflammation has been observed in the septic rat model (Voisin et al.). In our pilot experiments, the increase in plasma DPPIV activity parallels the output in breath of the metaprobe, given intravenously and putatively also metabolized in plasma by dipeptidyl peptidase IV, roughly in step with the expected course of the underlying pathophysiology. The enhanced hydrolysis in-vivo by DPPIV enzymatic activity also follows the trend of increased plasma specific activity against a benchmark colorimetric substrate when assayed in-vitro at various intervals after the septic insult.

This observation suggests that, when optimized, a breath test with a substrate for DPPIV can indeed be used to follow the progression of a septic insult and, as such, would be a powerful tool yielding in vivo, what would otherwise have to be reconstructed from ex vivo plasma analyses. The experimental outcome also confirms the utility of the GPPaba tracer metaprobe as a diagnostic agent for DPPIV activity in-vivo, since its hydrolysis proved commensurate with that of GPA, the more conventional spectrophotometric probe.

EXAMPLE XII

Use of the Method of the Invention with Thrombin and Plasmin

Thrombin and plasmin are the two principal effectors of the thrombogenic-thrombolytic cascade and have been the subject of intense molecular and functional scrutiny for five decades, engendering a voluminous literature which has been succinctly summarized by Barrett et al (Chapters 55 and 59 and references therein). Thrombin pathophysiology is monitored routinely in cardiovascular care and, more recently, evaluation of plasmin and the ratio of thrombin to plasmin in the free and natural inhibitor bound form have become diagnostic standards in the management of cardiovascular interventions and critical care, for which an increasing number of anti-thrombotic or pro-thrombolytic therapies are in current use (Levi et al.; Vervloet et al.).

The most commonly used clinical chemistry laboratory procedures, aimed in current practice at characterizing the coagulation cascade in relative quantitative terms, are the thromboplastin time, the actived partial thromboplastin time (aPTT) and the thrombin clotting time (TCT) (Kher et al.). The principle of the PT is that it measures the time necessary to clot a plasma sample after recalcification and in the presence of excess tissue factor and pro-coaggulant lipid; that is, it tests for the time until onset of the clotting initiated by the extrinsic system. Unfortunately, the PT is not sensitive to the effect of heparin or other circulating anticoaggulant therapies, including those targeted at fibrinolysis, and therefore cannot serve as an indicator of the pathophysiological mechanisms operating in whole blood ex-vivo or in the circulatory system in-vivo.

The aPTT is also an indirect correlate of the clotting capacity of whole blood, representing instead the lag-phase before explosive thrombin generation in an intrinsically triggered plasma sample. It is a specific test for thromboplastin, sensitive to all disturbances of the intrinsic clotting system. It shows large interindividual variations and is strongly influenced by instrument and reagent dependent laboratory conditions. Moreover, as a management or prognostic tool on the risk of recurrent venous thromboembolism, the achievement of a therapeutic aPTT result within 24–48 hours post cardiovascular insult fails to correlate with prognosis or other clinical measures of anticoagulant therapeutic efficacy. Lastly, the TCT, a simpler test in principle, serves as a titration for the clotting capacity of thrombin in a plasma sample. It is a sensitive and specific test for the anti-thrombin effects of specific inhibitors of thrombin, especially heparin, but it is also influenced by fibrin degradation products, temperature, cation concentration and pH; so, TCT's use is the subject of continued dissention and is in disfavor.

Here, an illustrative analogy, may provide a way to underscore the problem with traditional in the quantification of coagulopathies. The PT and the aPTT are tests of the same vintage as that of plasma cholesterol measurements. Just as with the latter, it has become increasingly clear that a single static measure of concentration does not forecast the true risk factors, which in the case of cholesterol include the balance between lipoprotein fractions and their cholesterol content. So too it has become evident that a single "coagulation time" based test fails to integrate the confluence of simultaneous covert pro-coagulant and anti-coagulant events that constitute the overt manifestation of the coagulation cascade. This shortcoming and the heightened need for monitoring the effects of a rapidly evolving set of therapeutic management modalities, transcending the classical use of unfractionated heparin, have provided the impetus for development of a common, integrative parameter for quantifying the net effect in whole blood of the diverse elements in the coagulation cascade, especially in critical or intensive care settings, when disseminated intravascular coagulation is prevalent and undiagnosable by conventional techniques (Vervloet et al.).

A major step towards achievement of this goal has been accomplished with the introduction of the endogenous thrombin potential (ETP). The thrombin-generating capacity of plasma is one of the main determinants of hemostasis and thrombosis, and it can be determined by integrating the time course of the thrombin generating curve from the time of thrombin generation onset until exhaustion of the thrombin activity in the formed clot. By contrast, the traditional tests measure only the thrombotic capacity for the short period until the onset of clotting, neglecting the effects of thrombin's continued enzymatic potency on numerous substrates and its prothrombotic action long after clot formation. Thus, the ETP parameter provides the laboratory derived correlate of coagulation capacity, which decreases in drug induced hypocoagulability and increases in hypercoagulability even under conditions in which the PTT, aPTT and TCT are only marginally influenced (Kher et al., and references cited therein). Similar contrasting evidence, demonstrating the enhanced utility of the ETP, has been obtained in studies on anti-thrombogenic diets rich in n-3, but not n-6 polyunsaturated fatty acids (Nieuwenhuys et al.), in the evaluation of genetic polymorphisms in the prothrombin gene (Kyrle et al.), and in the response of women with antithrombin deficiency to steroid contraceptives (Wielders et al.)

In reviewing this prior art, as summarized throughout the recent definitive compilation of High and Roberts (1995), it becomes apparent that there are no tests applicable to whole blood or to an in vivo test for the determination of an equivalent measure of the ETP. Nor are there any such tests for independently measuring the total plasmin capacity or the net combination of the two.

In keeping with the design philosophy articulated in Example 10 and the general rubrics for metaprobe design followed therein, the separate teachings of Blomback, Eckenstam and Svendsen, taken as a whole, were adapted to afford metaprobes suitable for use in vivo with the same core tracers exploited in Example 10 (FIG. 16, structures 4 and 6) and shown in FIG. 18 as part of the completed structure for thrombin and in FIG. 19 for plasmin metaprobes.

a) Structure Activity and Chemical Synthesis

The substrate specificity of thrombin and plasmin share various homologies. The P2 site is selective for proline and its homologs and isosteres in the case of thrombin, but less so for plasmin, while the P3-P4 sites accept a variety of aliphatic and aromatic amino acids, among which phenylalanine and valine are the preferred for thrombin and leucine for plasmin. The significant difference lies in the nature of the P1 requirement, which in the case of thrombin shows optimal specificity for arginine in the S1 pocket, while lysine becomes optimal for plasmin. The scissile P1 to P1' bond requires a proper configuration, imposed by the P1' and any P2' and P3' groups so that the amide carbonyl is sufficiently proximate to the oxyanion hole of the reactive serine in the catalytic triad, while the amide nitrogen is sufficiently proximate to form hydrogen bonding with the acid-base donor histidine. Based in part on ligand-domain optimization and on requirements for release tag design, the preferred embodiments for thrombin metapobes were found to be the N-acetyl-d-phenylalanyl-L-prolyl-L-arginyl peptide of L-2-aminobutyric[1-$^{13}$C] acid and of p-aminobenzoic[1-$^{13}$C] acid, the latter two remaining protected as their corresponding ethyl esters. In a second embodiment, the d-phenylalanine moiety was replaced with glycine (Babine and Bender).

For plasmin the same two core tracers, with their $^{13}$C release tags, were combined with N-acetyl-L-leucyl-L-leucyl-L-lysine to afford the preferred metaprobe configuration.

The synthetic procedures followed the general outline and methodology, including the chromatographic and purification schemes, described by Blomback et al. For thrombin metaprobes: D-phenylalanyl-proline or glycyl-proline (Bachem) were acetylated with acetyl chloride and base in aqueous mixed media. The resulting dipeptide was treated with oxalyl chloride to afford the dipeptidyl acyl chloride which was then reacted with arginine. The resulting tripeptide was then coupled with the ethyl esters of p-aminobenzoic[1-$^{13}$C] acid or L-2-aminobutyric[1-$^{13}$C] acid by triethylamine and N,N-dimethylaminopyridine catalyzed dicyclohexylcarbodiimide dehydration. Chromatographic purification by ion exchange, short column gel chromatography and crystallization (methanol) afforded the desired end products:

I. N-acetyl-d-phenylalanyl-L-prolyl-L-arginyl-p-aminobenzoic[1-$^{13}$C] acid, ethyl ester
II. N-acetyl-d-phenylalanyl-L-prolyl-L-arginyl-L-2-aminobutyric[1-$^{13}$C] acid, ethyl ester
III. N-acetyl-glycyl-L-prolyl-L-arginyl-p-aminobenzoic[1-$^{13}$C] acid, ethyl ester
IV. N-acetyl-glycyl-L-prolyl-L-arginyl-L-2-aminobutyric [1-$^{13}$C] acid, ethyl ester For plasmin metaprobes, a similar approach was utilized to acetylate L-leucyl-L-leucine (Bachem) and combine it sequentially with L-lysine, protected as the 6-N-tBoc, and then separately with each of the two core tracers. Prior to purification, the t-Boc group was removed with trifluoroacetic acid in methylene chloride, to afford the following compounds:

V. L-leucyl-L-leucyl-L-lysyl-p-aminobenzoic[1-$^{13}$C] acid, ethyl ester
VI. L-leucyl-L-leucyl-L-lysyl-L-2-aminobutyric[1-$^{13}$C] acid, ethyl ester Each of these six tripeptides were homogenous on silica gel in:
n-butanol:acetic acid:water (3:1:1)
n-propanol:ethyl acetate:water (7:1:2)
n-heptane:n-butanol:acetic acid (3:2:1)
chloroform:methanol (9:1)

Hydrolytic (6M HCl) amino acid analysis of compounds and quantitation by GC/MS using tranexamic acid as internal standard showed that all compounds synthesized contained the correct molar fraction of each constituent amino acid to within 10 per cent variation from theory.

b) In-vitro Enzyme Assay Using Purified Enzymes

The suitability of substrates I–VI was tested by the enzymatic assay protocol of Svendsen. Freshly prepared solutions of bovine thrombin and bovine plasmin, from reconstituted lyophilized powders (Sigma) were prepared in tris-imidazole buffer at pH 8.4 to deliver nominally 0.5 NIH unit per ml of thrombin and 1 WHO unit of plasmin. After preincubation for 5 minutes at 37° C., 0.25 ml of an 0.5 mMolar solution of each substrate in the same aqueous buffer was added and the separate reactions incubated for 15 minutes at the same temperature. Reaction was stopped by addition of 1:9 concentrated HCl:methanol. Concentration of the supernatant, ion exchange chromatography on Dowex-50, with 2N ammonia water eluant, as a further desalting and deproteinizing step, afforded the amino acid fraction resulting from the enzymatic hydrolysis of the metaprobes. The concentration of p-aminobenzoic[1-$^{13}$C] acid (with tetradeutero isotopolog as internal quantitation standard) and of L-2-aminobutyric[1-$^{13}$C] acid (with pentadeutero isotopolog as internal quantitation standard) were then analyzed by isotope dilution GC/MS using the N-trifluoroacetyl propyl ester derivatives and the total hydrolytic conversion expressed as The susceptibility of the substrates prepared according to this example is shown in Table 14:

TABLE 14

| Thrombin and Plasmin Metaprobe Hydrolysis in Solution | | |
|---|---|---|
| Substrate | Product formed Thrombin | (nMoles/min/ml) Plasmin |
| I | 6.0 | 1.8 |
| II | 6.9 | 2.3 |
| III | 6.6 | 3.6 |
| IV | 7.8 | 3.1 |
| V | 0.3 | 7.2 |
| VI | 0.4 | 8.1 |

These results confirm the specificity relationships between thrombin and plasmin and concur with prior art in the findings that plasmin shows a broader specificity than thrombin, a fact that can be exploited in the design of differential assays for net pro-thrombotic or thrombolytic capacity in biological samples containing both enzymes. It follows, by extension, that the same result can be achieved in an in vivo setting where the interplay between both these actions of the coagulation system are more subtly intertwined.

c) In vitro Assay Using Whole Blood

In order to simulate more faithfully the microenvironment in which disseminated coagulopathies are known to occur, a similar test to the preceding proof of concept was carried out in whole blood from the septic rat model utilized in Example 10. Freshly drawn blood (0.5 ml) from three animals made septic by E. coli injection (Voisin et al.) was collected on days 2, 6 and 10 after insult followed by 0.5 ml of saline volume replacement. Blood was also collected from a separate cohort of three, untreated control rats.

An aliquot of 0.15 ml from each blood draw was stabilized with citrate and the plasma fraction collected by chilled centrifugation. This plasma was then tested for its prothrombin time (PTT) using the Thromboplastin-HS (with calcium) assay from Sigma.

The remaining unfractionated blood, also chilled, was dispensed into an evacuable 10 ml, uncoated, septum-sealed container, evacuated on a vacuum manifold to a residual manommetric reading of 10 Torr, backfilled with oxygen, and treated with 0.5 ml of buffered, isotonic reagents (at 5 mMolar concentration) via cannula through the septum. After gentle shaking to insure complete dispersal, the treated blood was incubated at 37° C. for 2 hours. A second aliquot containing 25 mg (approximately 7.5 units) of Type 6 crude dried Crotalus atrox venom (Sigma) in 0.01 Molar phosphate buffer, pH 7.9 was added to the serum/clot mixture and dispersed by vortexing for 2 minutes. Decarboxylation of free amino acids was allowed to proceed for 2 hours after which time the reaction tube was re-evacuated via cannula, treated with 1 ml of 2 Molar phosphoric acid, vortexed for three minutes, backfilled to atmospheric pressure with helium, and analyzed for $^{13}CO_2$ content by automated continuous flow isotope ratio mass spectrometry after cryogenic concentration of the headspace $^{13}CO_2/^{12}CO_2$ mixture. Sham controls, in which blood from normal control rats was treated with 0.5 ml of 0.25 Molar L-2-aminobutyric[1-$^{13}$C] acid were also examined. Recovery of label in these sham experiments averaged 75% of administered dose and validates the premise that any liberated core tracer from metaprobe incubation with whole blood can be detected after release of the $^{13}C$ tag by amino acid oxidase.

The results described in Table 15 show no difference in the PTT values obtained throughtout the time course of the septic challenge. By contrast, there are significant differences in the enzymatic profile of $^{13}CO_2$ release tag generation when metaprobe IV, which is thrombin selective, and when metaprobe VI, which is plasmin specific, are used in accordance with the method of this invention. Moreover, given the simulated in vivo environment, from the use of whole blood as the reaction matrix, the evidence obtained here further supports the claim of utility for the application of thrombin and plasmin metaprobes in vivo.

The dynamic measures obtained by expressing the metabolism of metaprobe IV as a percent of dose represent integrated estimates of total thrombin and plasmin load or reserve capacity in the circulatory system, simulated here via the use of oxygenated whole blood and followed longitudinally from the time of insult to recovery. These data may also be viewed as the net pro-coaggulant capacity of the host system, because of the preponderant selectivity of metaprobe IV for thrombin in the presence of plasmin. Similarly, the rate of hydrolytic disposition of metaprobe VI may be interpreted as a longitudinal index of plasmin capacity and, therefore, of anti-coagulant reserve. The difference between the two or the "net coagulant potential" (NCP), in turn, may also be expected to serve as a functionally similar, but dynamic index for many more of the same processes underlying the endogenous thrombin potential (ETP) test, described earlier. The NCP would be particularly advantageous as a substitute for conventional static plasma measurement technologies because it can be measured in vivo, as a metaprobe breath test in accordance with the method of Example I.

The action of APP on neuropeptide Y (NPY) provides a case in point. NPY, one of the most abundant neuropeptides in the mammalian brain, is a potent orexigenic agent when administered intrathecally, and is thought to be involved in the hypothalamic regulation of food intake, including an association with leptin action. Its possible involvement in angiogenesis, coupled with the fact that it is a sympathetic vasoconstrictor whose activity is determined, in part, by APP, which converts NPY to non-vasoconstrictive peptides. Further, the action of NPY is mediated by Y1 and Y2 receptors, and it is apparent that the proteolytic processing of NPY by APP, through removal of its amino terminal dipeptide, inactivates it for binding to Y1 and cleaves it to form an angiogenic Y2 agonist, implying a complex influence of APP on the function of this biologically active peptide. The high levels of APP found in various blood components may also be of physiological significance in cardiovascular and pulmonary disease. For example, working together with angiotensin converting enzyme, APP fully accounts for the degradation of bradykinin in the pulmonary vascular bed (Ansorge and Langner, Chapters 2–4; Barrett et al., Chapter 480; Cunningham and O'Connor).

Figure 20:
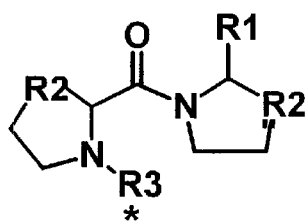
FIG. 20 shows the structure of aminopeptidase P metaprobes useful in the method of the invention.

A significant feature of the APP's substrate specificity can be exploited for the development of metaprobes in accordance with this invention. If the P2' position is occupied by proline or a proline analog, then the metaprobe is impervious to hydrolysis by X-pro dipeptidases, such as dipeptidyl peptidase II, dipeptidyl, peptidase IV and prolidase. Thus, attaching a rapidly metabolized amino acid tracer as the N-terminal to the Pro-Pro motif will afford a metaprobe with the desirable properties as shown in FIG. 20.

The preferred embodiment of this family of peptides was synthesized as follows: L-prolyl-L-proline ethyl ester was prepared by esterification of the dipeptide with HCl metha-

TABLE 15

Septic Rat Model: Thrombin and Plasmin Metaprobe Hydrolysis in Blood

|  | PTT (sec) | | Percent of Metaprobe IV | | Dose Metabolized VI | | NCP | |
| --- | --- | --- | --- | --- | --- | --- | --- | --- |
|  | Control | Septic | Control | Septic | Control | Septic | Control | Septic |
| Day 0 | 14 ± 2 | — | 22 ± 9 | — | 11 ± 5 | — | 11 ± 10 | — |
| Day 2 | — | 18 ± 3 | — | 76 ± 15 | — | 14 ± 7 | — | 62 ± 17 |
| Day 6 | — | 22 ± 4 | — | 39 ± 12 | — | 52 ± 17 | — | −13 ± 21 |
| Day 10 | — | 15 ± 4 | — | 25 ± 10 | — | 23 ± 12 | — | 2 ± 15 |

EXAMPLE XII

Use of the Method of the Invention with Aminopeptidase P (APP)

Aminopeptidase P is a zinc metalloenzyme that hydrolyzes a variety of peptides ranging in size from dipeptides to proteins. It cleaves the N-terminal amino acid (P1) when proline is found at the P1' position. The N-terminal group must have a free amino acid and the scissile bond must lie in the trans configuration. Its unique biological role involves the N-terminal processing of biologically active regulatory peptides, including those shown in Tables 9 and 10. As a consequence of the action upon them of APP, these peptides undergo a loss or alteration in their biological activity, or initiate a cascade of cell signalling actions leading to the eventual termination of their biological activity and the triggering of subsequent peptide/protein turnover as part of a catastrophic event in localized programmed cell death.

nol. The resulting salt was then acylated with N-tboc-glycine [1-$^{13}C$] via the mixed anhydride method, using isobutyl chloroformate and triethyl amine as base catalyst. The protected peptide was N-deblocked with trifluoroacetic acid in methylene chloride, titrated to pH 6 with alkaline ion exchange resins (Amberlyte 400) and recrystallised from isopropanol-acetone to afford a crystalline powder of glycyl [1-$^{13}C$]-L-prolyl-L-proline, ethyl ester, mp 225–227° C. The material was chromatographically pure in the solvent systems described in Example 11 and showed a 1:1.89 mole ratio of labeled glycine to proline upon hydrolysis and GC/MS amino acid analysis (as the N-trifluoroacetyl propyl esters).

Utility of this metaprobe was examined by incubating it, as described in Example 11 with two kinds of biological fluids representative of the milieu in which assays for aminopeptidase P would prove useful: a) human brochoalveolar lavage fluid (BAL) from normal controls and patients suffering from adult respiratory distress syndrome (ARDS), an inflammatory disease, secondary to sepsis and sepsis syndromes, with a high mortality; and b) plasma from rats two days after intravenous administration of a bacterial insult. Aliquots (0.25 ml) of 0.5 mmolar solutions of substrate in 0.01 M phosphate-buffer at physiological pH were treated with 0.25 ml of either reconstituted BAL (from freeze dried stock, as a 20% dry weight to volume homogenized suspension) or plasma, and the resulting formation of glycine[1-$^{13}$C] monitored periodically, during a two hour incubation period at 37° C., by isotope dilution GC/MS using a glycine[2,2-$^{2}$H$_2$, $^{15}$N] as the internal standard.

Table 16 shows the results expressed as cumulated percent dose of metaprobe metabolized in each of the biological fractions. As expected, the fractions taken during an acute inflammatory response were significantly elevated from basal values, thereby demonstrating the use of APP metaprobes to track the temporal properties of this enzyme as a biomarker for the inflammatory response and the dysregulation of the immune system associated with it. Thus, by using the method of this invention, as described in Example I, the metabolism of APP metaprobes in vivo, as for example those which would liberate a rapidly metabolized amino acid tracer, becomes useful as a whole-body measure of APP activity over time during the management of any disease process which alters the normal regulation of APP activity.

TABLE 16

Aminopeptidase P Metaprobe Hydrolysis in Inflammation

| Sample | % Dose metabolized | | Inflammatory condition |
| --- | --- | --- | --- |
| | Control | Test sample | |
| Human BAL | 22 ± 4 | 44 ± 14 | ARDS |
| Rat Plasma | 5 ± 4 | 28 ± 7 | Sepsis |

EXAMPLE XIII

Use of the Method of the Invention with Prolyl Oligopeptidase (PO)

Prolyl-oligopeptidase is a post-proline cleaving enzyme, provided that the proline is not situated at the N or C terminus of polypeptides and proteins. It is a widely distributed cytosolic enzyme, but is secreted under circumstances of tissue damage or in inflammatory conditions. It participates along with other proline specific peptidases in a complex process of cell signaling in so far as it participates in neuropeptide processing. In particular, PO titers appear to decrease significantly in patients suffering from melancholic depression, a point of significance since peptides such as arginine-vasopressin, beta-endorphin, thyroliberin, and luliberin are natural substrates for this enzyme. On the other hand a significant increase in serum PO has been found in manic and schizophrenic patients and in depressed patients undergoing treatment with fluoxetine. Similar confounding trends have been found with respect to PO in neurodegenerative disorders. It is elevated in post-mortem brains of some Alzheimer's patients, with suggestions hat PO plays a functional role in amyloidogenesis. If PO inhibitors are administered to rats prior to scopolamine induced amnesia, the amnesiac effect is attenuated, and this finding is replicatable with other PO inhibitors thought to be "cognitive enhancers". So, it is believed that PO normally degrades the "pGlu-asn-cys-cys-pro-arg" vasopressin-derived fragment that is involved in memory and related processes (Barrett et al., Chapter 125).

The link between PO and activation of cell mediated immunity, so prevalent in depressed patients, is also reflected in the increase of PO activity found in tissues taken during an inflammatory response, such as in mitogen challenge to skin, spleen after onset of lupus related immunopathologies, and in synovial membrane preparations from patients suffering with rheumatoid arthritis and also osteoarthritis, in whom matrix collagenases and other apoptotic enzymes become principal effectors of disregulation in the normal turnover of the proline rich bone and collagen precursor reservoir (Cunningham and O'Connor; Sandler and Smith, Chapter 17C).

As in preceding cases, several significant features of the APP's substrate specificity can be exploited for the development of metaprobes in accordance with this invention. The P2, P1 sites show a high affinity for aliphatic and aromatic amino acids, in a manner similar to DPPIV, described in Example 10, with the absolute requirement for proline at P1. Unlike DPPIV, and the related dipeptidyl peptidase II, PP requires a blocked N-terminal group and shows a higher affinity for neutrally charged moieties at the P1' site. So, by modifying the metaprobe for DPPIV, one obtains a suitable substrate for PP through the simple expedient of blocking both the N-terminus and the carboxyl C-terminus, the latter with an ester group known to be rapidly hydrolized by non-specific esterases (post PP cleavage). Metaprobes with these desirable properties are shown in FIG. 21

The preferred embodiment of this family of peptides was synthesized according the scheme described in Example 10, but using the ethyl ester of L-2-aminobutyric[1-$^{13}$C] acid and leaving the carboxyl protecting group after isolation of the tripeptide. The final step was accomplished by N-terminal protection with carbobenzyloxy-anhydride in aqueous base. The resulting N-carbobenzyloxy-glycyl-L-prolyl-L-2-aminobutyric [1-$^{13}$C] acid ethyl ester peptide was recrystallized from isopropanol-acetone to afford the final product as a crystalline, slightly deliquescent solid ester, mp 145–149° C. The material was chromatographically pure in the solvents systems described in Example 11 and showed a 1.04:98:1 mole ratio of labeled glycine:proline:aminobutyrate residues upon hydrolysis and GC/MS amino acid analysis (as the N-trifluoroacetyl propyl esters.)

Utility of this metaprobe was examined by incubating it, as described in Example 12 with four kinds of biological fluids representative of the milieu in which assays for aminopeptidase P would prove useful: a) human brochoalveolar lavage fluid (BAL) from normal controls and patients suffering from adult respiratory distress syndrome (ARDS), an inflammatory disease, secondary to sepsis and sepsis syndromes, with a high mortality; b) plasma from rats two days after intravenous administration of a bacterial insult; c) rat brain acetone powder; and d) rat lung acetone powder. Aliquots (0.25 ml) of 0.5 mMolar solutions of substrate in 0.01 M phosphate buffer at physiological pH were treated with 0.25 ml of either reconstituted BAL (from freeze dried stock, as a 20% dry weight to volume homogenized suspension), plasma, and the two acetone powders (reconstituted in a similar manner to the BAL fraction). The resulting formation of L-2-aminobutyric[1-$^{13}$C] acid was then monitored periodically, during a two hour incubation period at 37° C., by isotope dilution GC/MS using L-2-aminobutyric[2H$_5$] acid as the internal standard.

Table 17 shows the results expressed as cumulated percent dose of metaprobe metabolized in each of the biological fractions. As expected, the fractions taken during an acute inflammatory response were significantly elevated from basal values, thereby demonstrating the use of PP metaprobes to track the temporal properties of this enzyme as a biomarker for the inflammatory response and the disregulation of the immune system associated with it. Notably, and in contrast to the findings with DPPIV and APP, shown in previous examples, there did not appear to be an elevation of enzyme activity in plasma, while the appearance of PP in BAL from ARDS patients and in brain homogenate fractions were both predictable elevated. Thus, by using the method of this invention, as described in Example I, the metabolism of PP metaprobes in vivo, as for example those which would liberate a rapidly metabolized amino acid tracer, becomes useful as a whole-body measure of PP activity over time during the management of any disease process which differentially alters the normal regulation of PP activity.

TABLE 17

Prolyl oligopeptidase Metaprobe Hydrolysis in Inflammation

| Sample | % Dose metabolized | | Inflammatory condition |
| --- | --- | --- | --- |
| | Control | Test sample | |
| Human BAL | 30 ± 4 | 54 ± 13 | ARDS |
| Rat Plasma | 2 ± 4 | 8 ± 5 | Sepsis |
| Rat Brain | 44 ± 8 | — | Homogenate (acetone powder) |
| Rat Lung | 24 ± 12 | — | Homogenate (acetone powder) |

EXAMPLE XIV

Use of the Method of the Invention with Carboxypeptidase M (CPM) and Prolinase

As blood monocytes mature into macrophages, numerous functional and phenotypic characteristics are expressed, including changes in size, phagocytic capacity, and cytotoxic responsiveness to tumours. At the same time, the ability to stimulate T-cells declines in step with the shift in pattern of secreted cytokines and profile of surface recognition antigen. CPM is a phsphoinositol-linked, zinc dependent endopeptidase which is immunologically indistinguishable from the MAX1/MAX2 macrophage maturation antigen. CPM is able to process a spectrum of immuniogically important neuropeptides and kinins by removing their C-terminal arginine residue as part of either an agonist activation or inactivation signalling cycle. This enzymatic function has been demonstrated to progress in parallel with surface expression of the MAC antigen especially when monocyte-derived macrophage upregulation is stimulated, along with T-cell activation, as for example, during allogeneic transplant rejection or allergic alveolitis.

Pulmonary type I epithelial cells, which comprise 93% of the surface area, show the highest concentration of CPM by immunostaining methods, and the dramatically enhanced leakage of CPM in bronchoalveolar lavage fluid during pneumocystic or bacterial pneumonia and lung cancer. CPM is also present in 5–10 fold greater concentrations in edema fluid from experimental lung injury than under basal conditions in epithelial cell homogenates. Taken as a whole, these findings suggest an important role for CPM in the pathophysiology of lung disease and in the inflammatory conditions most closely associated with airway reactivity (Krause, et al.)

As in the case of DPPIV, which is also the CD26 Th-1 cell surface antigen, it would be desirable to monitor the progression of disease and of its treatment by tracking the temporal progress of CPM activity as a biomarker for the underlying parallel changes in monocyte-macrophage regulatory physiology. The use of a metaprobe in accordance with the method of this invention provides this diagnostic opportunity by permitting interorgan (i.e. across the lung) or whole body CPM activity to be measured expeditiously in vivo without resorting to ex-vivo, and therefore, static, cytochemical and immunohistological analysis. CPM is well suited to be probed as a gateway enzyme because its substrate specificity is unique among the carboxypeptidases and therefore less likely to afford artifactual cross-reactivity either with the secretory carboxypeptidases of the digestive system or with the highly compartmented intracellular enzymes mediating cellular apoptotic responses. Moreover, by its very nature, CPM is in effect a circulatory enzyme (although not a plasma enzyme per se) which can be presented with substrate conveniently by the intravenous route or bronchoalveolar irrigation (Barrett et al., Chapter 460).

Several significant features of the APP's substrate specificity can be exploited for the development of metaprobes in accordance with this invention. The enzyme cleaves C-terminal arginine and lysine residues and can be expected to show a preference for proline at the P2-position on the basis the putative S2 pocket geometry, derived from molecular modeling of the enzyme's activity towards arginyl peptides of various configurations. A N-terminal proline would also render any CPM substrate resistant to non-specific peptidase attack both before and after cleavage of the primary scissile bond at the P1-P1' junction. Upon liberation of the C-terminal lysine or arginine (P1') moiety, the remaining Pro-Xaa dipeptide can then be rapidly hydrolyzed by prolinase, another gateway enzyme that is reactive towards unblocked, N-terminal prolyl dipeptides, thereby liberating the Xaa. If this latter Xaa component is a rapidly metabolized, non-proteinogenic amino acid, then the metaprobe can be applied in a manner similar to the method of previous examples, especially if Xaa is taken to be L-2-aminobutyric acid. Metaprobes with these desirable properties are shown in FIG. 22.

The preferred embodiment of this family of peptides was synthesized by a variation of the peptide construction schemes already employed in previous examples. Accordingly, N-tBoc-L-proline was coupled to the L-2-aminobutyric[$1$-$^{13}$C] acid, methyl ester via isobutyl chloroformate assisted carboxyl activation in the presence of trietylamine and N,N-dimethylaminopyridine catalyst. Mild saponification in aqueous methanol with 2 equivalents of hydroxide gave the N-tBoc-prolyl dipeptide upon careful protonation, extractive work-up, and recrystallization from acetone. A portion of the dipeptide was deprotected with trifluoroacetic acid in methylene chloride and purified by ion exchange on Dowex 50 with 2N ammonia as eluant. Concentration and recrytallization from isopropanol ether gave L-prolyl-L-2-aminobutyric[$1$-$^{13}$C] acid mono hydrate (as determined by NMR), mp 158–161° C.

The balance of the dipeptide precursor was coupled to L-arginine, protected as the carboxyl t-butyl ester, again via the isobutyl chloroformate mixed anhydride formation. The resulting protected tripeptide was purified by trituration with ethyl acetate until becoming a friable solid, and then it was deprotected in trifluoroacetic acid/methylene chloride to yield an amorphous mass. Recrystallization from isopropanol/water gave crystals, mp 168–171° C. The material was chromatographically pure in the solvents systems described in Example 11 and showed a 1.01:1.04:0.97 mole ratio of labeled proline:aminobutyrate:arginine residues upon hydrolysis and GC/MS amino acid analysis (as the N-trifluoroacetyl propyl esters).

Utility of this metaprobe was examined by incubating it, as described in Example 12 with four kinds of biological fluids representative of the milieu in which assays for aminopeptidase P would prove useful: a) human bronchoalveolar lavage fluid (BAL) from normal controls and patients suffering from adult respiratory distress syndrome (ARDS), an inflammatory disease, secondary to sepsis and sepsis syndromes, with a high mortality; b) plasma from rats two days after intravenous administration of a bacterial insult; c) rat brain acetone powder; and d) rat lung acetone powder. Aliquots (0.25 ml) of 0.5 mMolar solutions of substrate in 0.01 M phosphate buffer at physiological pH were treated with 0.25 ml of either reconstituted BAL (from freeze dried stock, as a 20% dry weight to volume homogenized suspension), plasma, and the two acetone powders (reconstituted in a similar manner to the BAL fraction); and the resulting formation of L-2-aminobutyric[1-$^{13}$C] acid monitored periodically, during a two hour incubation period at 37° C., by isotope dilution GC/MS using L-2-aminobutyric[$^2$H$_5$] acid as the internal standard.

Sham controls, in which 0.25 ml of each of the four test fluids was treated with 0.25 ml of 0.25 Molar L-prolyl-L-2-aminobutyric[1-$^{13}$C] acid, were also examined. Recovery of L-2-aminobutyric[1-$^{13}$C] label in these sham experiments averaged 85% of administered dose across the board and validates the premise that core tracer liberation from the dipeptide after tripeptide hydrolysis is not limited by the absence of sufficient prolinase.

Table 18 shows the results expressed as cumulated percent dose of metaprobe metabolized in each of the biological fractions. As expected, the fractions taken during an acute inflammatory response were significantly elevated from basal values, thereby demonstrating the use of CPM metaprobes to track the temporal properties of this enzyme as a biomarker for the inflammatory response and the disregulation of the immune system associated with it. Notably, and in contrast to the findings with DPPIV, APP, and PO, shown in previous examples, there did not appear to be an elevation of enzyme activity in plasma, while the appearance of CPM in BAL from ARDS patients and in lung homogenate fractions were both predictably elevated. Thus, by using the method of this invention, as described in Example I, the metabolism of CPM metaprobes in vivo, as for example those which would liberate a rapidly metabolized amino acid tracer, becomes useful as a whole-body measure of CPM activity over time during the management of any disease process which differentially alters the normal regulation of CPM, an among them, in particular, diseases of the lung and airways.

TABLE 18

Carboxypeptidase M and Prolinase Metaprobe Hydrolysis in Inflammation

| Sample | % Dose metabolized | | Inflammatory condition |
|---|---|---|---|
| | Control | Test sample | |
| Human BAL | 23 ± 9 | 84 ± 14 | ARDS |
| Rat Plasma | 6 ± 3 | 28 ± 8 | Sepsis |
| Rat Brain | 4 ± 3 | — | Homogenate (acetone powder) |
| Rat Lung | 24 ± 12 | — | Homogenate (acetone powder) |

Use

Cancer treatment management

The number of new cancer cases has approximately doubled in the past decade due primarily to aging in the population People over 65 are ten times more likely to develop cancer than those under 65. Changing technology, earlier diagnosis, and better treatment have increased the five-year survival rate of cancer patients from approximately 39% in 1963 to approximately 54% in 1991. This improvement in survival rates has increased the demand for cancer related services. The methods of the invention have application in answering this demand, for example, in managing the nutritional support needs of cancer patients and in precisely tailoring chemotherapy doses for specific patients to facilitate adaptation to chemotherapy regimens.

Cancer is a group of over 100 complex diseases characterized by the uncontrolled growth and spread of abnormal cells. Therefore, chemotherapy is often complex and requires careful management to minimize adverse side effects. The oncologist must strike a balance between doses high enough to kill fast growing cancer cells and those that would cause permanent impairment to the rest of the person. This balance is critical, since it has been shown for some cancers that a doubling of chemotherapy concentration in the tumor site can create a tenfold increase in treatment effectiveness. Generally, the oncologist is forced to apply "average dose" drug regimens, with adjustments only for body mass.

Breath biopsies using the method of the invention will allow patient tailored dosing to maximize treatment effectiveness and minimize overdose side effects. For example, the glutathione cycle can be measured dynamically to determine the patient's ability to withstand the shock of high dose chemotherapy. Resilient patients can receive heavier doses with better outcomes, and less resilient can receive lower doses, avoiding costly side effects, or receive alternative therapies, such as radiation. Furthermore, many cancer patients require nutritional support during their course of treatment. The use of breath probes in the method of the invention to assess body composition, energy expenditure and needs, and nutritional status can aid in managing dietary supplementation. This highly targeted approach can help minimize wasting, or cancer cachexia, a major obstacle to recovery in cancer patients.

An important further consideration in the design of management approaches to cancer in its many forms is recognizing that presentation of any cancer constitutes a breech in natural and cellular immunity. In effect, cancer is linked to immune system dysregulation and represents a failure of immune surveillance that is often foreshadowed by subtle changes within the differentiation cycles of the hematopoetic systems. The method of the invention permits evaluation of the function of several important components in the immunological defense against cancer, in particular the activation of T-cells, B-cells, killer cells, as well as their interplay with neutrophils and macrophages. Because several key gateway enzymes, such aminopeptidase N, carboxypeptidase M, and dipeptidyl peptidase IV, are co-expressed on the surface of lymphoid cells, they become part of the body's "guard dog" mechanisms. Deviance from their normal patterns of expression and enzymatic activity can therefore be expected as early indicators of susceptibilty to cancer invasion not only in the lymphoid system itself, but also in other tissues, such as lung and gut endothelium and bone marrow, that are intimately associated with the functional integrity of the immune system.

Moreover, this invention has utility for monitoring of chemotherapeutic efficacy. Patients undergoing chemotherapy have altered cellular peptidase and other ecto-enzyme patterns, which are coincident which changes in T-cell and B-cell sub-population regulation; and these changes in enzyme levels can be used to monitor the effectiveness of chemotherapy, especially with metaprobe breath tests amenable to use at the bedside.

Viral load/infectious diseases

Viral load testing is a very helpful indicator of the assault intensity of pathogens in a given patient. However, such testing is at present conducted in a vacuum without a assessment of the patient's ability to withstand a given viral load. The effects of viral load are inversely related to cytoprotective capacity and antioxidant status, which are modulated principally by glutathione. Measurement of glutathione flux by the method of the invention will help determine likely responders to various therapies and allow more selective use of expensive antiviral treatments.

Therefore, treatment for patients with a number of infectious diseases and immune system disorders (including autoimmune disease) will benefit from the method of the invention. AIDS drug therapy, has evolved to include the concept of viral load as the method of determining appropriate drug regimens. For example, it has recently been reported that levels of glutathione in CD4 cells are "predictive of survival" for AIDS patients (Herzenberg et al., 1997).

The viral load concept is also becoming more relevant for management of patients with hepatitis. Glutathione probes in the method of the invention are able to differentiate patients with chronic active hepatitis and alcoholic liver disease (cirrhosis) Thus, the appropriate treatment for each condition can be provided to the patient.

Lymphoid cell sub-populations respond to antigen presentation in different ways. The essential steps during induction of cellular and humoral immune responses against bacteria and viruses involve a complex interplay of signalling events to coordinate the action and subsequent functional differentiation of T-cells, B-cells, NK cells, antibody secreting plasma cells and macrophages. The CD4+T effector cells (helper cells) are primarily responsible for coordination of the defense mechanisms. They activate as Th1 cells the cellular and as Th2 cells mainly the humoral arm of the immunological response. Both arms of the immunological response are activated in the initial response to infection, but there is an ultimate functional differentiation since bacteria are destroyed by activated macrophages and viruses are inactivated primarily by antibodies or by CD8+T cytotoxic effects on the viral host cells.

The net effect is that the biochemical signature of a viral infection is differentiable from that of a bacterial infection prior to symptom presentation. The cellular peptidases and ecto-enzymes of lymphoid cells undergo a concomitant pattern of expression with these cellular and humoral immunoprotective events and their divergence in response to viral or bacterial load can be detected by means of this invention. In effect, by monitoring one or more of the gateway enzymes associated with lymphoid cell differentiation, the biochemical signature of a viral or bactrerial load can be used to quantify the magnitude of that load and its change over time as a function of intervention.

For example, HIV replication in blood cells can be monitored by means of molecular biological assays ex vivo which, in effect, count the genetic "load" that the virus is imposing on its host cells. A sensitive measure of HIV replication can be important as a predictor of rapid movement into the AIDS state from the HIV seropositive stage of the disease. Since the virus replicates in the lymphocytes and monocytes, altering their characteristic cellular peptidase and ecto-peptidase expression, monitoring specific enzyme levels can provide an index of protease capacity in vivo as a dynamic alternative to the measurement of ex-vivo viral load. Each of the ectopeptidases which can be assayed by the methods of this invention, as for example the dipeptidyl peptidase/CD26 Th1, aminopeptidase N/CD13 and aminopeptidase A/BP-1/6C3 ectoenzymes, can be used as surrogate markers in vivo for the time course and magnitude of viral disturbance of the lymphoid system.

Moreover, the use of tracer probes for cellular peptidase and ecto-enzymes associated with divergent pathways of the immune response can be used to assess the differential impact of viral loads in the presence of adventitious, but equally damaging, bacterial insults. In the management of AIDS patients, the early diagnosis of tuberculosis is important to insure rapid recovery and to reduce the chance of further complications. The objective of such a test using this invention is to distinguish tuberculosis positive from negative patients by means of tracking differential changes in the patterns of enzymatic activity that result when lymphoid cells directed at bacterial insults are also activated. For example, the differential expression of ectoenzymes in activated macrophages, otherwise at basal levels during the early phases of viral infection, can be used to advantage in determining an optimal therapeutic intervention at an earlier stage.

Management of diabetes

Diabetes is a disease in which the body does not produce or properly use insulin, a hormone that is needed to convert sugar, starches and other food into energy needed for daily life. There are 15.7 million people or 5.9% of the population in the United States who have diabetes. Based on death certificate data, diabetes contributed to more than 187,000 deaths in 1995. Diabetes is a chronic disease that has no cure. The total annual economic cost of diabetes in 1997 was estimated to be $98 billion dollars. That includes $44.1 billion in direct medical and treatment costs and $54 billion for indirect costs attributed to disability and mortality.

There are two major types of diabetes. Type 1 diabetes accounts for 5–10 percent of diabetes. This autoimmune disease, in which the body does not produce any insulin, most often occurs in children and young adults. People with Type 1 diabetes must take daily insulin injections to stay alive. Type 2 diabetes, or non-insulin dependent diabetes, accounts for 90–95 percent of diabetes. Type 2 diabetes is nearing epidemic proportions, due to an increased number of older Americans, and a greater prevalence of obesity and a sedentary lifestyle. As discussed in the Examples, the methods of the invention can make management of both forms of diabetes significantly easier.

The methods of the invention are also useful as management tools for the endocrine manipulation of diabetes with peptide drugs other than insulin itself. For example, the glucagon like proteins, Glp1 and Glp2, and a variety of orexigenic drugs and neuropeptides are used to stimulate the underlying metabolic processes which mediate insulin resistance, control the balance between lipogenesis and gluconeogenesis, or alter the balance of agonist and antagonist cell signalling mechanisms at the site of the insulin receptor. Cellular ectopeptidases, and in particular, the proline specific gateway enzymes constitute the principle mechanisms for degradation of these stimulatory and inhibitory peptides, both the exogenous therapeutic agents and the endogenous effectors, in the cascade of events leading towards euglycemia. The response of the host to these peptide stimuli is proportional to the systemic "load" of protease activity which inactivates them.

This type of whole body enzymatic capacity can be assessed effectively by the use of gateway enzyme metaprobes as a means to establishing suitable dosing regimens. In particular, the use of Type II antidiabetic drugs designed to specifically to inhibit cellular peptidases would benefit from an in vivo therapy metric that can titrate the residual peptidase capacity, as for example a metaprobe breath test for dipeptidyl peptidase IV and its regulatory role over GLP1 and Neuropeptide Y.

Critical care/intensive care applications

High risk, high cost patients in ICUs, step down units, and cardiovascular units occupy 35% of US hospital beds and 50% of hospital coats. Assessments of such patients today, where they exist, include risky and expensive invasive approaches, empirical clinical observations, or non-patient specific computer algorithms. Apache Medical Systems, a software company that provides prospective management tools for such patients, believes that $20 billion in savings could be generated with better resource allocations. Use of the methods of the invention to obtain patient specific analyses will permit much better resource allocations for these patients than currently existing population-based indices.

For example, the methods of the invention allow patient-specific analysis that will be much better accepted by intensive medicine practitioners than population-based decision support systems such as those distributed by Apache Medical Systems. Tracer probes can be used to measure biochemical activity related to oxidant stress and the immune system response to provide early stage guidance for management of patients in intensive care units. To illustrate, seriously ill patients with comparable Apache scores have been shown to have widely divergent outcomes. The methods of the invention conceptually differentiate such patients with similar Apache scores by prognosis and allow proactive clinical interventions.

Perhaps the most difficult and unsolved clinical problem in critical care is the diagnosis and management of sepsis and sepsis syndromes, which together with the onset of organ failure and adult respiratory distress syndrome account for approximately a 45% mortality rate in patients so affected. There exists widespread consensus that dysregulation of the immune system, mediated by runaway cytokine storms, is the root cause; but it has proven extremely difficult to follow this dramatic course of events at the bedside with any other than cumbersome diagnostic and prognostic tools. Gateway enzymes that are found on the surface of lymphoid cells, and in particular those which are proline specific peptidases, offer a unique opportunity for diagnostic intervention because their enzymatic activity is an integral part of the homeostatic and allostatic machinery of the body. As shown in the Examples, these gateway enzymes participate in the costimulation, activation, and degradation of all the principal cytokines and kinins. Both the natural course of unchecked disease and the efficacy of intervention invariably become reflected in the ebb and flow of gateway enzymatic capacity, which the method of this invention provides a means to quantitate.

Based on the complexity of targets and pathways that need to be modified therapeutically, it has become evident that an effective strategy for controlling the dyshomeostasis of a traumatic insult, including sepsis, involves the use of many potent drugs a) to prevent excessive macrophage stimulation by neutralizing the impact of circulating inflammatory cell signals, b) down regulating the inflammatory activity of lymphoid cells, and c) restoring cell mediated immunity to overcome the post-traumatic functional paralysis. These are precisely the kinds of interventions that can a be monitored for efficacy and outcome by using the tracer probes described in the Examples as biomarkers for the achievement of therapeutic milestones. Indeed, given the essential role of cellular peptidases and ectopeptidases, any intervention that purports to affect interleukins and growth factors that are regulated by gateway enzymes, as for example those listed in Tables 9–11 of this invention, would be enhanced by the concomitant application of a metaprobe test.

In addition to providing a new approach to monitoring therapeutic interventions aimed at the lymphoid cell regulation, the method of the invention is also suited as a technique for uncovering imbalances in the coagulation cascade, which otherwise might go undetected during anti-coagulant therapies that are used so frequently in both critical and intensive care. When assessed in vivo with tracer probes aimed at uncovering the total pro-thrombotic or pro-thrombolytic capacity, the gateway enzymes in the circulatory system, such as thrombin and plasmin, become predictors of homeostatic competency in a manner that supercedes the information provided by conventional ex vivo clotting times. In particular, tracer metaprobes should prove important tools for the rational management of the more subtle, disseminated intravascular coagulation disorders which lead to organ system failure via otherwise undiagnosable mechanisms of microemboli formation.

In addition, monitoring the enzymatic capacity of gateway enzymes, such as aminopeptidase P, a cellular peptidase of platelets, has utility for the management of cardiovascular disease. Atherosclerosis results in the deposition of platelets and other cellular components into the walls of coronary cells, thereby disrupting the biochemical homeostasis of endothelial cells. This process accelerates the loss of elasticity of the vessels and eventually leads to significant morbidity and mortality. It has been shown that in these patients, as many as 20% of the platelets are in the activated state, displaying a wide spectrum of ecto-enzymatic activity identifiable in vivo by gateway enzyme metaprobes. Evaluation of platelet enzymatic diversity in situ, within their characteristic milieu of interactions with other cells and tissues of the lymphoid and hematopoietic systems, can permit the identification of patients with active, but covert, atherosclerotic processes and provide therapeutic endpoints for the more rational administration of disease altering drugs.

Furthermore, this invention has utility in the diagnosis and management of transplant rejection. The practice of this invention as a tool for monitoring those gateway enzymes, which are dramatically up-regulated in the machinery of cellular immunity, can be useful to monitor the acceptance of an organ transplant. All patients are given immunosuppressants to prevent organ rejection and therefore it is difficult to distinguish infection from rejection, an objective that can be met by monitoring the gateway enzymatic signature of the rejection process.

Neurodegenerative disorders

Probes for early diagnosis of Parkinson's disease and Alzheimer's disease, among other neurodegenerative disorders, are also candidates for use in the methods of the invention. It is believed that these disorders have a connection to antioxidant stress and the gluthione/NO cycles described above.

For example, the triggering of programmed cell death by NO and its successor oxidant radical cascade is a principal causative agent of de-myelinating and depolarizing disorders that result from the gradual destruction and failed repair of neuronal and accompanying cells. Glutathione mediated antioxidant detoxifying mechanisms are the natural cytoprotectants, whose beneficial action can become irreversibly overwhelmed, so that diagnostic methods for monitoring both the progression of oxidant attack and the repletion of oxidant capabilities would be desirable tools in patient management, even at the early onset stages before full manifestation of clinical symptoms. Dementia, multiple sclerosis, and amyotrophic lateral sclerosis all could be managed more effectively if the management could be aided by objective, biochemical indices of antioxidant capacity both at the whole body level and in the most affected organ system. The use of the kinds of metaprobes described herein would be an appropriate, minimally invasible approach to obtain dynamic, biochemical information to augment the traditional static clinical chemistries and radiographic findings in these disorders.

The various cell types of the nervous system respond to neuroendocrine stimuli. These higher order chemical messengers regulate the patterns of biochemical activity that ultimately yield normal neurotransmission but also normal development, growth and repair of the affected cells. In this sense, the nervous system is integrated with the circulatory and lymphatic systems, since the regulatory hormones are often secreted and then translocated via the microvasculature by diffusive routes until intercepted by transporters and receptors. Cellular peptidases and membrane bound ectopeptidases are principal processors of neuropeptides, such as the vassopressins and endorphins. They also modulate the turnover of effector proteins, such as amyloid, as well as the conformation of receptor proteins in memory and other cognitive processes. Alzheimer's, Parkinson's, depression and dementia all share a biochemical link in that their biochemical trajectory is profoundly affected by the presence and proteolytic capacity of the cellular peptidases, and in particular those showing proline directed site specificities. Use of tracer metaprobes to follow the profile of upregulation or downregulation both in the expression patterns and in the substrate turnover of these enzymes, as provided for in this invention, offers an unprecedented opportunity for the management of neurological disorders by tracking an important aspect of their biochemical "fingerprint" in vivo. The utility of tracer metaprobes in this context ranges from providing diagnostic information about cellular processes to insights about the dose ranging of specific drugs, such as anti-depressants, that stimulate the neuroendocrine system by modes of action that are inextricable from the biochemistry of the cellular peptidases described in this invention.

Inflammatory and autoimmune disorders

When turned against its own host, the phenomenon of cellular immunity is no longer a protective mechanism but a causative agent in disease. Auto-immune disorders emulate the inflammatory response that otherwise would have been triggered by exogenous pathogens or genetically derailed endogenous cells, i.e. cancer. It is for this reason that monitoring the normal function of the immune system via the biochemical signature of unique enzymes within lymphoid cells takes on a similar utility to that demonstrated when these enzymes are monitored in diseases attributable to pathogenic origin. For example, this invention has utility for differential diagnosis of Lupus from rheumatoid arthritis, two prevalent auto-immune inflammatory disorders with different patterns, and degrees, of gateway enzyme expression with lymphoid cells. In the early progression of disease the symptoms for lupus erythematosis and rheumatoid arthritis are sufficiently similar that differential diagnosis of the disease is difficult, especially when a lupus patient presents with early arthritic involvement. This failure of diagnosis has clinical consequences since it delays the administration of the correct anti-inflammatory therapy. Lupus can be a clinically aggressive disease, and it is beneficial to the patient to have the correct diagnosis at an early date. These patients have different cellular peptidases and leucocyte ecto-enzymes in activated states, meaning that the gateway enzyme metaprobe methodology is the modality to use for a differential diagnosis, as well as a therapy metric upon treatment.

This invention has still further utility for differential diagnosis of rheumatoid arthritis from osteoarthritis. Rheumatoid arthritis is an aggressive autoimmune disease which results in destruction of the panus of the joint. Its biochemical signature, as evidenced by enzymatic activity within lymphoid cells, is fundamentally different from that of osteoarthritis, which is a degenerative disease of the aging joint that is not mediated by immunological vectors. The latter's biochemical signature is characterized by disregulation of proline processing enzymes, different from those associated with mechanisms of cellular immunity and therefore differentiable by means of the tracer metaprobes described in the Examples and applied as in vivo diagnostic procedures.

The diagnosis and management of vasculitis offers another opportunity for practicing the methods of this invention to the advantage of the patient. Vasculitis is an autoimmune inflammatory disease of blood vessels generally in the extremities. Patients with this disease typically have nondescript complaints of pain which do not permit diagnosis until considerable damage has been completed on the vascular system by the unchecked action of the immune cells. Since it is an autoimmune disease caused by circulating immune cells, the disclosed methodology can provide the needed information to assist in an early diagnosis via the use of tracer metaprobes that uncover the patterns of cellular peptidase and ectopeptidase activity which are characteristic in the inflammatory response of the vascular system.

REFERENCES

Abell, A. Advances in Amino Acid Mimetics and Peptidomimetics. Vol 1. Greenwich (Conn.): JAI Press Inc., 1–302 (1997)
Allen, R. H. et al., U.S. Pat. No. 4,940,568 (1990)
Allen, R. H. et al., U.S. Pat. No. 5,394,560 (1994)
Allen, R. H. et al., U.S. Pat. No. 5,438,017 (1995)
Allison, R. D., Methods in Enzymology, 113:419–437 (1985)
Amann, S. T. et al., Pancreas, 13:226:230 (1996)
Ammon, H. P. T. et al., Advances in Drug Research, 27:1–228 (1996)
Ansorge, S. and Langner, J. (Eds.), Cellular Peptidases in Immune Functions and Diseases. New York: Plenum Press, 1–338 (1997)
Aurell, L. E. et al., U.S. Pat. No. 4,028,318 (1977)
Babine, R. E. and Bender, S. L.Chemical Reviews, 97:1359–1472, (1997)
Barrett, A. J., Rawlings, N. D. and Woessner, J. F. Handbook of Proteolytic Enzymes, New York, Academic Press, 1–1666 (1998)
Barrett, P. H. R. et al., Metabolism, 47:484–492 (1998)
Barshop, B. A. et al., Pediatric Research, 30:15–22 (1991)
Beaumier, L. et al., Biomed. Environ. Sci., 9:296–315 (1996)
Beckman, J. S. and Koppenol, W. H., Am. J. of Physiol., 271:C1424–C1437 (1996)
Bellini, M. et al., Alcohol and Alcoholism, 32:259–266 (1997)

Benathan, M., British Journal of Dermatology, 137:721–727 (1997)

Bianchi, G. et al., Journal of Hepatology, 26:606–613 (1997)

Bier, D. M., European Journal of Pediatrics, 156 (Supplement):S2–S8 (1997)

Bircher, J. and Preisig, R., Methods in Enzymology, 77:1–9 (1981)

Blomback, G. E. B. et al., U.S. Pat. No. 3,884,896 (1975)

Bostom, R. et al., Clinical Chemistry, 41:948–949 (1995)

Bourne, D. W. A. Mathematical Modeling of Pharmacokinetic Data, Lancaster (Pa.): Technomic Publishing Company, 1–139 (1995)

Brandt, W., et al., European Journal of Biochemistry, 236:109–114 (1996)

Bressler, P. et al., Diabetologia, 39:1345–1350 (1996)

Browne, T. R. (Ed.), Stable Isotopes in Pharmaceutical Research, Amsterdam: Elsevier, 1–219 (1997)

Browne, T. R. et al., Journal of Clinical Pharmacology, 33:246–252 (1993)

Castillo, L. et al., Am. J. of Physiol., 268:E360–E367 (1995)

Castillo, L. et al., Pro. Nat'l Acad. Sci. (USA), 91:6393–6397 (1994)

Castillo, L. et al., Proc. Nat'l Acad. Sci. (USA), 93:11460–11465 (1996)

Caughey, G. H., Am. J. Resp., Cell and Mol. Biol., 4:387–394 (1991)

Charton, M. Methods in Enzymology, 112:323–346 (1985)

Claeson, K. G. et al., U.S. Pat. No. 4,279,810 (1981)

Cobelli, C. et al., Am. J. of Physiol., 253:E551–E564 (1987)

Cobelli, C. et al., Am. J. of Physiol., 262:E968–E975 (1992)

Colombato, P. et al., Journal of Viral Hepatitis, 4:143 (1997)

Cook, H. T. and Cattell, V., Clinical Science, 91:375–384 (1996)

Crane, B. R. et al., Science, 278(5337):425–431 (1997)

Cunningham, D. F. and O'Connor, B. O., Biochimica Biophysica Acta, 1343:160–186 (1997)

D'Argenio, D. Z., (Ed.), Adv. Meth. of Pharmacokinetic and Pharmacodynamic Systems Analysis, New York: Plenum Press, 3–211 (1991)

Davidson, W. D., Metabolism, 30:596–611 (1981)

Deshmukh, D. R. et al., Archives of Physiol. and Biochem., 105:32–37 (1997)

Dolle, R. E., Molecular Diversity, 3: 199–233 (1998)

Douglas, K. T., in Dolphin, D. et al., (Eds.), *Glutathione*, New York: Wiley, 243–279 (1989)

Ekenstam, B. T. et al., U.S. Pat. No. 4,137,225 (1979)

Ekenstam, B. T. et al., U.S. Pat. No. 4,247,454 (1981)

El-Khoury, A. E., Am. J. of Physiol., 271:E563–E573 (1996)

Estess, P. et al., Journal of Clinical Investigation, 102:1173–1182 (1998)

Ferrari, R. et al., Am. J. of Med., 91(Supplement 3C):95S–105S (1991)

Fleischer, B. Dipeptidyl Peptidase IV (CD26) in Metabolism and the Immune Response. New York, Springer-Verlag, 1–325 (1995)

Fonseca, V. A. et al., Metabolism, 47:686–689 (1998)

Gargiulo, R. J. et al., U.S. Pat. No. 4,275,153 (1981)

Gargiulo, R. J. et al., U.S. Pat. No. 4,336,186 (1982)

Giorgi, G. et al., Current Therapeutic Research, 52:461–467 (1992)

Goding, J. W. and Howard, M. C. Immunological Reviews, 161:5–10 (1998)

Goldberg D. M. and Durie, P., Clinical Biochemistry, 26:253–275 (1993)

Griffith, O. W., Methods in Enzymology, 113:461–468 (1985)

Guttormsen A. B. et al., Am. Journal of Clinical Nutrition, 63:194–202 (1996)

Hansch, C., Drug Metabolism Reviews, 1:1–14 (1972)

Hasegawa, T. et al., Journal of Pediatric Surgery, 32:1548–1551 (1997)

Hebert, L. F. et al., Journal of Clinical Investigation, 98:930–936 (1996)

Hecker, M. et al., FEBS Letters, 294:221–224 (1991)

Heins, J. et al., Biochimica Biophysica Acta, 954:161–169 (1988)

Heinzel, G. et al., TopFit (Version 2), Stuttgart: Gustav Fischer, 1.5–5.133 (1993)

Hellerstein, S. L., U.S. Pat. No. 5,338,686 (1994)

Hemker, H. C. and Beguin, S. Thrombosis and Haemostasis 74:134–138 (1995)

Herzenberg L. A. et al., Proc. Nat'l Acad. Sci. (USA), 94:1967–72 (1997)

High, K. A. and Roberts, H. R., (eds.), Molecular Basis of Thrombosis and Hemostasis, New York, Marcel Dekker, 1–985, (1995)

Hofman, A. S. and Cole, S. G., U.S. Pat. No. 4,676,974 (1987)

Holgate, S. T., Ciba Foundation Symposium, 206:5–34 (1997)

Houston, D. P., Journal of the American Medical Association, 278:1804–1814(1977)

Hu, M-K. et al., Bioorganic and Medicinal Chemistry Letters, 9:563–568 (1999)

Hull, J. et al., Thorax, 52:557–560 (1997)

Imondi, R. A., U.S. Pat. No. 3,806,592 (1974)

Jackson, A. A. et al., Journal of Nutrition, 126:2814–2822 (1996)

Jaffe, G. E., et al., U.S. Pat. No. 5,733,719 (1998)

Jaffe, G. E., et al., U.S. Pat. No. 5,776,720 (1998)

Kalayjian, R. C. et al., Journal of Acquired Immune Deficiency Syndromes, 7:369–374 (1994)

Katz, J. Metabolism, 38:728–733 (1989)

Kazmierski, W. M. (Ed.) Peptidomimetics Protocols. Totowa (N.J.): Humana Press, 1–546 (1999)

Kher, A., et al., Haemostasis 27:211–218 (1997)

Klein, E. R. and Klein, P. D. (Eds.), Stable Isotopes, Proc. Third International Conf., New York: Academic Press, 1–304 (1979)

Kolhouse, J. F. et al., U.S. Pat. No. 5,506,147 (1996)

Korom, S. et al., Transplantation, 63:1495–1500 (1997)

Krause, S. W., et al., Immunological Reviews, 161:119–127, (1998)

Kyle, D. J., U.S. Pat. No. 5,466,434 (1995)

Kyrle, P. A. et a., Arteriosclerosis Thrombosis and Vascular Biology, 18:1287–1291

Lagerwerf, F. M. et al., Analytical Biochemistry, 257:45–52 (1998)

Laghi, V. et al., Hepato-Gastroenterology, 44:1182–1186 (1997)

Lange, G. L. et al., U.S. Pat. No. 5,432,058 (1995)

Lassen, N. A. and Perl, W. Tracer Kinetic Methods in Medical Physiology, New York: Raven Press, 1–189 (1979)

Levi, M. et al., Journal of the American Medical Association, 270:975–979 (1993)

Levy, M. A. et al., Journal of Nutrition, 128:671–676 (1998)

Liao, Y. and Husain, A., Canad. J. of Cardiol., 11(Suppl. F):13F–19F (1995)

Lucas, F. J. et al., U.S. Pat. No. 5,698,411 (1997)

Malloy, C. R. et al., U.S. Pat. No. 5,413,917 (1995)

Marschall, H.-U. et al., J. of Biol. Chem., 264:12989–12993 (1989)

Maury, C. P. J. Clinical Chemistry, 27:2058–2060 (1981)

McClain, D. and Crook, E. D. Diabetes, 45:1003–1009 (1996)

McCully, K. S. Annals of Clinical and Laboratory Science, 24:134–152 (1994)
McKnight, G. L. et al., W.O. Patent No. 93/21330 (1993)
Meister, A. and Griffith, O. W., Methods in Enzymology, 113:445–451 (1985)
Meister, A., in Dolphin, D. et al., (Eds.), Glutathione, New York: Wiley, 367–474 (1989)
Meister, A., Methods in Enzymology, 113:438–445 (1985)
Mohan, O. E. et al., Respiration Physiology 86:159–170 (1991)
Mohan, O. E., et al. Respiration Physiology, 86:159–170 (1991)
Morimoto, C. and Schlossman, S. F., Immunological Reviews, 161:55–70 (1998)
Nerlich, A. G. et al., Diabetes, 47:170–178 (1998)
Nieuwenhuys, C. M. A. et al., Arteriosclerosis Thrombosis and Vascular Biology, 18:1480–1489, (1998)
Nilsson, K. et al., Europ. J. of Clin. Invest., 26:853–859 (1996)
Nishi, K. et al. European Patent No. 0 824 149 A2 (1998)
Nissen, S. L., et al., U.S. Pat. No. 5,628,328 (1997)
Nygard, O. et al., N. E. J. of Med. 337:230–236 (1997)
Oberley, L. W., Free Radical Biology and Medicine, 5:113–124 (1998)
Ohlhauser, C. et al., Onkologie, 20:126–131 (1997)
Packer, L. (Ed.), Nitric Oxide (Part A, Methods in Enzymology, Vol. 268), 1–489 (1996)
Packer, L. (Ed.), Nitric Oxide (Part B, Methods in Enzymology, Vol. 269), 1–467 (1996)
Patterson, B., Metabolism, 46:322–329 (1997)
Pawlotsky, J. M. et al., Journal of Medical Virology, 54:26–37 (1998)
Picot, D. et al., Gastroenterol. Clinique et Biologique, 21:562–566 (1997)
Rahfeld, J. et al., Biological Chemistry (Hoppe-Seyler), 372:313–318 (1991)
Redgrave, T. G. and Martins, I. J., U.S. Pat. No. 5,756,067 (1998)
Rinderknecht, H. in Go, V. L. W. et al., (Eds.), The Exocrine Pancreas: Biology, Pathophysiology, and Diseases, New York: Raven Press, 163–183 (1986)
Robinson, G. B., Biochemical Journal, 108:275–285 (1968)
Sandier M. and Smith, H. J., (Eds.) Design of Enzyme Inhibitors as Drugs, Oxford, Oxford University Press, 1–827 (1994)
Schaffer, M. and Barbul, A., British Journal of Surgery 85: 444–460 (1998)
Sedo, A. et al., Physiological Reviews, 45:169–176 (1996)
Shankar, R. R. et al., Metabolism, 47:573–577 (1998)
Sies, H. (Ed.), Antioxidants in Disease Mechanisms and Therapy (Advances in Pharmacology, Vol. 38), 1–415 (1997)
Simonian, N. A. and Coyle, J. T., Ann. Rev. Pharmacol. and Toxicol. 36:83–106 (1996)
Skidgel, R. A. and Erdos, E. G., Immunological Reviews, 161:129–141 (1998)
Stamler, J. S. and Slikva, A., Nutrition Reviews, 1:1–130 (1996)
Svendsen, L. G. U.S. Pat. No. 4,070,245 (1978)
Szewczuk, A. and Wellman-Bednawska, M., Clinica Chimica Acta, 84:19–26 (1978)
Tate, S. S. and Meister, A., Methods in Enzymology, 113:400–419 (1985)
Topliss, J. G., (Ed.), Quantitative Structure-Activity Relationships of Drugs, New York: Academic Press, 1–375 (1983)
Tsai, K. et al., Gut, 42:850–855 (1988)
VanHoof, G. et al., FASEB Journal, 9:736–744 (1995)
Vann, L. S. et al., Proceedings of the Western Pharmacology Society 20:91–95 (1977)
Vann, L. S. et al., Proceedings of the Western Pharmacology Society, 20:91–95 (1977)
Vervloet, M. G., at al., Seminars in Thrombosis and hemostasis, 24:33–44 (1998)
Vita, J. A. et al., Journal of Clinical Investigation 101:1408–1414 (1998)
Voisin, L. et al., Journal of Clinical Investigation, 97:1610–1617 (1996)
Wagner, D. A. et al., U.S. Pat. No. 5,386,832 (1995)
Wagner, J. G. Pharmacokinetics for the Pharmaceutical Scientist, Lancaster (Pa.): Technomics Publishing Co., 1–316 (1993)
Wagner, J. G., J. Pharmacokinetics and Biopharmaceutics, 5:443–478 (1976)
Watkins, P. B., U.S. Pat. No. 5,100,779 (1992)
Weichert, W. and de Graaf, A. A., Advances in Biochemical Engineering, 54:1–151 (1996)
White, R. D. et al., Acute Toxicity Data, 1:164–165 (1992)
Wielders, S. et al., Thrombosis and Haemostasis 77:629–636 (1997)
Wolfe, R. R., Radioactive and Stable Isotope Tracers in Medicine, New York: Wiley-Liss, 1–395 (1992)
Yokoi, I. Et al., Neuropharmacology, 33:1261–1265 (1994)

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method of determining the in vivo conversion activity of a Class I, II or III gateway enzyme, said method comprising the steps of:
   identifying a Class I, II or III gateway enzyme to be assayed;
   selecting a labelled metaprobe for said enzyme, said metaprobe being selected so that when acted upon by said enzyme, at least one labelled end product that is directly detectable is produced;
   administering to a patient a defined amount of said labelled metaprobe; and
   determining the extent of conversion of said metaprobe to said labelled end product by said enzyme.

2. The method of claim 1 wherein said gateway enzyme is dipeptidyl peptidase IV and said metaprobe is glycyl-L-prolyl-L-2-aminobutyric[1-$^{13}$C] acid.

3. The method of claim 1 wherein said gateway enzyme is dipeptidyl peptidase IV and said metaprobe is glycyl-L-prolyl-p-aminobenzoic[1-$^{13}$C] acid.

4. The method of claim 1 wherein said gateway enzyme is thrombin and said metaprobe is N-acetyl-D-phenylalanyl-L-prolyl-L-arginyl-p-aminobenzoic[1-$^{13}$C] acid, ethyl ester.

5. The method of claim 1 wherein said gateway enzyme is thrombin and said metaprobe is N-acetyl-alycyl-L-prolyl-L-arginyl-p-aminobenzoic[1-$^{13}$C] acid, ethyl ester.

6. The method of claim 1 wherein said gateway enzyme is thrombin and said metaprobe is N-acetyl-D-phenylalanyl-L-prolyl-L-arginyl-2-aminobutyric[1-$^{13}$C] acid, ethyl ester.

7. The method of claim 1 wherein said gateway enzyme is thrombin and said metaprobe is N-acetyl-L-glycyl-L-prolyl-L-arginyl-2-aminobutyric[1-$^{13}$C] acid, ethyl ester.

8. The method of claim 1 wherein said gateway enzyme is plasmin and said metaprobe is N-acetyl-L-leucyl-L-leucyl-L-lysyl-p-aminobenzoic[1-$^{13}$C] acid, ethyl ester.

9. The method of claim 1 wherein said gateway enzyme is plasmin and said metaprobe is N-acetyl-L-leucyl-L-leucyl-L-lysyl-2-aminobutyric[1-$^{13}$C] acid, ethyl ester.

10. The method of claim 1 wherein said gateway enzyme is aminopeptidase P and said metaprobe is glycyl[1-$^{13}$C]-L-prolyl-L-proline, ethyl ester.

11. The method of claim 1 wherein said gateway enzyme is prolyl oligopeptidase and said metaprobe is N-carbobenzyloxy-glycyl-L-prolyl-2-aminobutyric[1-$^{13}$C] acid, ethyl ester.

12. The method of claim 1 wherein said gateway enzyme is carboxypeptidase M and said metaprobe is N-L-prolyl-L-2-aminobutyryl[1-$^{13}$C]-L-arginine.

* * * * *